US011983309B2

(12) United States Patent
Nakano

(10) Patent No.: US 11,983,309 B2
(45) Date of Patent: May 14, 2024

(54) DEVICE AND METHOD TO ACQUIRE TIMING OF BLINK MOTION PERFORMED BY A DIALOGUE DEVICE

(71) Applicant: JAPAN SCIENCE AND TECHNOLOGY AGENCY, Kawaguchi (JP)

(72) Inventor: Tamami Nakano, Suita (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 855 days.

(21) Appl. No.: 17/023,992

(22) Filed: Sep. 17, 2020

(65) Prior Publication Data

US 2021/0004078 A1    Jan. 7, 2021

Related U.S. Application Data

(63) Continuation of application No. PCT/JP2019/009115, filed on Mar. 7, 2019.

(30) Foreign Application Priority Data

Mar. 22, 2018 (JP) .................. 2018-055033
Mar. 22, 2018 (JP) .................. 2018-055034

(51) Int. Cl.
*G06K 9/62* (2022.01)
*G06F 3/01* (2006.01)
(Continued)

(52) U.S. Cl.
CPC ............ *G06F 3/013* (2013.01); *G06T 7/20* (2013.01); *G06V 40/18* (2022.01); *G06V 40/20* (2022.01); *G06T 2207/30201* (2013.01)

(58) Field of Classification Search
CPC . G06T 7/20–7/292; G06T 2207/30041; G06V 40/16–40/179;
(Continued)

(56) References Cited

U.S. PATENT DOCUMENTS

| 10,537,244 B1* | 1/2020 | Barash .................. A61B 3/113 |
| 2010/0167623 A1 | 7/2010 | Eyzaguirre |
| 2014/0192325 A1* | 7/2014 | Klin ....................... A61B 3/113 |
| | | 351/209 |

FOREIGN PATENT DOCUMENTS

| CN | 101086600 A | 12/2007 |
| CN | 103885589 A | 6/2014 |

(Continued)

OTHER PUBLICATIONS

Lehmann et al., "Physiologically Inspired Blinking Behavior for a Humanoid Robot", Springer-Verlag Berlin Heidelberg 2011, 11 pages. (Year: 2011).*

(Continued)

*Primary Examiner* — Brian Werner
(74) *Attorney, Agent, or Firm* — ROSSI, KIMMS & McDOWELL LLP

(57) ABSTRACT

A processing device includes a memory configured to store executable instructions, and processing circuitry configured to execute the executable instructions stored in the memory to thereby realize: a first acquisition unit configured to acquire timing of blink motion performed by a dialogue device, a second acquisition unit configured to acquire blink timing by user performing a dialogue with the dialogue device, and a processing unit configured to perform processing according to difference between the timing of blink motion performed by the dialogue device and the blink timing by the user.

13 Claims, 49 Drawing Sheets

(51) Int. Cl.
G06T 7/20 (2017.01)
G06V 40/18 (2022.01)
G06V 40/20 (2022.01)

(58) Field of Classification Search
CPC ..... G06V 40/18–40/197; G06V 20/597; A61B 3/113; A61B 5/1103; G06F 3/013; B25J 19/023
See application file for complete search history.

(56) References Cited

FOREIGN PATENT DOCUMENTS

| | | |
|---|---|---|
| CN | 105229563 A | 1/2016 |
| EP | 1786112 A2 | 5/2007 |
| JP | H10207615 A | 8/1998 |
| JP | H10293860 A | 11/1998 |
| JP | 2000349920 A | 12/2000 |
| JP | 2005142975 A | 6/2005 |
| JP | 2006020131 A | 1/2006 |
| JP | 2006120134 A | 5/2006 |
| JP | 2008072739 A | 3/2008 |
| JP | 2009037050 A | 2/2009 |
| JP | 2009267445 A | 11/2009 |
| JP | 2010525848 A | 7/2010 |
| JP | 2013154458 A | 8/2013 |
| JP | 5639440 B2 | 12/2014 |
| JP | 5771127 B2 | 8/2015 |
| JP | 2017153887 A | 9/2017 |
| JP | 2018015843 A | 2/2018 |
| KR | 100813668 B1 | 3/2008 |
| KR | 1020080057400 A | 6/2008 |
| KR | 1020120124772 A | 11/2012 |

OTHER PUBLICATIONS

Metta et al., "The iCub humanoid robot: An open-systems platform for research in cognitive development", Elsevier, Neural Networks 23 (2010) 1125-1134. (Year: 2010).*
Tatsukawa et al., "Eyeblink Synchrony in Multimodal Human-Android Interaction", Scientific Reports, Dec. 23, 2016, pp. 1-8. (Year: 2016).*
Notice of Allowance issued in Korean Appln. No. 10-2020-7030046 dated Feb. 25, 2023. English machine translation provided.
Office Action issued in Japanese Appln. No. 2022-014985 dated Apr. 4, 2023. English machine translation provided.
Nakano, "Synchronization of spontaneous eyeblinks while viewing video stories", Proceedings of the Royal Society B, Biological Sciences, 276 (1673), pp. 3635-3644, 2009. <URL:http://rspb.royalsocietypublishing.org/content/royprsb/early/2009/07/24/rspb.2009.0828.full.pdf.>[retrieval date: Mar. 12, 2018]. Cited in the specification.
Nakano, "Eyeblink entrainment at breakpoints of speech", Experimental Brain Research, 205(4), pp. 577-581, 2010. <URL:https://www.ncbi.nlm.nih.gov/pubmed/20700731> [retrieval date: Mar. 12, 2018]. Cited in the specification.
Tatsukawa, "Eyeblink Synchrony in Multimodal Human-Android Interaction", Scientific Reports, 6:39718, pp. 1-8, 2016. <URL:https://www.nature.com/articles/srep39718> [retrieval date: Mar. 12, 2018]. Cited in the specification.
Wiseman, "Blink and you'll miss it: the role of blinking in the perception of magic tricks", PeerJ,e1873, 2016. <URL:https://peerj.com/articles/1873/?tm#source=TrendMD&utm#campaign=PeerJ#TrendMD#1&utm#medium=TrendMD> [retrieval date: Mar. 12, 2018]. Cited in the specification.
International Search Report issued in International Application No. PCT/JP2019/009115 dated May 21, 2019. English translation provided.
Written Opinion issued in International Application No. PCT/JP2019/009115 dated May 21, 2019. English translation provided.
Takashima, "Effects of Character's Blinking Rate on Humans' Impressions", Proceedings of IPSJ Interaction 2008, Mar. 4, 2008. <URL:http://www.interaction-ipsj.org/archives/paper2008/oral/0034/paper0034.pdf>. Cited in NPL 5 and 6. English machine translation provided.
Nakano, "A New Role of the default mode network Revealed by Eyeblink", Japanese Journal of Physiological Psychology and Psychophysiology, vol. 31, No. 1, 2013, Japanese Society for Physiological Psychology and Psychophysiology, Jan. 7, 2014. <URL:https://www.jstage.jst.go.jp/article/jjppp/31/1/31_1303si/_article/-char/ja.> [retrieval date: May 8, 2019]. Cited in NPL 5 and 6. English machine translation provided.
Office Action issued in Korean Appln. No. 10-2020-7030046 dated Aug. 22, 2022. English translation provided.
"Read mental state with the number of 'eye blinks'" The JoongAng. URL: https://www.joongang.co.kr/article/2226879 [Search: Aug. 19, 2022], [Publication: Mar. 18, 1988]. Cited in NPL 1. English translation provided.
Lim. "A Study on The Expression of Digital Eye Contents for Emotional Communication." Journal of Digital Convergence. 2017: 563-571. vol. 15, No. 12. Partial English translation provided.
Office Action issued in Chinese Appln. No. 201980020916.4 dated Nov. 29, 2023. English machine translation provided.

* cited by examiner

FIG. 46
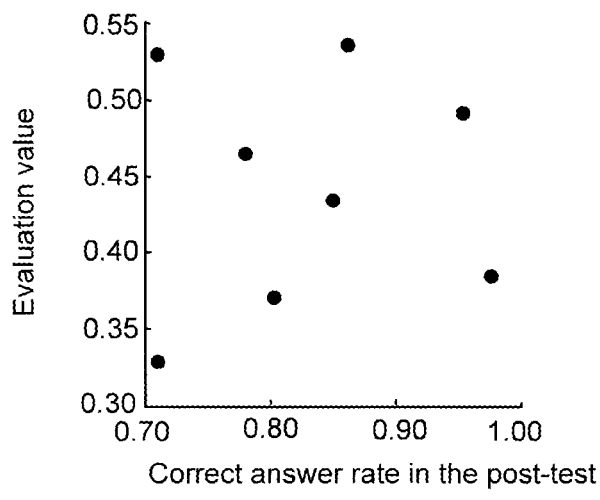
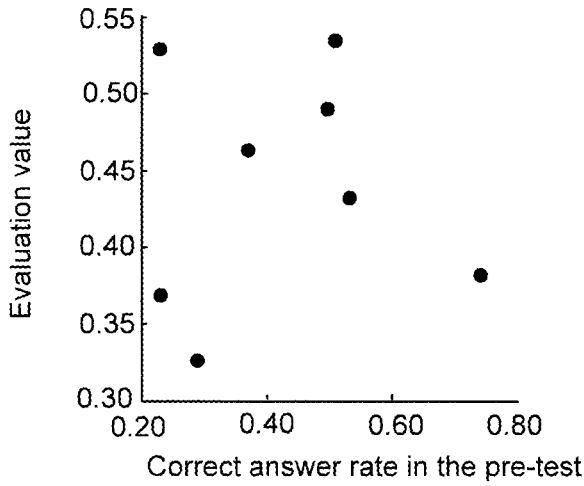
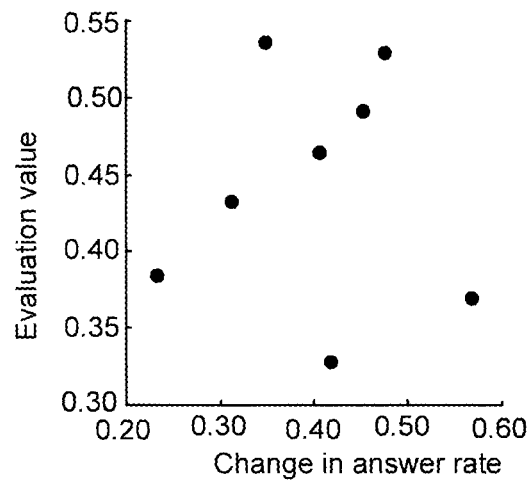

DEVICE AND METHOD TO ACQUIRE TIMING OF BLINK MOTION PERFORMED BY A DIALOGUE DEVICE

CROSS REFERENCE TO RELATED APPLICATIONS

This application is based upon and claims the benefit of priority from the prior Japanese Patent Application No. 2018-055033, filed on Mar. 22, 2018, the prior Japanese Patent Application No. 2018-055034, filed on Mar. 22, 2018, and PCT Application No. PCT/JP2019/009115 filed on Mar. 7, 2019, the entire contents of which are incorporated herein by reference.

FIELD

The present disclosure relates to a technique for utilizing a human blinking behavior to monitor human interest and enhance communication with artificial agents.

BACKGROUND

People spontaneously blink their eyes every 3 seconds on average. Currently, elucidation of this spontaneous blinks underway. The paper: Tamami Nakano, Yoshiharu Yamamoto, Keiichi Kitajo, Toshimitsu Takahashi and Shigeru Kitazawa, "Synchronization of spontaneous eyeblinks while viewing video stories", Proceedings of the Royal Society B: Biological Sciences, 276 (1673), p 3635-3644, [online], [Searched on Mar. 12, 2018], Internet <URL: http://rspb.royalsocietypublishing.org/content/royprsb/early/2009/07/24/rspb 2009.0828. full.pdf>, (2009) reveals that blink timings are synchronized between peoples while watching a video story, and those are not synchronized while watching an environmental video or listening to voice.

SUMMARY

An embodiment of the present disclosure provides a processing device including a first acquisition unit configured to acquire timing of blink motion performed by a dialogue device, a second acquisition unit configured to acquire blink timing by user of the dialogue device, and a processing unit configured to perform processing according to difference between the timing of blink motion performed by the dialogue device and the blink timing by the user.

In the processing device, the processing unit may perform processing according to index based on the difference.

In the processing device, the processing unit may perform a processing according to the degree to which the blink timing by the user is included within a predetermined period after the timing of the blink motion.

In the processing device, the predetermined period may include a time point of 500 milliseconds or less from the timing of the blink motion performed by the dialogue device.

In the processing device, the processing unit may perform the processing according to the difference between the blink timing by the user and the timing of blink motion performed by the dialogue device arranged in time order on a predetermined time axis and difference between the blink timing by the user and the timing of blink motion performed by the dialogue device when the order of at least one of the blink of the user and the blink motion is changed on the predetermined time axis.

In the processing device, the processing unit may cause the dialogue device to perform dialogue processing according to the difference.

In the processing device, the processing unit may output evaluation data according to the difference in association with identifier of the dialogue device.

The processing device further may include an environment information acquisition unit configured to acquire environment information indicating peripheral environment of the dialog device, and a blink motion control unit configured to cause the dialogue device to perform blink motion at first timing according to the environment information.

The processing device further may include a storage control unit configured to store in a storage device data associating the blink timing by the user with the environment. The blink motion control unit may set the first timing to a timing according to data accumulated in the storage device and the environment information.

In the processing device, the blink motion control unit further may cause the dialogue device to perform a blink motion at second timing different from the first timing.

The processing device further may include an eyelid unit corresponding to eyelid and a blink motion control unit configured to control the blink motion performed by the eyelid unit by opening and closing the eyelid unit. The first acquisition unit may acquire timing of the blink motion performed by the eyelid unit.

The processing device according further may include a display unit, and a blink motion control unit configured to control blink motion performed by object displayed on the display unit. The first acquisition unit may acquire timing of the blink motion performed by the object.

An embodiment of the present disclosure provides a processing method including acquiring timing of blink motion performed by a dialogue device and blink timing by user of the dialogue device, and processing according to difference between the timing of the blink motion performed by the dialogue device and the blink timing by the user.

An embodiment of the present disclosure provides a non-transitory computer readable storage medium storing program for causing a computer to execute acquiring timing of blink motion performed by a dialogue device and blink timing by user of the dialogue device and processing according to the difference between the timing of the blink motion performed by the dialogue device and the blink timing by the user.

An embodiment of the present disclosure provides a data processing device including an acquisition unit configured to acquire data indicating blink timing by user, a calculation unit configured to calculate an index according to synchronization degree of blink timings of a plurality of users based on the difference between the blink timings of the plurality of users, and an output unit configured to output data according to the index.

An embodiment of the present disclosure provides a data processing system including a blink detection unit configured to detect blink of user, and the data processing device.

An embodiment of the present disclosure provides a data processing method including acquiring data indicating blink timing by user, and calculating an index according to synchronization degree of blink timings of a plurality of users based on difference in blink timings of the plurality of users.

An embodiment of the present disclosure provides a non-transitory computer readable storage medium storing program for causing a computer to execute acquiring data indicating blink timings of user, and calculating an index according to synchronization degree of blink timings of a plurality of users based on difference in blink timings of the plurality users.

According to an embodiment of the present disclosure, it is possible to provide an applied technique using a blink motion.

BRIEF DESCRIPTION OF THE DRAWINGS

FIG. 46 is graphs illustrating relationships between a correct answer rate of questions, an understanding degree of questions and evaluation values according to the fifth embodiment of the present disclosure;

DESCRIPTION OF EMBODIMENTS

Figure 1:
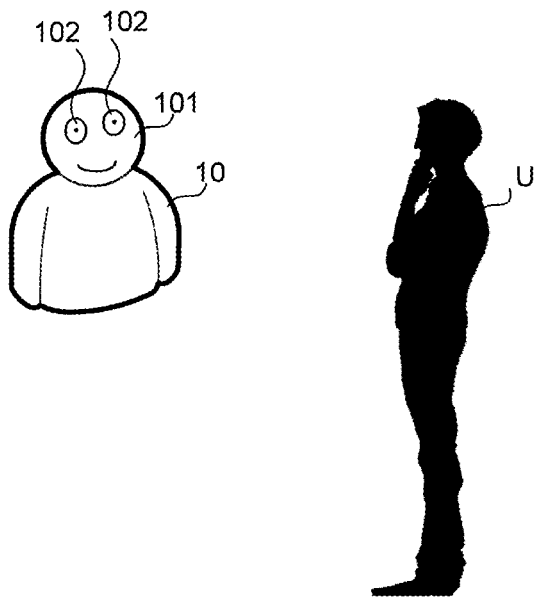
FIG. 1 is a diagram illustrating an external configuration of a dialogue device according to first embodiment of the present disclosure.

Hereinafter, an embodiment of the present disclosure will be described in detail with reference to the drawings. The embodiments illustrated below are examples of embodiments of the present disclosure, and the present disclosure is not limited to these embodiments. In the drawings referred to in the present embodiment, the same portions or portions having similar functions are denoted by the same reference numerals or similar reference numerals (only A, B, etc. are denoted after numerals), and a repetitive description thereof may be omitted.

On the other hand, the application of the blinking phenomenon is at the examination stage at present, and it has not yet reached the practical application.

It is therefore an object of the present disclosure to provide an applied technique using a blink motion.

First Embodiment

Techniques for realizing pseudo-communication between people and a dialogue device (hereinafter, simply referred to as "communication") have been proposed from the past. Japanese Laid-Open Patent Application Publication No. 2010-525848 discloses a dialogue type toy. A dialogue device which performs motion that imitates the blink of an eye has been proposed. Japanese Patent. No. 5,639,440 discloses that the eyes of a CG character are opened and closed at a predetermined blink interval. Japanese Unexamined Patent Application Publication No. 2000-349920 discloses a robot that performs blink motion at a timing that is exponentially distributed over time, with a timing of a head nod motion as a starting point. With respect to blinks of speaker and listener, the inventors disclose the following matters in papers 1 (Tamami Nakano and Shigeru Kitazawa, "Eyeblink entrainment at breakpoints of speech," Experimental Brain Research, 205(4), p. 577-81, [online], [Searched on Mar. 12, 2018], Internet <URL: https://www.ncbi.nlm.nih.gov/pubmed/20700731>, (2010)) and paper 2 (Kyohei Tatsukawa, Tamami Nakano, Hiroshi Ishiguro and Yuichiro Yoshikawa, "Eyeblink Synchrony in Multimodal Human-Android Interaction," Scientific Reports, 6: 39718, [online], [Searched on Mar. 12, 2018], Internet <URL: https://www.nature.com/articles/srep39718>, (2016).

Paper 1 discloses that blinks of a speaker and a listener are synchronized with a time delay. Paper 1 discloses that the blink of the speaker increases at the end of the story or between utterances. Paper 2 discloses that blinking is synchronized with a time delay between a speaker who is a robot and a listener who is a human.

In this case, regardless of the communication between the user and the dialogue device, even if the dialogue device performs blink motions, it may be difficult to contribute to an improvement of quality of communication.

In the first to third embodiments, examples of supporting communications between the dialogue device and the user using a blink motion will be described.

The inventors have got the knowledge that differences in the timing of the blinks of a speaker and a listener can be used to evaluate the quality of the communication performed by the speaker and the listener. For example, if the synchronization degree of the timing of blinks by the speaker and the listener is high, it can be inferred that the listener shows high interest in the speaker's speech. On the other hand, when the synchronization degree is low, it can be inferred that the listener is not so interested in the speech of the speaker.

Verification leading to such knowledge will be described later. Embodiments in which such knowledge is applied to a technique for realizing communications between the dialogue device and its users will be described below.

FIG. 1 is a diagram illustrating an exemplary external configuration of a dialogue device 10 according to first embodiment of the present disclosure. The dialogue device 10 is a processing device that perform the dialogue with user U. The user U is a user of the dialogue device 10. The user U faces the dialogue device 10 and communicate with the dialogue device 10 by dialogue.

The dialogue device 10 is a robot having an appearance imitating living things. The dialogue device 10 has, for example, an appearance imitating a human or another animal (e.g., a dog or a cat) or an imaginary person (e.g., an animated character). The external appearance of the dialogue device 10 is not limited.

The dialogue device 10 includes a face unit 101 and an eyelid unit 102. The face unit 101 is a part corresponding to the face. The eyelid unit 102 is a part arranged on the face unit 101 and corresponds to the eyelid of the eye. The eyelid unit 102 performs a motion imitating the blink of the eyes by opening and closing (hereinafter referred to as "blink motion"). In the present embodiment, two eyelid units 102 perform the same motion.

Figure 2:
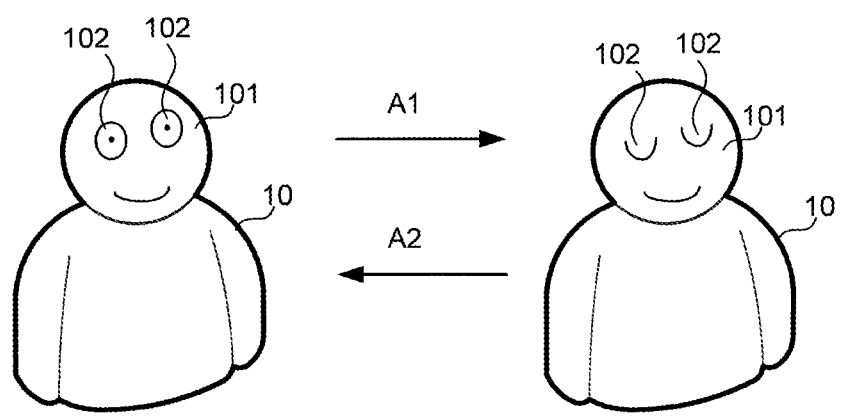
FIG. 2 is a diagram illustrating the blink motion performed by the dialogue device according to the first embodiment of the present disclosure.

FIG. 2 is a diagram illustrating the blink motion performed by the dialogue device 10. The dialogue device 10 keeps the eyelid unit 102 opens in normal times. The dialogue device 10 causes the eyelid unit 102 to transit from an open state to a closed state (arrow A1) and from the closed state to the open state (arrow A2) at the timing of blink motion. Timing of transition of the eyelid part 102 from the open state to the closed state and from the closed state to the open state is predetermined so that the eyelid unit 102 makes motion imitating the blink of the eye.

The dialogue device 10 may have a mouth, a nose, and other parts on the face unit 101. The dialogue device 10 may further perform motion of these parts arranged in the face unit 101, but explains thereof are omitted in the present embodiment.

The location and an application of the dialogue device 10 are not particularly limited. The dialogue device 10 may be located, for example, in a commercial facility, such as a store, a public facility, or another facility. In this case, the user U is a user of the facility. The dialogue device 10 may be used in a medical, toy, or other applications.

Figure 3:
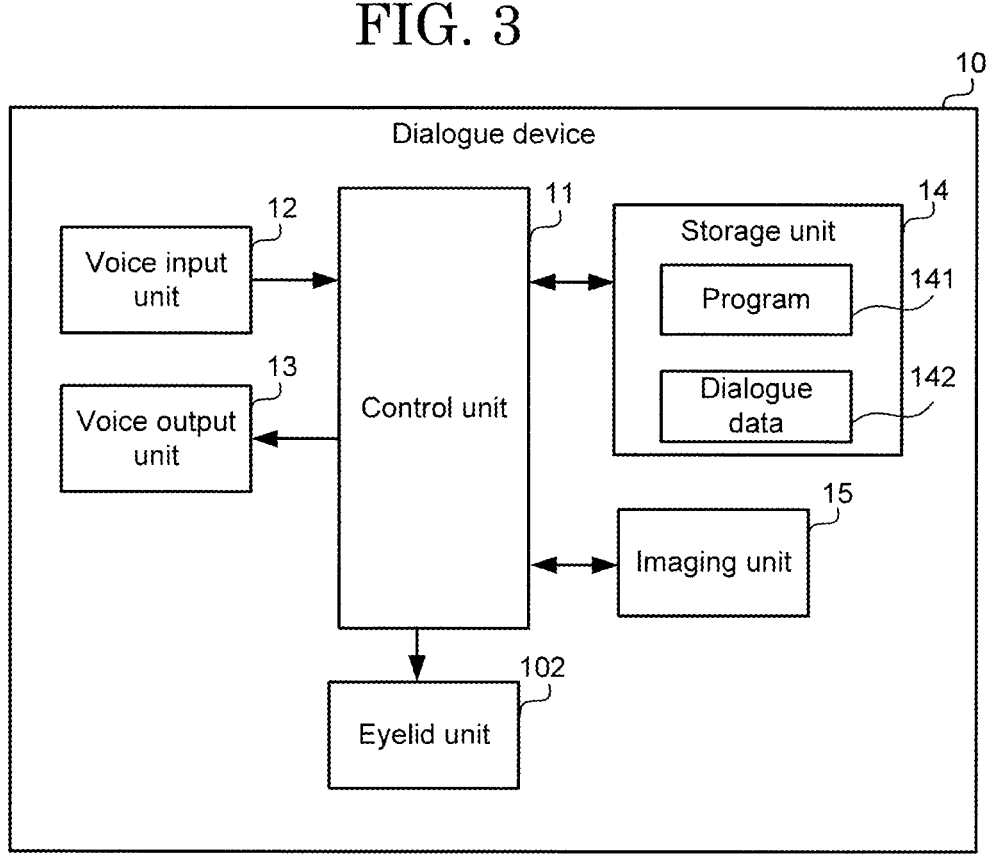
FIG. 3 is a block diagram illustrating a hardware configuration of the dialogue device according to the first embodiment of the present disclosure.

FIG. 3 is a block diagram illustrating a hardware configuration of the dialogue device 10. The dialogue device 10 has a control unit 11, a voice input unit 12, a voice output unit 13, a storage unit 14, an imaging unit 15, and the eyelid unit 102. The control unit 11 controls each unit of the dialogue device 10. The control unit 11 includes, for example, calculation processing devices exemplified by CPUs, and memories. The memory includes, for example, a RAM used by a calculation processing device as a work area and a ROM for storing a control program.

The voice input unit 12 receives voice inputs. The voice input unit 12 converts the received sound into a sound signal, and supplies the sound signal to the control unit 11. The voice input unit 12 includes, for example, a microphone, A (Analog)/D (Digital) converter circuit, and filters.

The voice output unit 13 outputs voice. The voice output unit 13 outputs the converted sound from the voice signal supplied from the control unit 11. The voice output unit 13 includes, for example, D/A converter circuit, and a speaker.

The storage unit 14 stores a data. The storage unit 14 stores, for example, a program 141 and a dialogue data 142.

The program 141 is a program for causing the control unit 11 to realize a predetermined function.

The dialogue data 142 is a data for the dialogue device 10 to perform a dialogue with the user U. The dialogue data 142 stores, for example, a plurality of data associated with an input data and an output data. The input data is data representing the contents of the utterance assumed to be uttered by the user U in a character string. The output voice is data representing the contents of the response to the utterance in a character string. For example, when the input data is "Name?", the output data associated with the input data is "My name is XX" ("XX" is the name of the dialogue device 10).

The dialogue data 142 may include an identifier that identifies the topic in association with the input and output data. For example, the first identifier "ID001" is associated with the input data and the output data used for speech related to soccer. The second identifier "ID002" is associated with the input data and output data used for speech related to meals.

The dialogue data 142 may be another type of data. The storage unit 14 may include any type of recording medium (storage device), for example, an optical recording media, a magnetic recording media, and a semiconductor recording media.

The imaging unit 15 captures an image of a subject, and generates an imaging data indicating the captured image. The subject is the user U. The imaging unit 15 includes, for example, an imaging device exemplified by a CCD (Charge Coupled Device) image sensor, and lenses. The lenses of the imaging unit 15 are provided, for example, in the vicinity of the eyelid unit 102 in the face unit 101, but may be provided in other positions in the face unit 101 or in positions except the face unit 101.

The eyelid unit 102 is opened and closed according to the control of the control unit 11. The eyelid unit 102 includes, for example, an opening and closing mechanism (e.g., a diaphragm and a cylinder), and a driving circuit for driving the opening and closing mechanism. Various known techniques can be applied to the mechanisms for realizing the blink motion.

Figure 4:
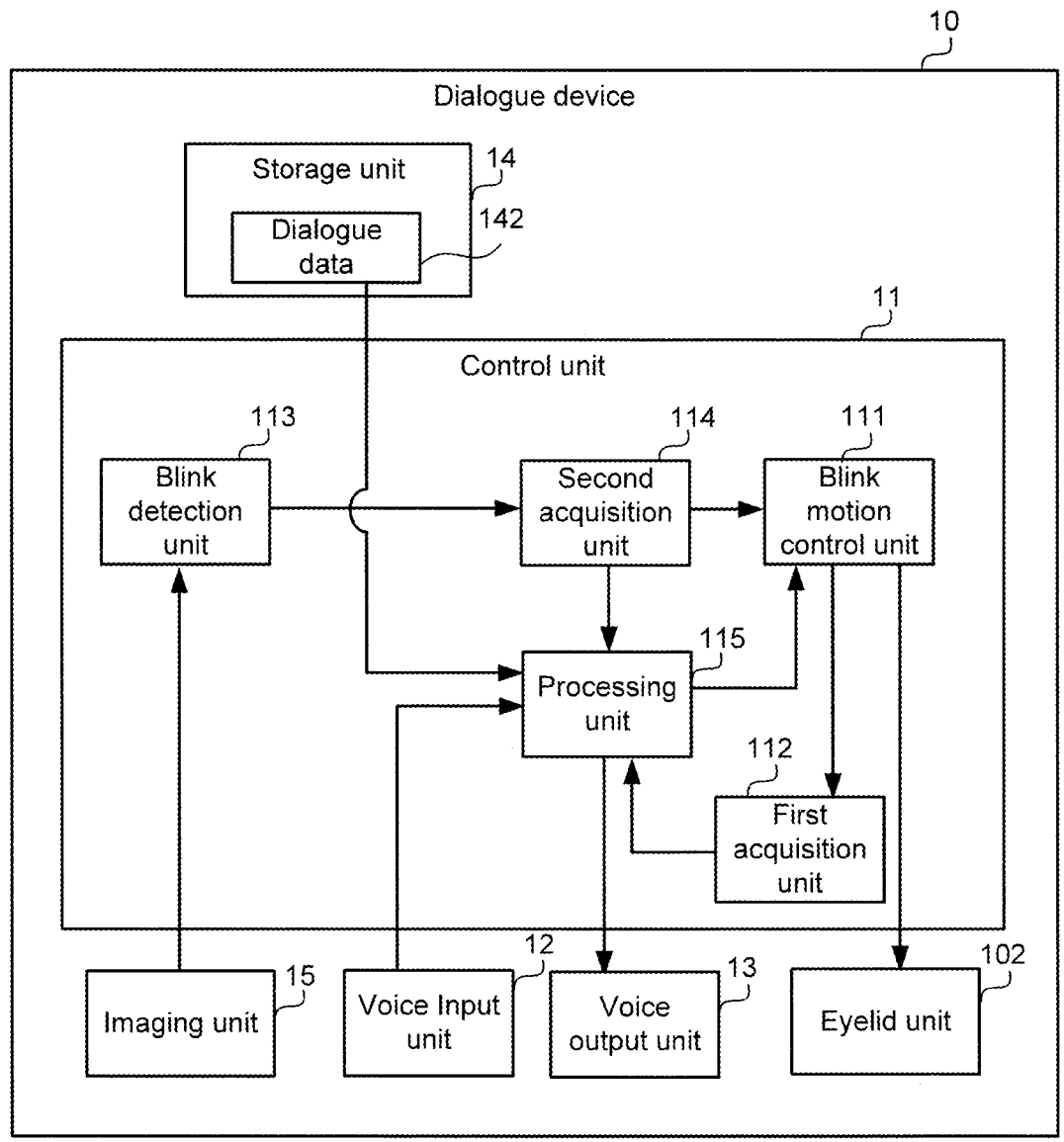
FIG. 4 is a block diagram illustrating a functional configuration of the dialogue device according to the first embodiment of the present disclosure.

FIG. 4 is a block diagram illustrating a functional configuration of the dialogue device 10. The control unit 11 of the dialogue device 10 includes a blink motion control unit 111, a first acquisition unit 112, a blink detection unit 113, a second acquisition unit 114, and a processing unit 115. The control unit 11 realizes a function corresponding to the blink motion control unit 111, the first acquisition unit 112, the blink detection unit 113, the second acquisition unit 114, and the processing unit 115 by executing the program 141. The control unit corresponds to the above-mentioned processor.

The blink motion control unit 111 controls the blink motion performed by the dialogue device 10 by opening and closing the eyelid unit 102. The blink motion control unit 111 outputs, for example, a blink control data for blink motion to the eyelid unit 102. The eyelid unit 102 opens and closes according to the blink control data. The blink motion control unit 111 may not necessarily be included in the control unit.

The first acquisition unit 112 acquires the timing of the blink motion performed by the dialogue device 10 (eyelid unit 102). The first acquisition unit 112 acquires, for example, a data indicating the timing of blink motion from the blink motion control unit 111.

The blink detection unit 113 detects the blink of the user U. Specifically, the blink detection unit 113 detects the blink of the user U based on an imaging data generated by the imaging unit 15. The blink detection unit 113 may not necessarily be included in the control unit 11.

The second acquisition unit 114 acquires a timing of the blink by the user U. In the present embodiment, the second acquisition unit 114 acquires a data indicating the timing of the blink by the user U (hereinafter referred to as "blink data"). The blink data is a data (first data) of the time at which the blink is detected, arranged in the order of the time. The second acquisition unit 114 generates the blink data based on, for example, a result of the blink data detected by the blink detection unit 113.

The processing unit 115 processes according to the difference between the timing of the blink motion performed by the dialogue device 10 and the blink timing by the user U. In the present embodiment, the processing unit 115 performs a dialogue processing. The dialogue processing is a processing for perform a dialogue using the dialogue data 142. Specifically, the dialogue processing includes a processing of recognizing a voice input through the voice input unit 12 and converting it into input data. The dialogue processing includes a processing of converting the output data associated with the input data into speech and outputting it through the voice input unit 12.

Figure 5:
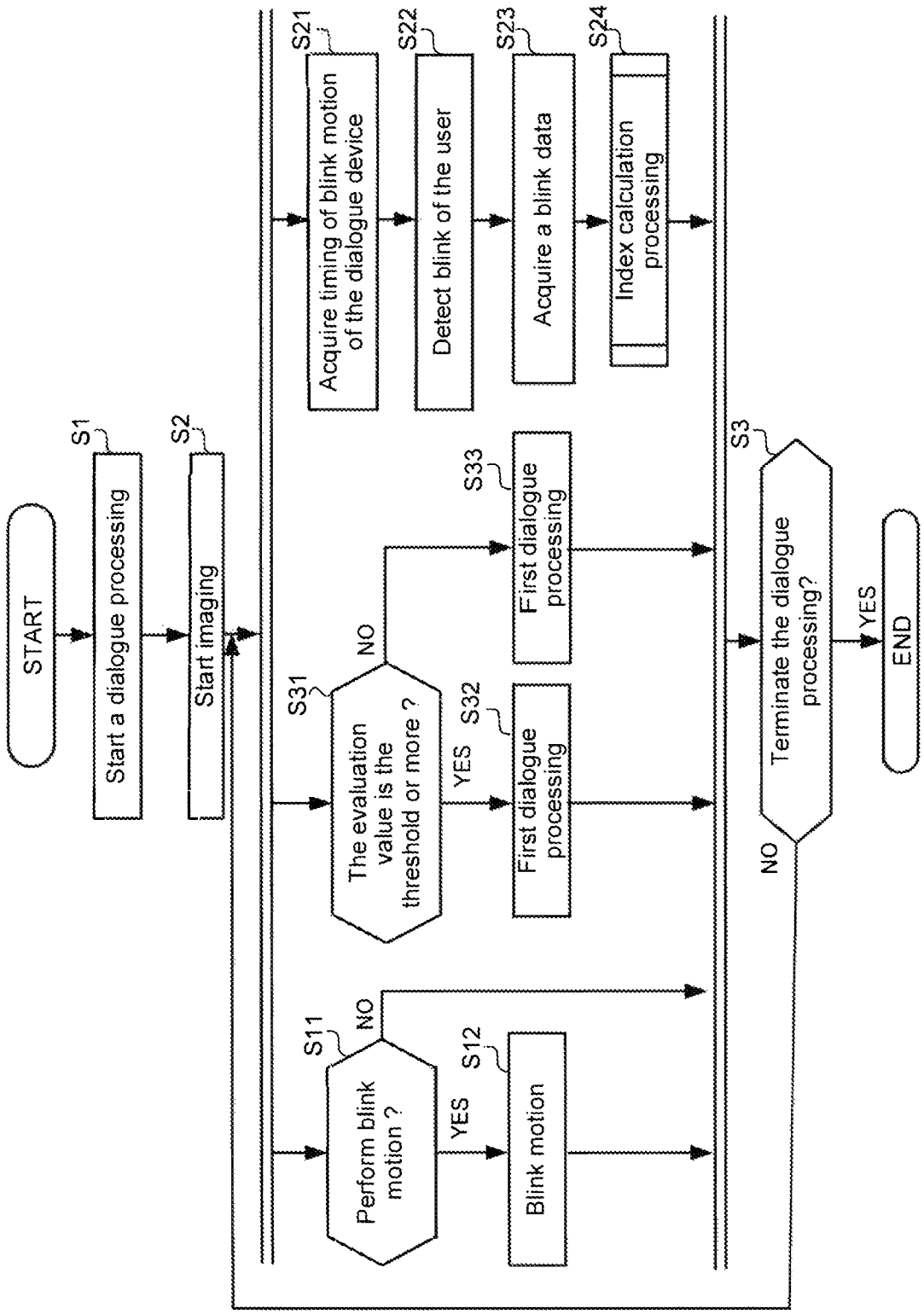
FIG. 5 is a flowchart illustrating a processing executed by the dialogue device according to the first embodiment of the present disclosure.

Next, a motion of the dialogue device 10 will be described. FIG. 5 is a flowchart illustrating a processing executed by the dialogue device 10.

In motion S1, the processing unit 115 starts a dialogue processing. The opportunity to start the dialog processing is not limited. The processing unit 115 may be timing when the presence of the user U is recognized. The user of the dialogue device 10 is, for example, a person recognized from an image indicated by the imaging data, a person located in an imaging direction of the imaging unit 15, or a person located in a position corresponding to a position of the imaging unit 15. The user of the dialogue device 10 may be a person who has logged in to the dialogue device 10. The processing unit 115 may initiate the dialogue processing when a predetermined voice (e.g., a voice indicating a greeting) is recognized from the voice entered via the voice input unit 12 or when a predetermined processing is accepted.

Next, in step S2, the processing unit 115 causes the imaging unit 15 to start imaging. When the imaging starts, the dialogue device 10 performs a processing described below.

First, the processing relating to the blink motion will be described. In step S11, the blink motion control unit 111 determines whether to perform blink motion. For example, the blink motion control unit 111 determines that the blink motion is to be performed during the utterance of the dialogue device 10 or when the utterance is completed. The timing at which the utterance ends is, for example, the timing at which the speech is interrupted. The timing of the blink motion may include a random timing.

If "YES" is determined in the step S11, the blink motion control unit 111 causes the dialogue device 10 to perform the blink motion (step S12). If "NO" is determined in step S11, the blink motion control unit 111 does not perform the blink motion. Then, the processing of the dialogue device 10 proceeds to S3.

Next, a processing of evaluating the quality of communications between the dialogue device 10 and the user is described.

The first acquisition unit 112 acquires the timing of the blink motion performed by the dialogue device 10 (step S21). Next, the blink detection unit 113 detects the blink of the user U based on the imaging data supplied from the imaging unit 15 (step S22). Various known techniques may be applied to the blink detection algorithm. For example, the blink detection unit 113 extracts a plurality of characteristic points along the periphery of the eye of the user U from the image indicated by a captured imaging data. The blink detection unit 113 extracts a characteristic point based on, for example, Haar-like. The blink detection unit 113 detects a presence or absence of blink of the user U by specifying a direction of movement of an extracted feature point and a temporal change of its velocity based on the imaging data of a plurality of frames. For example, due to human blinking, a rapid change in the velocity of the feature point occurs between approximately 0 to 300 milliseconds. Therefore, the blink detection unit 113 detects that there is a blink of the user U when the velocity change within a predetermined period becomes equal to or greater than the threshold value.

Next, the second acquisition unit 114 acquires a blink data indicating the blink timing by the user U based on a result of detecting a blink (step S23).

Next, the processing unit 115 performs an index calculation processing (step S24). The index calculation processing is a processing of calculating an index of the quality of communications between the dialogue device 10 and the user U.

Figure 6:
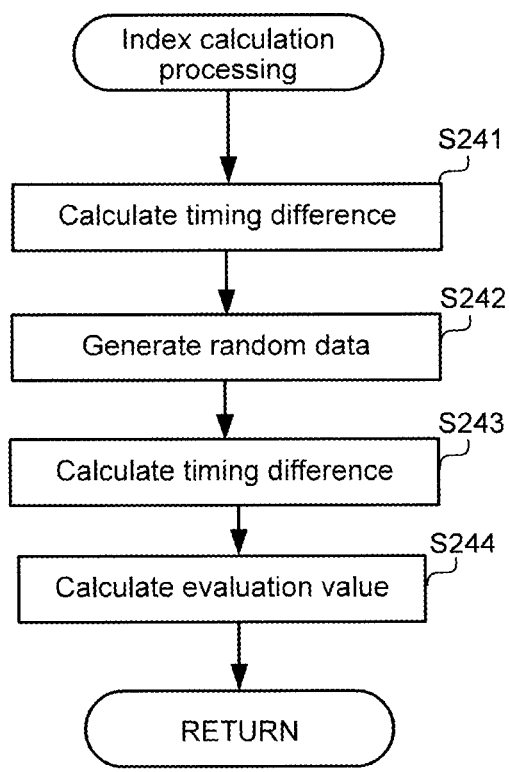
FIG. 6 is a flowchart illustrating an index calculation processing according to the first embodiment of the present disclosure.

FIG. 6 is a flowchart illustrating the index calculation processing. Hereinafter, the index calculation processing will be described with reference to specific examples.

First, the processing unit 115 calculates the difference between the blink timing by the user U and the timing of the blink motion performed by the dialogue device 10 (step S241). For example, the processing unit 115 calculates a difference (hereinafter, referred to as "timing difference") between all combinations of the blink timing by the user U and the timing of the blink motion performed by the eyelid unit 102 in a predetermined period. The predetermined period is, for example, 30 seconds, but may be less than 30 seconds or longer than 30 seconds. For example, the predetermined period is the entire period or a part of the period traced back a predetermined time period from the timing when the utterance of the dialogue device 10 ends.

Figure 7:
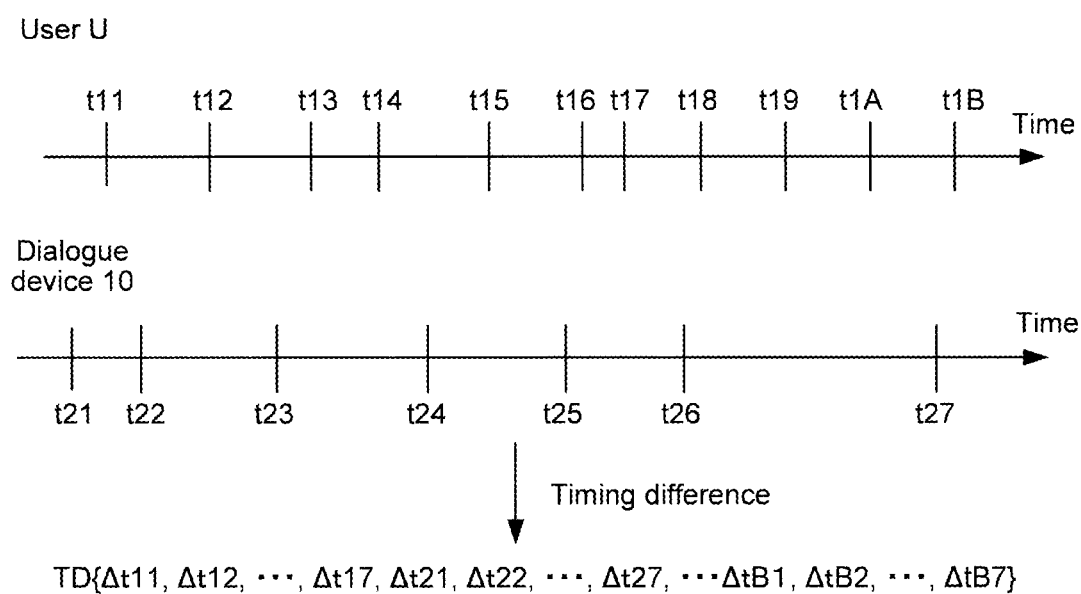
FIG. 7 is a diagram illustrating a method of calculating a timing difference according to the first embodiment of the present disclosure.

FIG. 7 is a diagram illustrating a method of calculating a timing difference. The timing chart in FIG. 7 illustrates the blink timing by the user U and the timing of the blink motion performed by the dialogue device 10. As illustrated in FIG. 7, the blink timing by the user U is represented by t11, t12, . . . , t1B in the order of time. The timing of the blink motion performed by the dialogue device 10 is represented by t21, t22, . . . , t27 in the order of the time. In this case, for each of t11, t12, . . . , t1B, the processing unit 115 calculates the difference from each of t21, t22, . . . , t27. The difference timing which is difference between the timing t1$i$ of the blink and the timing t2$j$ of the blink motion is hereinafter referred to as "Δt$ij$". In this case, the processing unit 115 calculates the timing difference TD{Δt11, Δt12, . . . , Δt17, Δt21, Δt22, . . . , Δt27, . . . , ΔtB1, ΔtB2, . . . , ΔtB7}.

Figure 8:
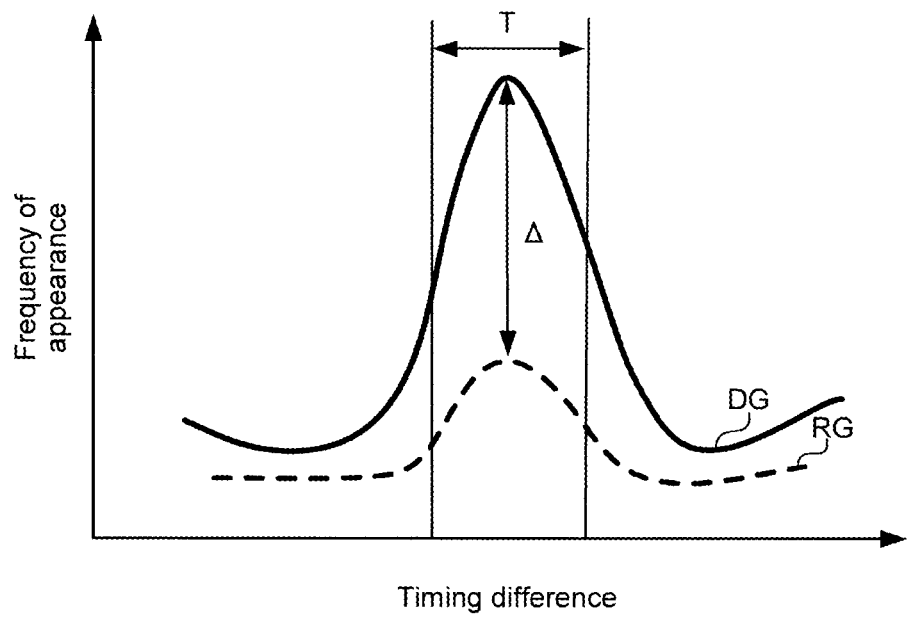
FIG. 8 is a graph illustrating a frequency distribution of the timing difference according to the first embodiment of the present disclosure.

FIG. 8 is a graph DG illustrating of the frequency distribution of the timing difference. In the graph DG of FIG. 8, the horizontal axis corresponds to the timing difference, and the vertical axis corresponds to the degree of appearance (i.e., frequency) of each timing difference. In the example illustrated in FIG. 8, the frequency of appearance is high within a certain time range T.

Incidentally, it is considered that the frequency distributions illustrated in the graphs DG are caused not only by communications between the user U and the dialogue device 10 but also by the blink characteristics (for example, the number and frequency) of the user U and the blink motion characteristics (for example, the number and frequency) of the dialogue device 10. For example, when the frequency of blink of the user U and the frequency of the blink motion performed by the dialogue device 10 are higher, the frequency of appearance of a smaller timing difference tends to be higher. Therefore, it is necessary to clarify to what extent the timing difference TD is caused by the communication between the dialog device 10 and the user U. The processing unit 115 analyzes the frequency distributions based on the surrogate data method.

The processing unit 115 generates random data (second data) (step S242). The random data includes data in which the order of the blinking intervals of the dialogue device 10 is randomly changed on the time axis.

Figure 9:
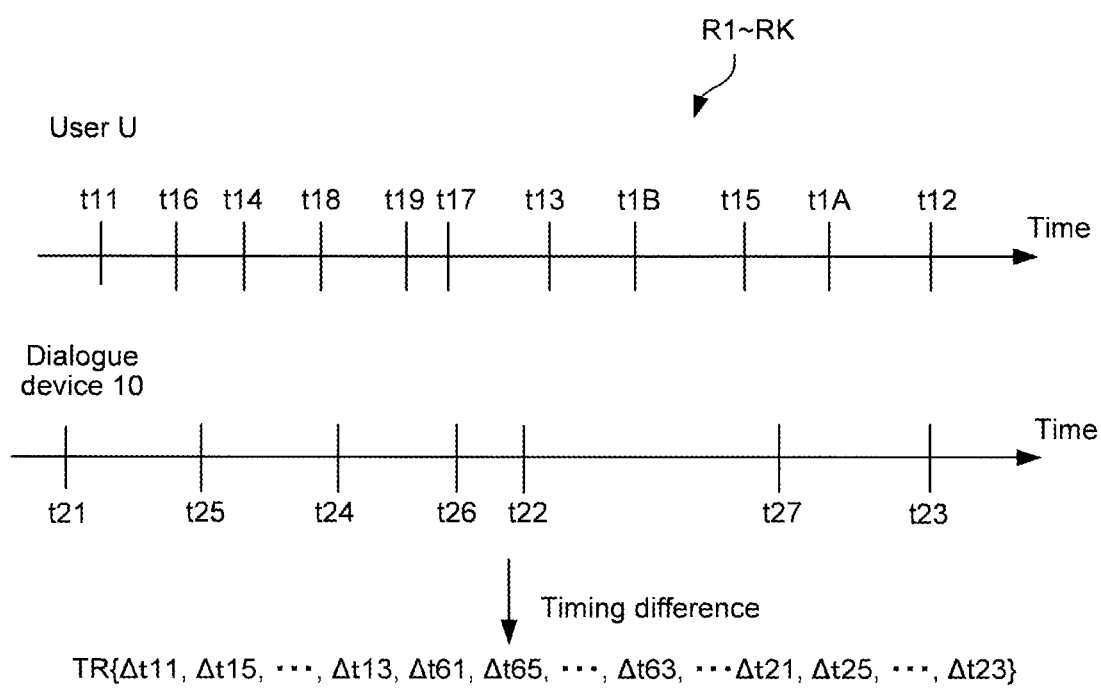
FIG. 9 is a diagram illustrating an example of random data according to the first embodiment of the present disclosure.

FIG. 9 is a diagram illustrating an example of the random data R1 to RK. The processing unit 115 generates K (e.g., 1000) pieces of the random data R1 to RK. In the random data R1 to RK illustrated in FIG. 9, the order of interval of the blink motion performed by the dialogue device 10 is changed, and the order of interval of the blink of the user U is not changed. The timing "t2j" illustrated in FIG. 7 corresponds to the timing "t2ja" illustrated in FIG. 9.

Next, the processing unit 115 calculates the timing difference, which is the difference between the blink timing by the user U and the timing of the blink motion performed by the dialogue device 10, for each of the generated random data (step S243). The timing difference may be calculated in the same manner as in step S241. The timing difference, which is the difference between the blink timing t1ia and the timing t2ja of the blink motion, is hereinafter referred to as "Δtija". In FIG. 9, the processing unit 115 calculates the timing difference TR {Δt11a, Δt15a, . . . , Δt13a, Δt21a, Δt25a, . . . , Δt23a, . . . , ΔtB1a, ΔtB5a, . . . , ΔtB3a} based on the random data. The frequency of the timing difference in the random data is indicated by, for example, the graph RG in FIG. 8. The graph RG illustrates the mean frequency of the timing differences of the random data R1-RK.

Next, the processing unit 115 calculates the evaluation value according to the timing difference based on the blink data and the timing difference based on the random data (step S244). The evaluation value is an index that is an index of the quality of communications between the dialogue device 10 and the user U. The random data is data obtained by randomly changing interval of the blink motion performed by the dialogue device 10. Therefore, the random data can be regarded as data in which time series data is lost while maintaining the number of times and interval of the blink motion performed by the dialogue device 10. That is, by comparing the distribution of the timing difference TDs with the distribution of the random data R1 to RK, it is possible to understand the degree to which the distribution of the appearance of the timing difference indicated by the blink data of the user U appears due to the communications between the dialogue device 10 and the user U.

The processing unit 115 calculates the evaluation value by the Z score. That is, the processing unit 115 subtracts the mean of the timing difference at random data R1-RK from each of timing difference TDs {Δt11, Δt12, . . . , Δt17, Δt21, Δt22, . . . , Δt27, . . . , ΔtB1, ΔtB2, . . . , ΔtB7} indicated by the blink data. In addition, the processing unit 115 divides the resulting value by the standard-deviation of the timing difference in the random data R1-RK. Hereby, the processing unit 115 calculates the evaluated values. For example, if the distribution of the timing difference TDs is the same as the distribution of the random data, the evaluation value is "0". In this instance, it is assumed that the blink of the user U is not affected by the communications between the dialogue device 10 and the user U. On the other hand, when the evaluation value is large and the difference between the distribution of the timing difference TDs and the distribution of the random data is large, it is assumed that the blink of the user U is affected by the communications between the dialogue device 10 and the user U. With reference to FIG. 8, it is assumed that the larger the difference A in the frequency of appearance is, the stronger the influence of communication is. Therefore, the evaluation value becomes large.

Figure 10:
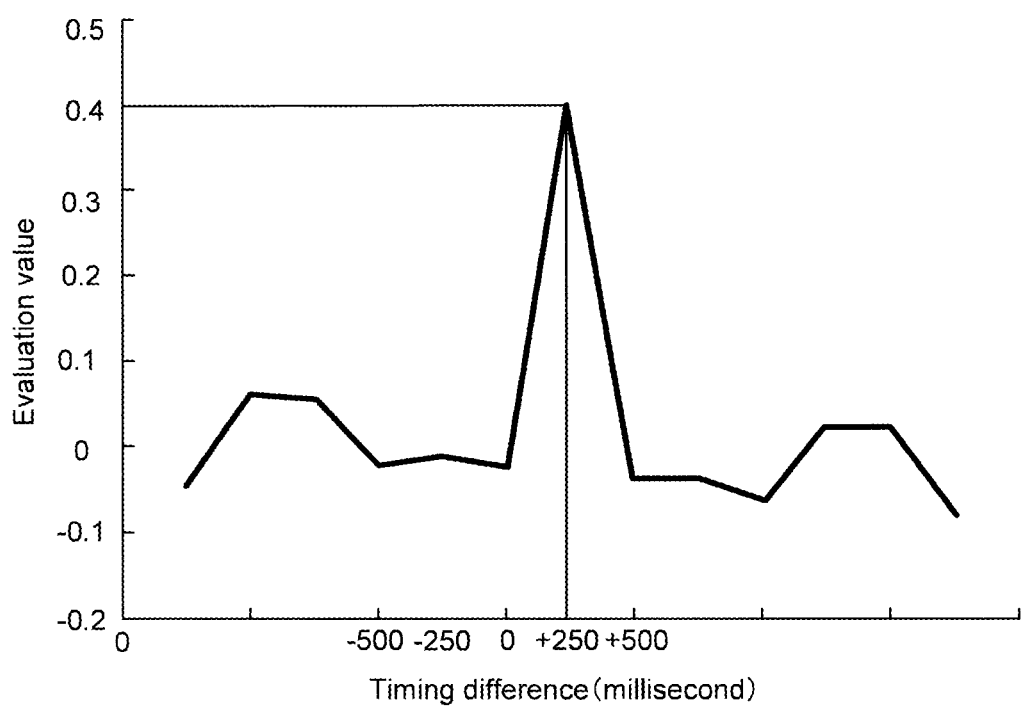
FIG. 10 is a diagram illustrating an example of an evaluation value according to the first embodiment of the present disclosure.

FIG. 10 is a graph illustrating an example of an evaluation value. In the graph illustrated in FIG. 10, the horizontal axis corresponds to the timing difference, the vertical axis corresponds to the evaluation value. If the timing difference is positive, it means that the blink timing by the user U is behind the timing of the blink motion performed by the dialogue device 10. If the timing difference is negative, it means that the blink timing by the user U is earlier than the timing of the blink motion performed by the dialogue device 10. The timing difference is represented here in 250 millisecond increments. In FIG. 10, the timing difference "0" millisecond indicates that timing difference is greater than or equal to 0 millisecond and less than 250 millisecond. The timing difference "+250" millisecond and "−250" millisecond indicate that the timing difference is greater than or equal to 250 millisecond and less than 500 millisecond. In this embodiment, the processing unit 115 calculates an evaluation value of the quality of communications between the dialogue device 10 and the user U based on the degree that the blink timing by the user U is included within a predetermined period after the timing of the blink motion performed by the dialogue device 10. Specifically, the processing unit 115 calculates an evaluation value corresponding to the timing difference "+250" milliseconds as an evaluation value of the quality of communications between the dialogue device 10 and the user U. That is, the processing unit 115 calculates the evaluation value based on the frequency of blinks in which the blink timing by the user U is delayed more than the timing of the blink motion performed by the dialogue device 10 and the timing difference is 250 milliseconds or more and less than 500 milliseconds. In the example illustrated in FIG. 10, the evaluation value is "0.4". The index calculation processing has been described above.

The random data may be data in which the order of the interval of the blink motion as to the dialogue device 10 is not changed, and the order of the interval of the blink as to the user U is changed. The random data may be data in which the order of interval of the blink motion as to the dialogue device 10 and the order of interval of the blink as to the user U are changed. When the index calculation processing is completed, the processing of the dialogue device 10 proceeds to step S3.

Next, returning to FIG. 5, a processing relating to the dialog processing will be described. The processing unit 115 determines whether the evaluation value calculated in the index calculation processing in step S24 is equal to or greater than the threshold (step S31). Here, the evaluation value is an evaluation value corresponding to the most recent period. The threshold is the index at which it is determined if the user U is interested in performing a dialogue with the dialogue device 10. The threshold is, for example, a predetermined value.

If "YES" is determined in the step S31, the processing unit 115 performs a first dialogue processing (step S32). If "NO" is determined in the step S32, the processing unit 115 performs a second dialogue processing that differs from the first dialog processing (step S33). In other words, the processing unit 115 performs various dialog processing depending on whether or not the evaluation value is equal to or larger than the threshold. When the evaluation value is equal to or greater than the threshold value, it is assumed that the user U is highly interested in communicating with the dialogue device 10. That is, the processing unit 115 performs, for example, the first dialogue processing that does not change the present topic. For example, if the processing unit 115 was having a dialogue with the user U about soccer, the processing unit 115 continues to have a dialogue about the soccer. In this case, the processing unit 115 performs the first dialogue processing based on the input data and the output data associated with identifier "ID001" included in the dialogue data.

On the other hand, when the evaluation value is less than the threshold, it can be inferred that the degree of interest in communication with the dialogue device 10 of the user U is low. Therefore, the processing unit 115 performs the second dialogue processing in which the present topic is changed. For example, if the processing unit 115 was performing a dialogue with the user U about soccer, the processing unit 115 changes to perform a dialogue about today's lunch. In this case, the processing unit 115 performs the second dialogue processing based on the input data and the output data associated with identifier "ID002" included in the dialogue data.

As described above, the processing unit 115 performs a processing according to the index (in this embodiment, the evaluation value) based on the difference between the timing of the blink motion performed by the dialogue device 10 and the blink timing by the user U. However, the first dialog processing and the second dialog processing described above are examples, and various modifications are possible. The processing unit 115 may continue the first dialog processing without performing the second dialog processing in which the topic of the dialog is changed as soon as the evaluation value becomes less than the threshold. In this case, when the period in which the evaluation value is less than the threshold continues for a predetermined period, or when the number of times in which the evaluation value becomes less than the threshold becomes equal to or more than a predetermined number of times, the processing unit 115 may change from the first dialogue processing to the second dialogue processing. Then, the processing of the dialogue device 10 may proceed to the step S3.

In the step S3, the processing unit 115 determines whether or not to terminate the dialogue processing. For example, if the processing unit 115 no longer recognizes the presence of the user U based on the imaging data supplied from the imaging unit 15, the processing unit 115 may determines that the dialogue processing is terminated. When the processing unit 115 recognizes a predetermined voice (for example, a voice indicating a farewell greeting) from the voice input through the voice input unit 12 or when the processing unit 115 receives a predetermined motion, the processing unit 115 may determine that the dialogue processing is terminated.

When the processing unit 115 determines to continue the dialogue processing (step S3; NO), the processing of the dialogue device 10 is returned to steps S11, S21, and S31. If the processing unit 115 determines that the dialogue processing is terminated (step S3; YES), the processing unit 115 terminates the dialogue processing.

According to the dialogue device 10, the degree of interest in communicating with the dialogue device 10 of the user U can be quantitatively evaluated according to the difference between the blink timing by the user U and the timing of the blink motion performed by the dialogue device 10. In addition, the dialogue device 10 can support communications between the dialogue device 10 and the user U by reflecting this assessment in the dialogue processing. The dialogue device 10 can evaluate the quality of communications based on the natural motion of blink of the user U. Therefore, according to the dialogue device 10, the evaluation can be performed without requesting the user U to perform motion required for the evaluation.

Here, the basis on which the difference between the blink timing by the user U and the timing of the blink motion performed by the dialogue device 10 can be used to evaluate the quality of communications will be explained. The inventors verified that the timing difference between the blink timing of the speaker and the blink timing of the listener is an index of the degree of interest in communicating between the speaker and the listener, in the manner described below.

The speaker is a demonstrator who is engaged in the performance sale of goods. The demonstrator introduced four products, "a hair dryer for women", "cosmetics for women", "a wristwatches for men", and "electric shavers for men". The introduction time of each product is about 3 minutes. The listener is a total of 38 university students, 18 males and 20 females. Thirty-eight listeners responded to whether they are interested in each of found product introduction after watching a video in which the speaker introduced the product. The timing difference of between the blink of the speaker and the blink of the listener was detected from videos of the speaker and the listener captured respectively. This allowed us to analyze the blink timing of the listener before and after the blink timing of the speaker.

Figure 11:
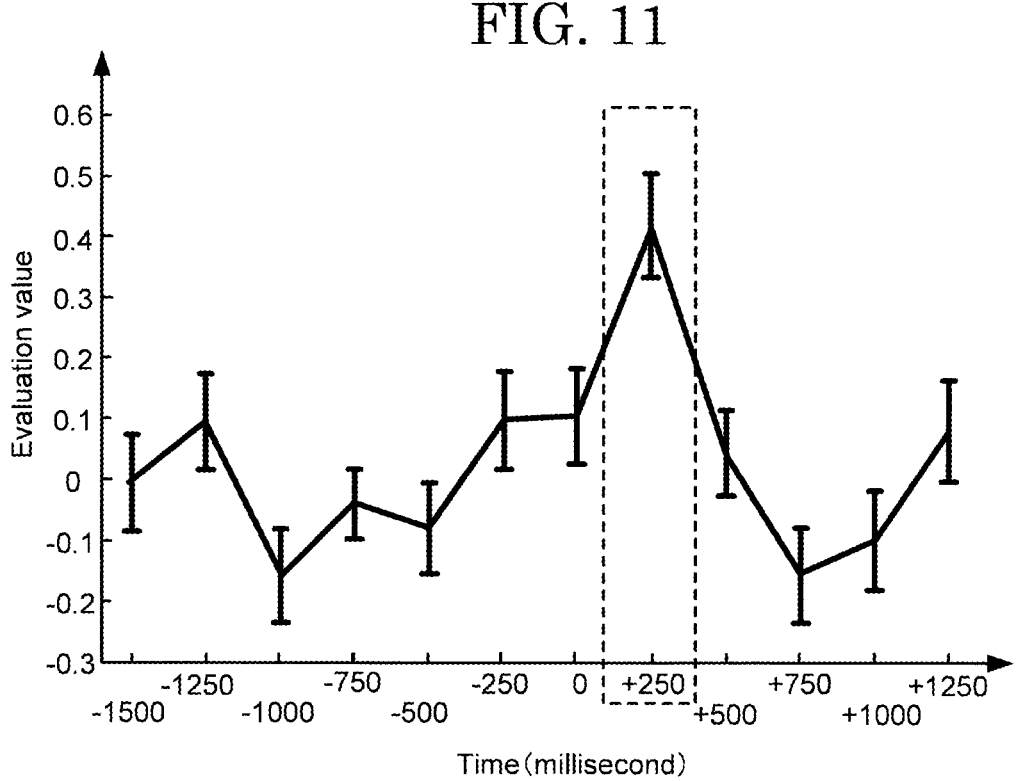
FIG. 11 is a graph illustrating the frequency distribution of the blink of a listener according to the verification of the first embodiment of the present disclosure.

FIG. 11 is a graph illustrating the frequency distribution of the blink of 38 listeners. In the graph illustrated in FIG. 11, the horizontal axis corresponds to the time, the vertical axis corresponds to the evaluation value (Z score). For the time, the blink timing of the speaker is set to "0". The blink timing of the listener earlier than "0" is indicated by a negative value. The blink timing of the listener later than "0" is indicated by a positive value. That is, the horizontal axis of the graph of FIG. 11 illustrates the timing difference. In FIG. 11, similarly to FIG. 10, the timing difference is represented in 250 milliseconds increments. In this verification, random data is used in such a manner that the order of interval of the blink of the speaker is changed and the order of interval of the blink of the listener is not changed in the calculation of the evaluation value. As illustrated in FIG. 11, the blink of the listener increased with a delay within a time range of +250 milliseconds or more and less than +500 milliseconds from the blink of the speaker, and the evaluation value increased. The p value is 0.000001.

Figure 12:
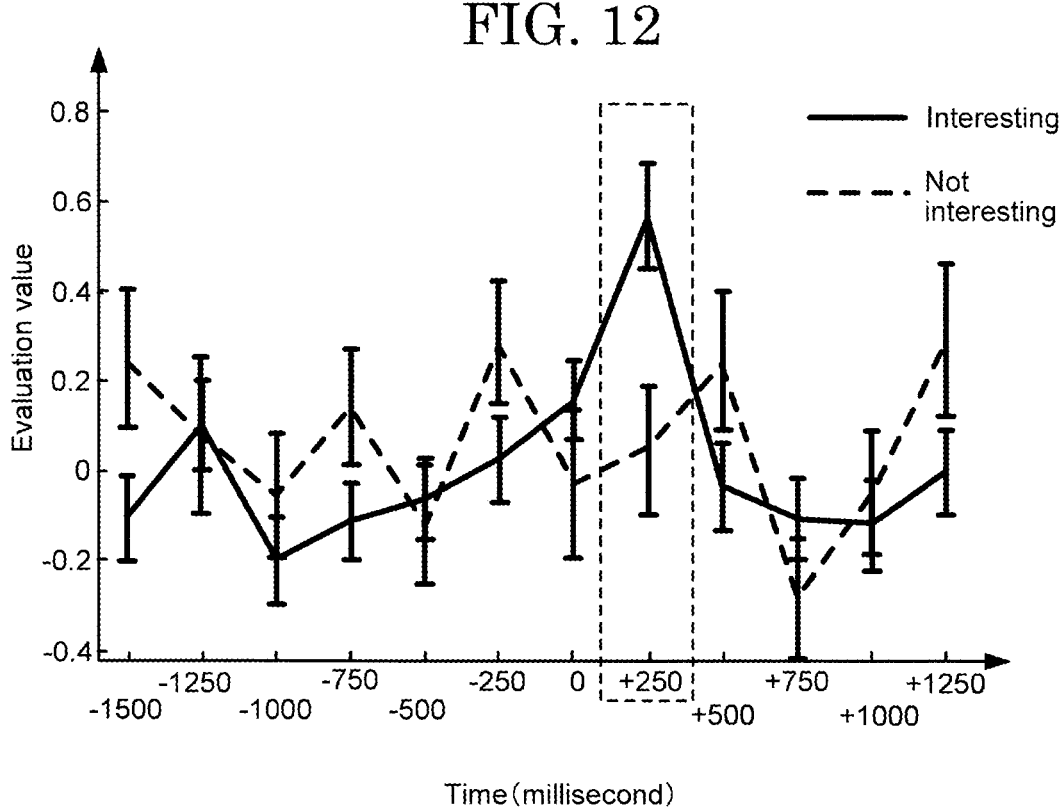
FIG. 12 is a graph illustrating the frequency distribution of the blink of the listener for each answer result according to the verification of the first embodiment of the present disclosure.

FIG. 12 is a graph illustrating the frequency distribution of the blink of the listener according the listeners' interest. In the graph illustrated in FIG. 12, similarly to FIG. 11, the horizontal axis corresponds to the time, the vertical axis corresponds to the evaluation value. The solid line graph illustrates the evaluation value of the listener who answered that the product introduction was interesting. The dashed line graph illustrates the evaluation value of the listener who answered that the product introduction was not interesting.

As illustrated in FIG. 12, for the listener who answered that the product introduction was interesting, the blink increased with a delay within a time range of +250 milliseconds or more and less than +500 milliseconds from the blink of the speaker, and the evaluation value increased. On the other hand, for the listener who answered that the product introduction was not interesting, such an increase in blinking and an increase in evaluation value was not confirmed. The p value is 0.004.

Figure 13:
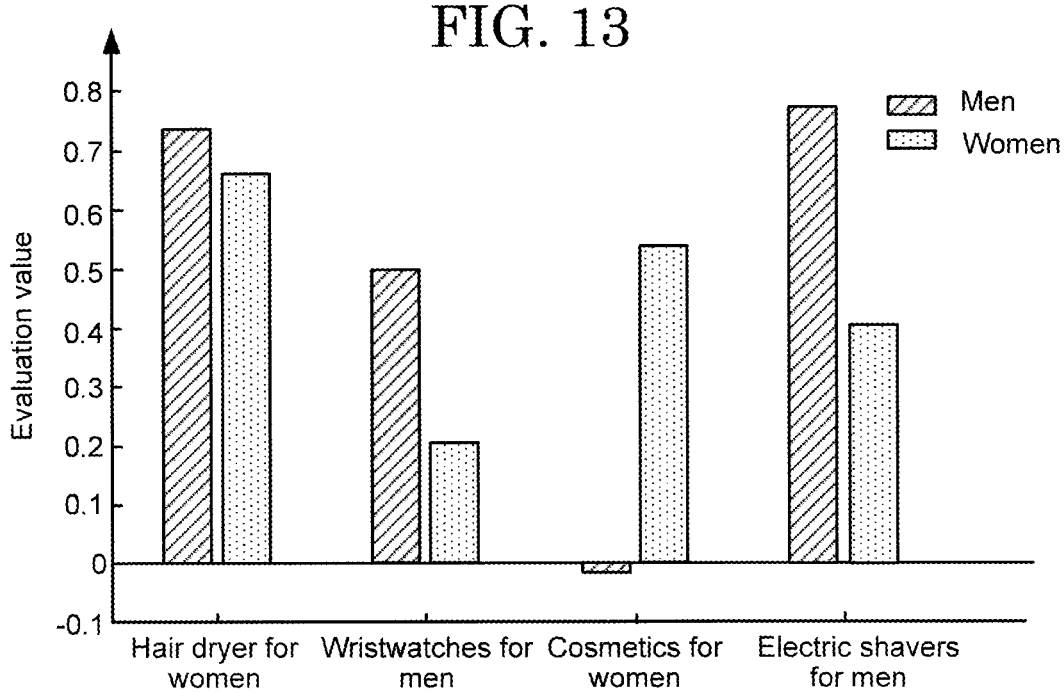
FIG. 13 is a graph illustrating evaluation values according to the verification of the first embodiment of the present disclosure by gender and product.

FIG. 13 is a graph illustrating evaluation values by gender of the listener and product. As illustrated in FIG. 13, the evaluation value for "cosmetics for women" is high for female listeners, but the evaluation value for male listeners is low. The evaluation values for "wristwatches for men" and "electric shavers for men" are high for male listeners, while the evaluation values for female listeners are low.

Figure 14:
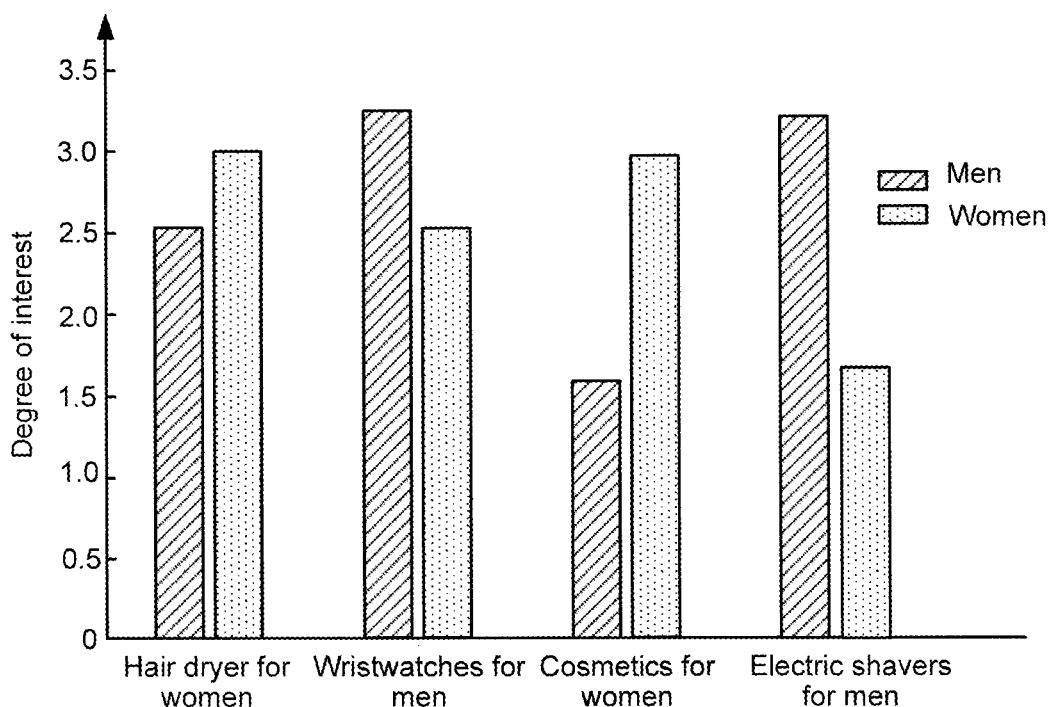
FIG. 14 is a graph illustrating interest level to a product according to the verification of the first embodiment of the present disclosure by gender and product.

FIG. 14 is a graph illustrating the interest level of a product by gender of the listener and product. The interest level for the product illustrated in FIG. 14 is the mean interest level for men and women. The degree of interest when the subject answers "very boring" is "1". The degree of interest when the subject answers "slightly boring" is "2". The degree of interest when the subject answers "slightly interesting" is "3". The degree of interest when the subject answers "very interesting" is "4". The higher interest level, the more interesting the listener was in the product introduction. Comparing FIG. 13 and FIG. 14, it was confirmed that the evaluation values and the interest level to the product introduction correlated with each other for each product.

Through these verifications, the inventors were able to obtain the finding that the timing difference of blink between the speaker and the listener correlates with the degree of interest in the listener's dialogue with the speaker.

Second Embodiment

The second embodiment controls the timing of the blink motion performed by the dialogue device 10 based on the surrounding environment of the dialogue device 10. In the following description, the same elements as those of the first embodiment described above are denoted by the same reference numerals. The hardware configuration of the dialogue device 10 of the present embodiment may be the same as that of the first embodiment described above.

Figure 15:
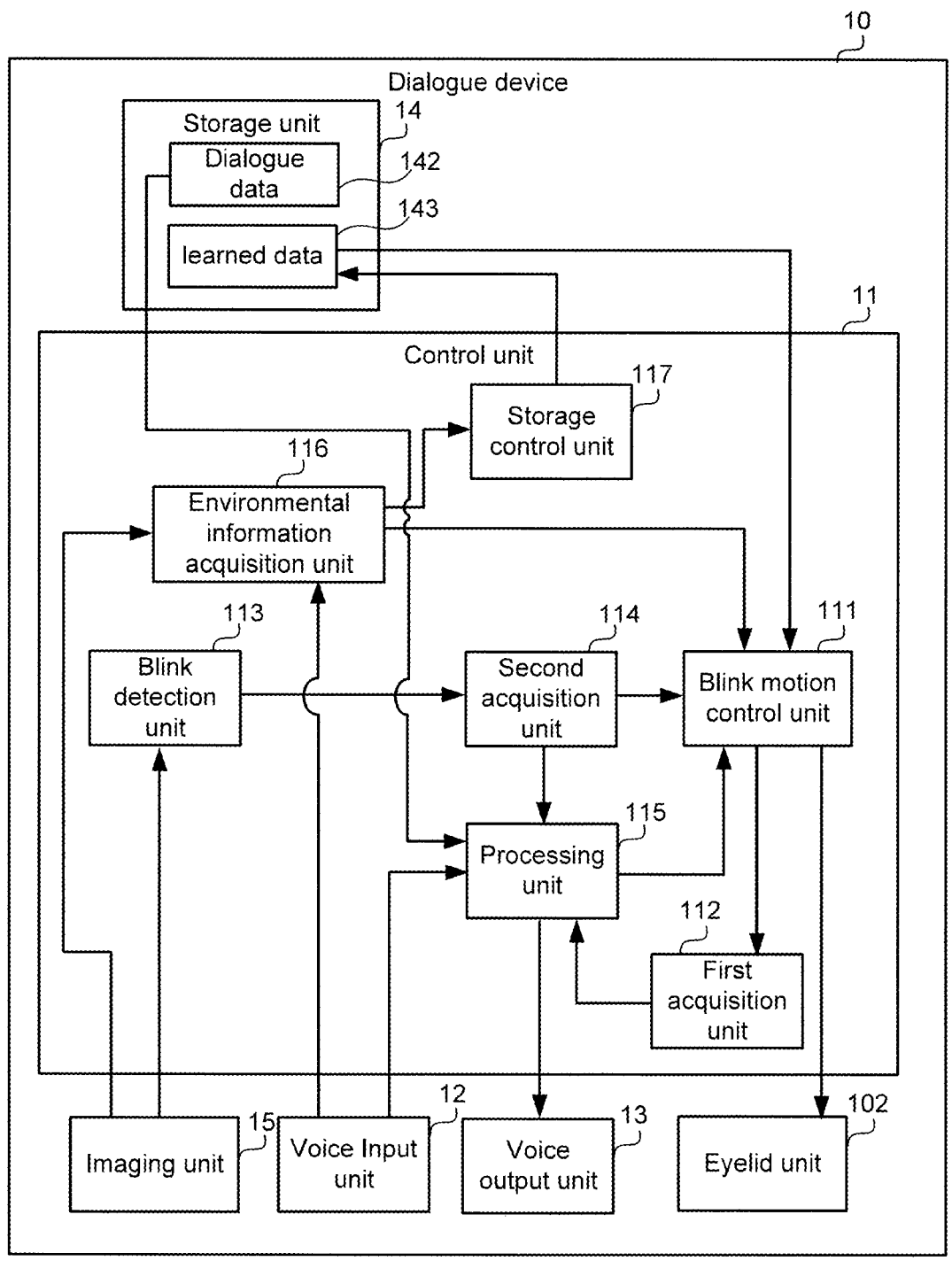
FIG. 15 is a block diagram illustrating the functional configuration of the dialogue device according to second embodiment of the present disclosure.

FIG. 15 is a block diagram illustrating a functional configuration of the dialogue device 10 according to the present embodiment. The control unit 11 of the dialogue device 10 realizes functions corresponding to a blink motion control unit 111, the first acquisition unit 112, the blink detection unit 113, the second acquisition unit 114, the processing unit 115, an environmental information acquisition unit 116, and a storage control unit 117 by executing the program 141.

The environmental information acquisition unit 116 acquires an environmental information indicating the peripheral environment of the dialogue device 10. The environmental information here denotes the environment when the dialogue device 10 is being used by the user U, in other words the environment when the dialogue device 10 is performing a dialogue with the user U. The environmental information includes, for example, one or more of voice information, sound pressure information, prosody, motion information, and peripheral information. The voice information includes information indicating voice input via the voice input unit 12, information indicating voice output via the voice output unit 13, or both. The sound pressure information indicates the sound pressure at a predetermined frequency band (e.g., audible range) of the sound information. The prosody shows the phonetic properties that appear in speech. The prosody is, for example, intonation. The motion information shows the body motion of the user U (e.g., the motion information is a motion of a face, body, or facial expression). The peripheral information indicates the environment around the user U (e.g., the brightness of the space in which the user U is located). The sound information, the sound pressure information, and the prosody are specified based on the sound input through the voice input unit 12 and the sound signals supplied to the sound output unit 13. The motion information and the peripheral information are specified using the imaging unit 15. The environmental information may be obtained using another metrology device. The environmental information may further include information about the assumed age, gender, occupation of the dialogue device 10 and user U.

The storage control unit 117 causes the storage unit 14 to store data indicating that the timing at which the user U blinks and the environment in which the dialog device 10 is used are associated each other as learning data 143. That is, the learning data 143 is the data indicating the result of learning the relation between the peripheral environments of the dialogue device 10 and the actual blink timings of the user U. The storage control unit 117 may store the learning data 143 in a memory device other than the storage unit 14, such as a memory device associated with a cloud storage service.

The blink motion control unit 111 causes the dialogue device 10 to perform the blink motion at a timing (first timing) corresponding to the environmental information acquired by the environmental information acquisition unit 116. Specifically, the blink motion control unit 111 causes the dialogue device 10 to perform a blink motion at a timing corresponding to the learning data 143 stored in the storage unit 14 and the environmental information data acquired by the environmental information acquisition unit 116. For example, the blink motion control unit 111 controls the timing of causing the dialogue device 10 to perform the blink motion, the frequency of the blink motion, and both.

Figure 16:
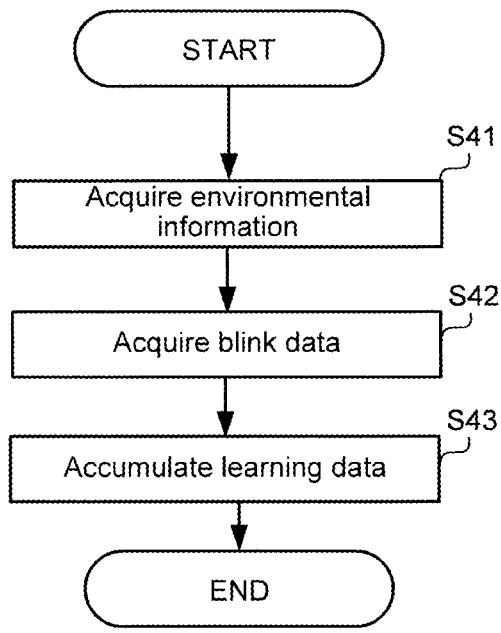
FIG. 16 is a flowchart illustrating a learning processing executed by the dialogue device according to the second embodiment of the present disclosure.

Next, a motion of the dialogue device 10 will be described. FIG. 16 is a flowchart illustrating a learning processing executed by the dialogue device 10. The learning processing is performed in parallel with the dialogue processing.

The environmental information 116 acquires the environmental information (step S41). Next, the second acquisition unit 114 acquires the blink timing by the user U (step S42). Next, the storage control unit 117 causes the storage unit 14 to store data indicating that the environment indicated by the environmental information acquired in step S41 is associated with the blink timing acquired in step S42, as the learning data 143 (step S43). The above is the description of the learning processing.

Figure 17:
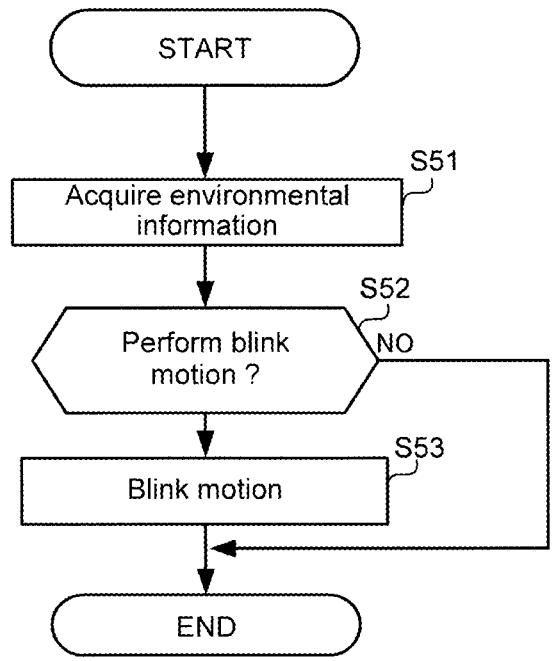
FIG. 17 is a flowchart illustrating a processing relating to the blink motion executed by the dialogue device according to the second embodiment of the present disclosure.

FIG. 17 is a flowchart illustrating a processing relating to the blink motion performed by the dialogue device 10. The processing of FIG. 17 is executed in place of the processing of the steps S11 and S12 described with reference to FIG. 5.

The environmental information acquisition unit 116 acquires environmental information (step S51). Next, the blink motion control unit 111 determines whether or not to perform the blink motion (step S52). Here, the blink motion control unit 111 determines whether or not to perform the blink motion based on the environmental information acquired in the step S51 and the learning data 143. The blink motion control unit 111 determines, for example, the presence or the absence of the blink motion and the timing of blink motion by a machine learning. The algorithm of the machine learning is, for example, a neural network, but other algorithms may be used. Until the learning data 143 is stored and accumulated by a predetermined amount, the blink motion control unit 111 may determine whether or not to perform the blink motion in the same manner as in the step S11 of the first embodiment described above.

If The blink motion control unit 111 determine that the dialogue device 10 performs the blink motion (step S52; YES), the blink motion control unit 111 causes the dialogue device 10 to perform the blink motion (step S53). If the blink motion control unit 111 determines the dialogue device 10 does not perform the blink motion (step S52; NO), the blink motion control unit 111 does not cause the dialogue device 10 to perform the blink motion. The blink processing unit 115 learns a relationship between peripheral environment surrounding the dialogue device 10 and a blink performed by a person in the environment, and causes the dialogue device 10 to perform the blink motion according to the relationship. For example, the blink motion control unit 111 may increase the frequency of the blink motion when it is determined that the story became a surprising topic. The processing related to the blink motion is described above.

According to the dialogue device 10 of the present embodiment, in addition to the effects equivalent to those of the first embodiment described above, the dialogue device 10 can perform the blink motion at a more natural time by using the learning data 143. As a result, the quality of communications between the dialogue device 10 and the user U can be expected to be improved.

The blink motion control unit 111 may cause the dialogue device 10 to blink motion at another timing (second timing), in addition to the timing corresponding to the environmental information. The blink motion control unit 111, for example, causes the dialogue device 10 to perform the blink motion by a predetermined number of times within a predetermined period (e.g., 20 times per minute) at random timing. The blink motion control unit 111 may cause the dialogue device 10 to blink motion according to predetermined rules. As a result, the dialogue device 10 can perform the blink motion at a more natural time.

The storage control unit 117 may store the learning data 143 while the evaluation value is equal to or larger than the threshold. This allows the dialogue device 10 to perform the blink motion in accordance with the blinks performed by humans when good quality communications are being performed.

When the learning data 143 is stored in the storage unit 14 in advance, the dialogue device 10 may not have a function of storing the learning data (i.e., storage control unit 117).

Third Embodiment

The third embodiment differs from the dialogue device of the first embodiment described above in that the dialogue device functions as a display device. In the following description, elements identical to those of the first embodiment described above are denoted by the same reference numerals, and elements corresponding to elements of the first embodiment described above are denoted by the same reference numerals followed by "A".

Figure 18:
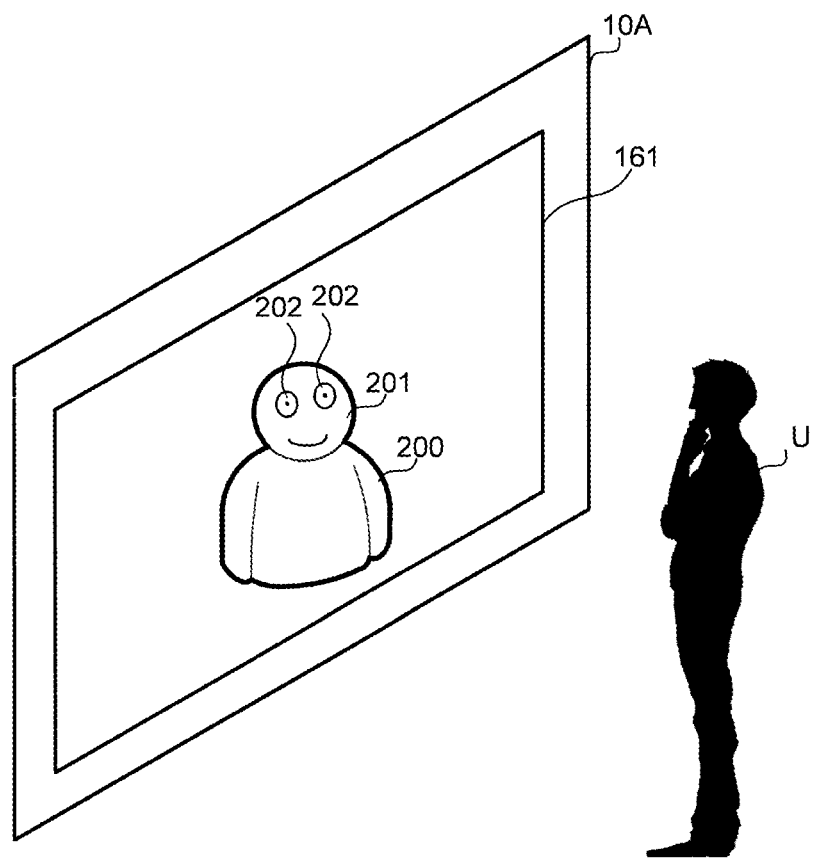
FIG. 18 is a block diagram illustrating a hardware configuration of the dialogue device according to third embodiment of the present disclosure.

FIG. 18 is a diagram illustrating an exemplary external configuration of a dialogue device 10A which is a third embodiment of the present disclosure. The dialogue device 10 A has a display region 161. The display region 161 is a region on which the images are displayed. The display region 161 displays an object 20. The objects 20 are images similar to appearance of the dialogue device 10 described in the first embodiment. The object 20 included a face unit 201 and an eyelid unit 202. The face unit 201 is a part corresponding to the face. The eyelid unit 202 is disposed on the face 201 and corresponds to the eyelid of the eye. The eyelid unit 202 performs blink motion by opening and closing. The blink motion performed by the present embodiment differs from that of the first embodiment described above in that the blink motion is performed by displaying images on the display region 161. The object 20 illustrated in FIG. 18 is a merely example, and may include images representing at least a blink motion in the present embodiment. For example, the object 20 may include at least one eyelid unit. Instead of the eyelid unit 102 of the dialogue device 10 illustrated in FIG. 1, a display unit may be provided, and objects corresponding to the eyelid unit 202 may be displayed on the display unit.

The user U is a person who communicates with the dialogue device 10A. The user U faces the dialogue device 10A and observe and perform a dialogue with the object 20 which displayed on the display region 161.

Figure 19:
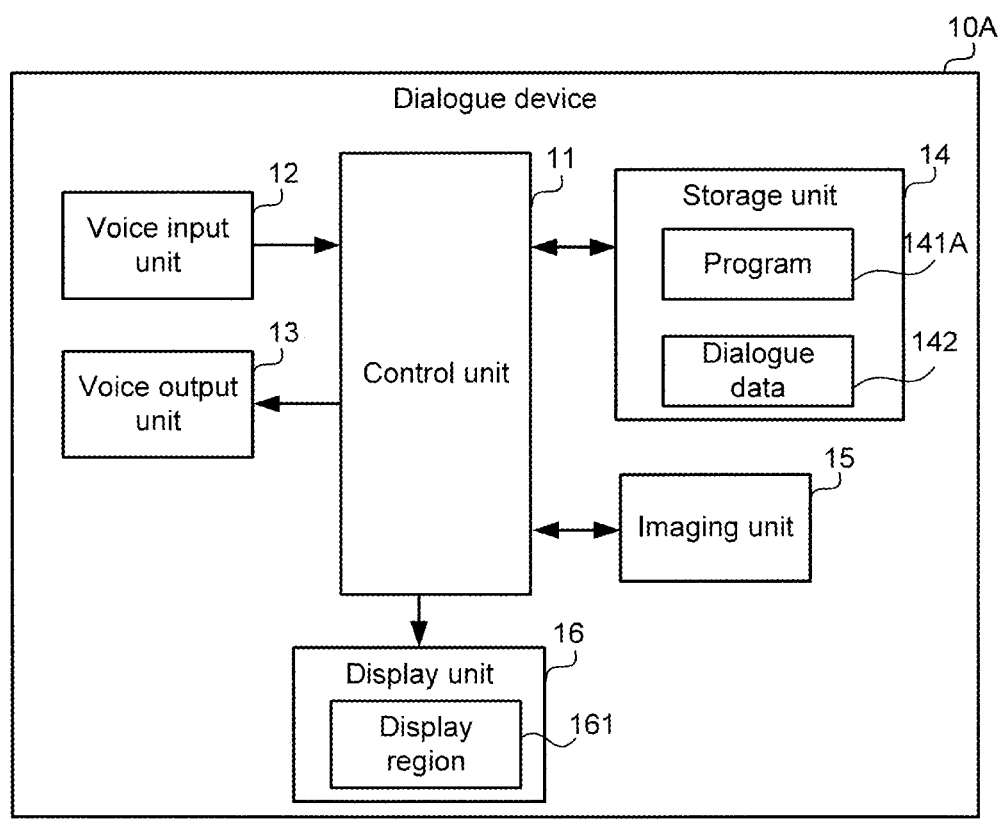
FIG. 19 is a block diagram illustrating a functional configuration of the dialogue device according to the third embodiment of the present disclosure.

FIG. 19 is a block diagram illustrating the hardware configuration of the dialogue device 10A. The dialogue device 10 includes a control unit 11, a voice input unit 12, a voice output unit 13, a storage unit 14, an imaging unit 15, and a display unit 16. The storage unit 14 stores programs 141A for causing the control unit 11 to execute predetermined functions. The display unit 16 has a display region 161 for displaying images. The display unit 16 is, for example, a liquid crystal display, an organic electroluminescence display or another display device.

Figure 20:
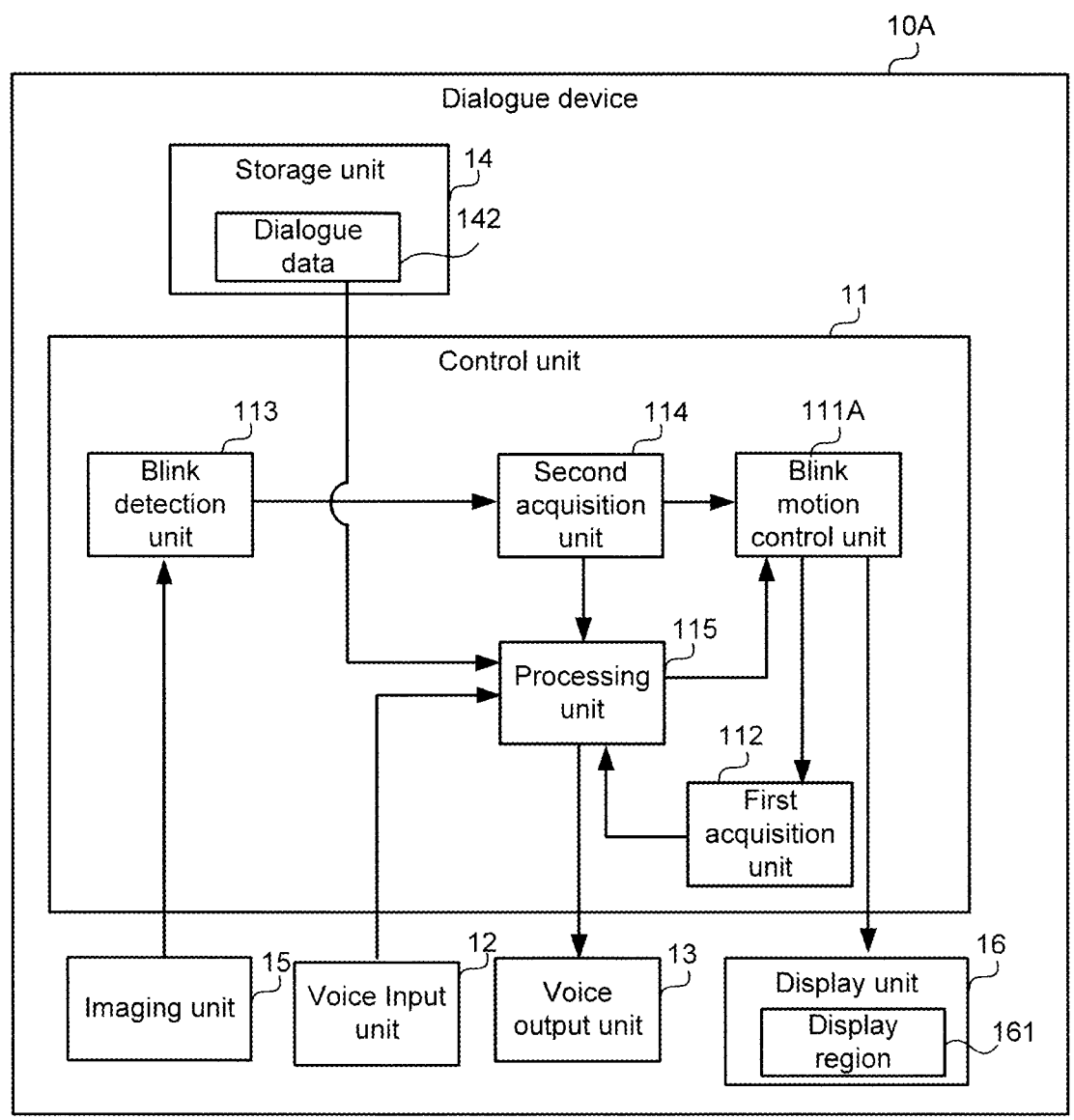
FIG. 20 is a flowchart illustrating a processing executed by the dialogue device of according to the third embodiment of the present disclosure.

FIG. 20 is a diagram illustrating a functional configuration of the dialogue device 10A. The control unit 11 of the dialogue device 10 executes the programs 141A to realize functions corresponding to a blink motion unit 111A, the first acquisition unit 112, the blink detection unit 113, the second acquisition unit 114, and the processing unit 115. The blink motion control unit 111A causes the object 20 displayed on the display region 161 of the display unit 16 to perform the blink motion. The blink motion control unit 111A supplies the blink control data for the blink motion, for example, to the display unit 16. The blink control data is data for controlling the displaying of the display unit 16. The display unit 16 causes the objects 20 to perform the blink motion according to the blink control data. The first acquisition unit 112 acquires the timings of the blink motion performed by the objects 20 (the eyelid unit 202).

The motion of the dialogue device 10A is the same as the first embodiment described above, except that the blink motion is performed under the control of the display unit 16.

The configuration of the present embodiment can also be applied to the dialogue device 10 of the second embodiment described above.

[Modification]

The present disclosure is not limited to the above-described embodiments, and can be appropriately modified within a range not departing from the spirit thereof. Although a modification of the dialogue device 10 of the first embodiment will be described below, the present disclosure can also be applied to the dialogue device 10 of the second embodiment and the dialogue device 10A of the third embodiment.

The methods of calculating the evaluation values of the processing unit 115 in the above-described embodiment are only examples. For example, the processing unit 115 may count the number of blinks of the user U and the number of blink motions of the dialogue device 10 in time series, and calculate the evaluated value based on the number of blink and the blink motion in a particular period (scene). In this instance, the processing unit 115 calculates an evaluation value that indicates that the greater the number of blink and blink motion, the greater the degree of interest in communicating with the dialogue device 10 of the user U. This is because the timing difference between the blink timing by the user U and the timing of the blink motion of the dialogue device 10 is considered to be smaller in the period in which the blink and the blink motion are greater than in the other periods. The processing unit 115 does not calculate the evaluated value, but it may process according to the difference between the timing of the blink motion and the blink timing by the user.

The processing corresponding to the difference between the blink timing by the user U and the timing of the blink motion performed by the dialogue device 10 is not limited to the utterance processing. The processing unit 115 may, for example, perform a processing of evaluating the dialogue device 10. In this case, the processing unit 115 outputs the evaluation data in association with the identifier of the dialogue device 10. The evaluation data indicates the evaluation data of the dialogue device 10. The evaluation data may be data indicating an evaluation value or data generated using the evaluation value. The evaluation data may be output, for example, by transmission, printing, displaying, or other methods. According to this modification, the quality of communications performed by the dialogue device 10 can be evaluated.

The detection of blink may be performed by a method other than the method using the imaging data. As the method, there is a method of using a non-contact sensor such as a radio wave sensor (e.g., 4 GHz radio wave sensor module), an infrared sensor, or a Doppler sensor. Also, there is a method of using a sensor that detects blink based on the motion of the muscular force of a face.

Figure 21:
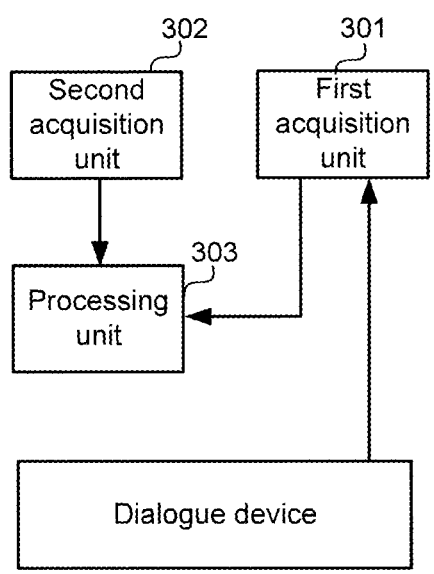
FIG. 21 is a block diagram illustrating a functional configuration of a processing device according to an embodiment of the present disclosure.

Some or all of the functions implemented by the control unit 11 described in the above-described embodiments may be included in a processor external to a dialogue device. In this case, for example, the processing device controls a dialogue device by communication (for example, communication via a public communication line). This control may include control of the blink motion and/or control of the dialogue processing. The processing device may control a plurality of dialogue device. In short, as illustrated in FIG. 21, the processing device according to the present embodiment includes a first acquisition unit 301 configured to acquire the timing of the blink motion performed by a dialogue device, a second acquisition unit 302 configured to acquire the blink timing by the user of the dialogue device and a processing unit 303 configured to perform the processing according to the difference between the timing of the blink motion and the timing of the blink by the user.

Part of the configuration and motion of the embodiment described above may be omitted. The configuration and the motion described in the above embodiment may be added. The order of the execution of the processes described in the above embodiment is merely an example, and may be changed as appropriate.

The functions realized by the control unit 11 can be realized by combinations of a plurality of programs or by coordination of a plurality of hardware resources. If the function of the control unit 11 is realized using the program, the program 141, 141A to realize this function may be provided in the state memorized in computer-readable recording media such as various magnetic recording media, various optical recording media, various optical magnetic recording media, and a semiconductor memory. The program may be distributed over a network. It is possible to understand that the present disclosure is as a processing method.

Fourth Embodiment

Techniques for estimating the degree of interest in the visual information a person observed based on the unconscious motion performed by the person have been proposed in the past. Japanese Patent. No. 5,771,127 discloses that the degree of attention to an image is estimated based on change of visual line of the person and the interval of blink. Japanese Unexamined Patent Application Publication No. 2009-267445 discloses selecting a satisfaction calculation method corresponding to a genre of a content to calculate a satisfaction degree of the content of the user. Japanese Unexamined Patent Application Publication No. 2005-142975 discloses generating viewing quality data based on the terminal operation data and the body data including blinks. Re-publication of PCT International Publication No. 2008-72739 discloses calculating the interest level for the content based on the eye motion of the viewer. With respect to the blinks of test subjects viewing the same image, the inventors herein disclose that the blinks of a plurality of test subject when viewing a manual image are synchronized in the paper 3, Richard J. Wiseman and Tamami Nakano, "Blink and you'll miss it: the role of blink in the perception of magic tricks, "PeerJ, e1873, [online]", [Searched on Mar. 12, 2018], Internet <URL: https://peerj.com/articles/1873/?utm#source=TrendMD&utm#campaign=PeerJ#TrendMD#1&utm#medium=TrendMD>, (2016).

On the other hand, the number and frequency of human blinks differ greatly among individuals. Therefore, it is difficult to use the number and frequency of blinks as an objective index such as the degree of interest.

The inventors have found that differences in the timings of blinks of a plurality of users can be used as an index of the degree of interest in visual data observed by the plurality of users. For example, it can be inferred that in a period in which the synchronization degree in the timing of the blinks of the plurality of users is high, the plurality of users show strong interest in the visual information observed during the period. On the other hand, it can be inferred that in the period in which the synchronization degree is low, the plurality of users do not show strong interest in the visual information observed in the period. Verification leading to such knowledge will be described later. Based on these findings, in the fourth to seventh embodiments, data processing system is described, which performs processing according to the synchronization degree of blinks of a plurality of users as techniques for using blinks of persons as an objective index.

Figure 22:
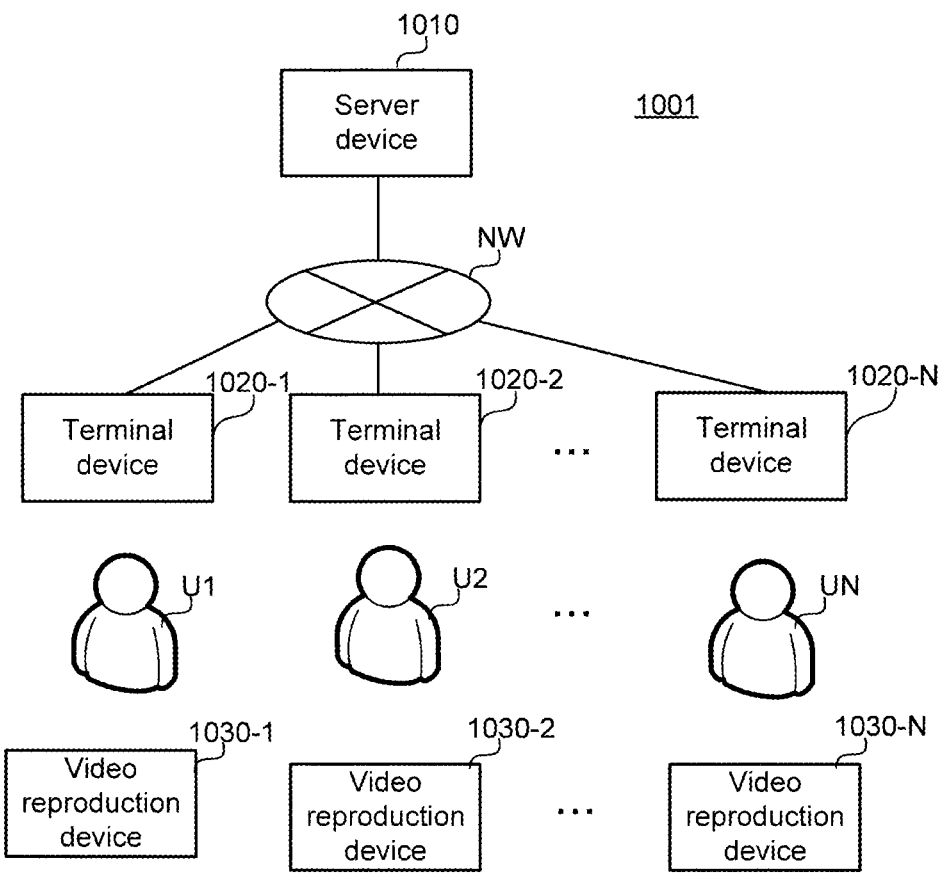
FIG. 22 is a block diagram illustrating an overall configuration of a data processing system according to fourth embodiment of the present disclosure.

FIG. 22 is a block diagram illustrating an overall configuration of a data processing system 1001 according to a fourth embodiment of the present disclosure. The data processing system 1001 evaluates the visual information based on blinks of a plurality of users observing predetermined visual information. Visual information collectively refers to the information that a person obtains through vision. In the present embodiment, the visual information is a video. In the video, information that a person can recognize visually changes with time. The video may further include information (i.e., sound) that the person can recognize through hearing. The video of the present embodiment is, for example, a video related to television broadcasting, such as a television program or a commercial message.

The data processing system 1001 includes a server device 1010 and a plurality of terminal device 1020 (1020-1, 1020-2, . . . , 1020-N). The server device 1010 acquires data indicating the blink timing by the user from each of a plurality of terminal device 1020, and evaluates the video based on the acquired data. The server device 1010 is managed and operated by, for example, a business operator who performs aggregation and analysis of viewing tendencies of videos by users. The server device 1010 communicates with each of the plurality of terminal devices 1020 through the communication line NW. The communication line NW is, for example, a public communication line exemplified by the Internet or a private line. The server device 1010 is an example of a device having a data processing device according to the present disclosure.

The plurality of the terminal devices 1020 are used by the user viewing the video. In FIG. 22, terminal device 1020-1, 1020-2, . . . , 1020-N (where N is a natural number of 2 or more) are illustrated as a plurality of the terminal device 1020. The user of the terminal device 1020-*i* (where 1≤I≤N) is referred to as "user Ui" in the following description. The user Ui uses a video reproduction device 1030-*i* to observe the video. The video reproduction device 1030-1 through 1030-N are, for example, television.

The terminal device 1020 is, for example, a portable terminal device exemplified by a smart phone, a tablet terminal, and a wearable computer. Alternatively, the terminal device 1020 may be a fixed terminal device installed in a viewing space of a video (for example, a room in which the video reproduction device 1030-1 to 1030-N is installed). The terminal device 1020 is provided at a position where a blink of a user who observes a video can be detected. For example, the terminal device 1020 is provided in the vicinity of the video reproduction device 1030-1 to 1030-N.

Figure 23:
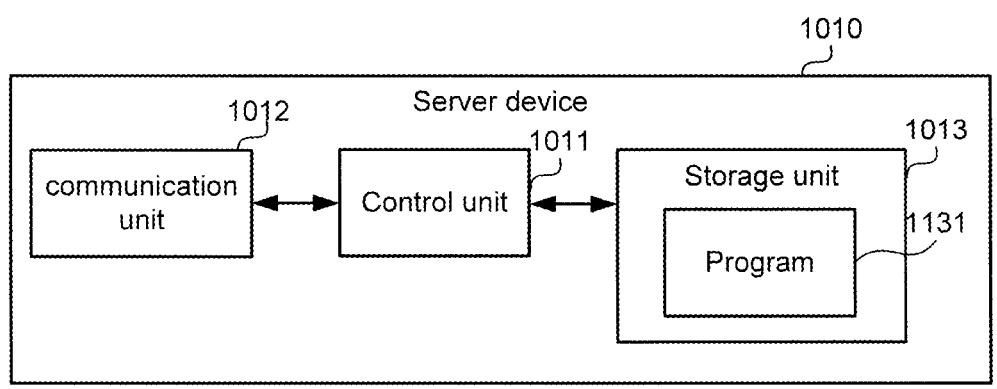
FIG. 23 is a block diagram illustrating a hardware configuration of a server device according to the fourth embodiment of the present disclosure.

FIG. 23 is a block diagram illustrating a hardware configuration of the server device 1010. The server device 1010 includes a control unit 1011, a communication unit 1012, and a storage unit 1013. The control unit 1011 controls each unit of the server device 1010. The control unit 1011 includes, for example, a calculation processing device exemplified by CPU, and a memory. The memory includes, for example, a RAM used by the calculation processing device as a work area and a ROM for storing a control program.

The communication unit 1012 communicates with each of the plurality of terminal devices 1020 by wire or wirelessly via communication line NW. The communication unit 1012 includes, for example, a communication circuit and an antenna.

The storage unit 1013 stores data. The storage unit 1013 stores, for example, a program 1131. The program 1131 is a program for causing the control unit 1011 to execute a predetermined function. The storage unit 1013 may include any kind of recording medium exemplified by, for example, an optical recording medium, a magnetic recording medium, and a semiconductor recording medium.

Figure 24:
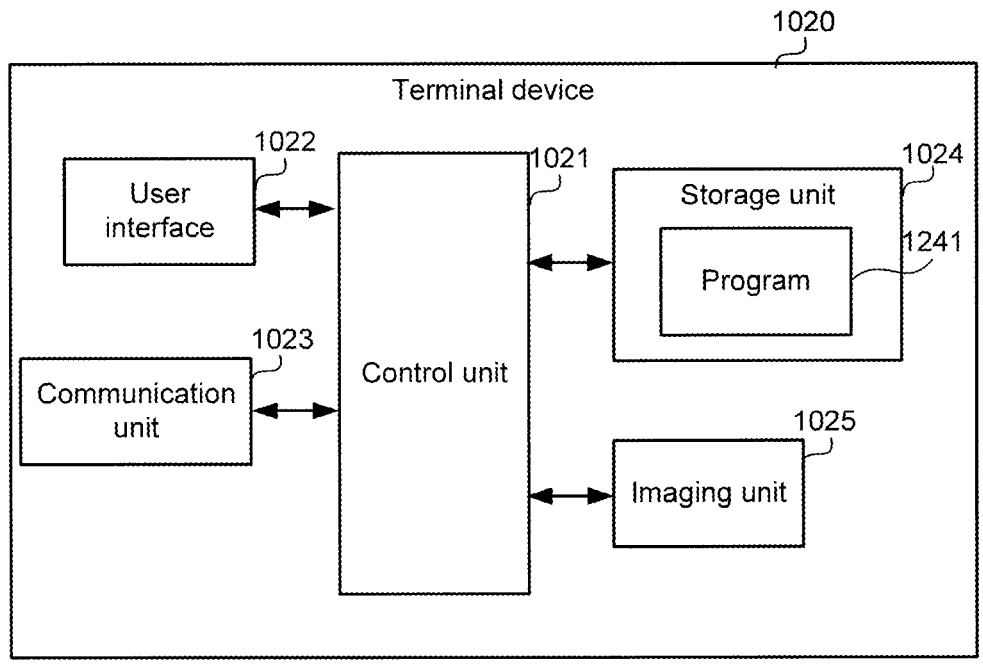
FIG. 24 is a block diagram illustrating a hardware configuration of a terminal device according to the fourth embodiment of the present disclosure.

FIG. 24 is a block diagram illustrating the hardware configuration of the terminal device 1020. The terminal device 1020 includes a control unit 1021, a user interface 1022, a communication unit 1023, a storage unit 1024, and an imaging unit 1025. The control unit 1021 controls each unit of the terminal device 1020. The control unit 1021 includes, for example, a calculation processing devices exemplified by CPUs, and a memory. The memory includes, for example, a RAM used by the CPU as a work area and a ROM for storing a control program. The control unit 1021 further includes a clocking unit for measuring a time defined on a predetermined time base. The time axis defines, for example, an absolute time or a playback position of a video (e.g., a relative time based on a playback start time of the video).

The user interface 1022 is an interface configured to perform a dialogue with a user. The user interface 1022 includes, for example, an operation unit (e.g., physical keys or touch sensors) configured to accept operation and a display unit (e.g., a liquid crystal display) configured to display information. The communication unit 1023 communicates with the server device 1010 through the communication line NW. The communication unit 1023 includes, for example, a communication circuit and an antenna. The storage unit 1024 stores data. The storage unit 1024 stores, for example, the program 1241. The program 1241 is a program for causing the control unit 1021 to realize a predetermined function. The storage unit 1024 may include any kind of recording medium exemplified by, for example, an optical recording media, a magnetic recording media, and a semiconductor recording media.

The imaging unit 1025 captures an image of the subject, and generates imaging data indicating the captured image. The subject includes at least a face of the user, more particularly eyes of the user. The imaging unit 1025 includes, for example, an imaging device exemplified by a CCD (Charge Coupled Device) image sensor, and lenses.

Figure 25:
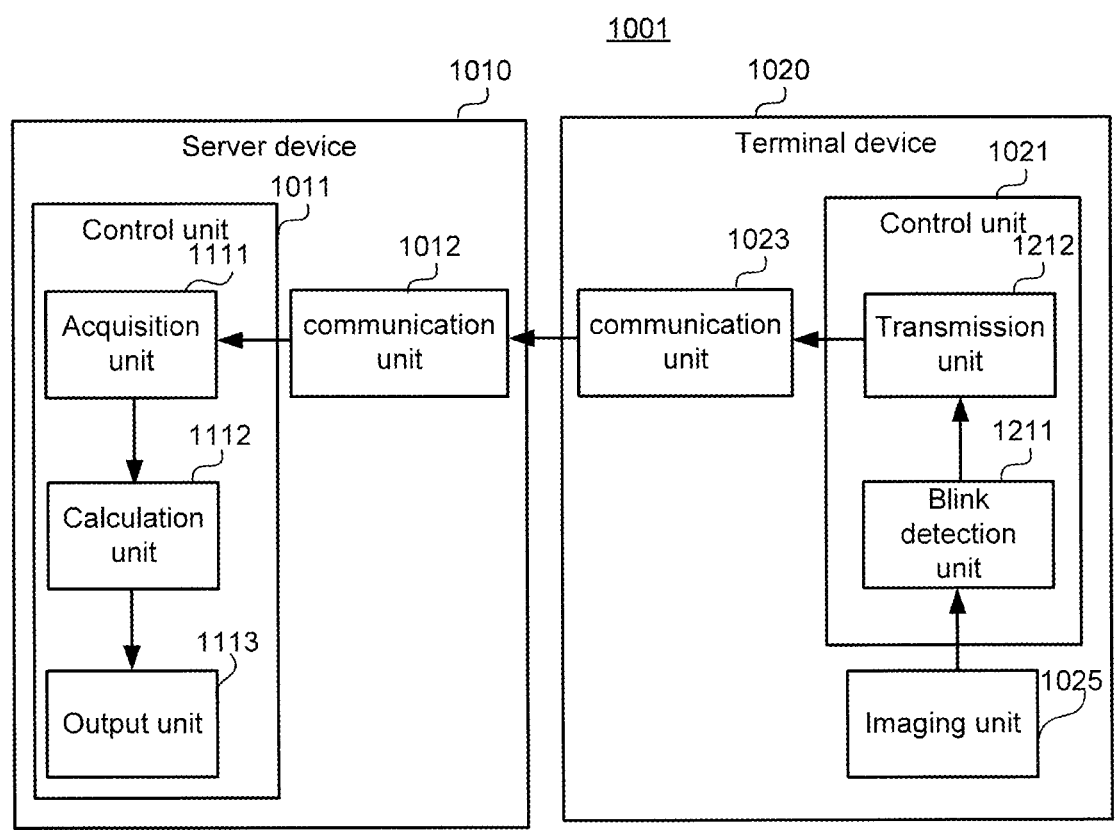
FIG. 25 is a block diagram illustrating a functional configuration of a data to processing system according to the fourth embodiment of the present disclosure.

FIG. 25 is a block diagram illustrating a functional configuration of the data processing system 1001. The control unit 1011 of the server device 1010 corresponds to a data processing device. The control unit 1011 includes an acquisition unit 1111, a calculation unit 1112, and an output unit 1113. The control unit 1011 realizes function corresponding to the acquisition unit 1111, the calculation unit 1112, and the output unit 1113 by executing the program 1131. Each of the control unit 1021 of the plurality of terminal device 1020 realizes a function corresponding to the blink detection unit 1211 and the transmission unit 1212 by executing the program 1241.

In the terminal device 1020, the blink detection unit 1211 detects the blink of the user. Specifically, the blink detection unit 1211 detects the blinking of the user based on the imaging data generated by the imaging unit 1025. The transmission unit 1212 transmits data indicating the blink timing by the user (hereinafter referred to as "blink data") to the server device 1010 using the communication unit 1023. The blink data of the present embodiment is data (first data) in which the times at which blinks are detected are arranged in the order of the times.

In the server device 1010, the acquisition unit 1111 acquires the blink data from each of the plurality of the terminal device 1020 using the communication unit 1012.

The calculation unit 1112 calculates the index according to the synchronization degree of the blink timings of the plurality of users based on the difference in the blink timings of the plurality of users. The calculation unit 1112 calculates the index based on the blink data acquired by the acquisition unit 1111. In the present embodiment, the index is an evaluation value of the degree of the interest in videos of a plurality of users.

The output unit 1113 outputs the data corresponding to the index calculated by the calculation unit 1112. In the present embodiment, the output unit 1113 may output the index itself, or may output data (e.g., contents) directly or indirectly specified from the index.

Figure 26:
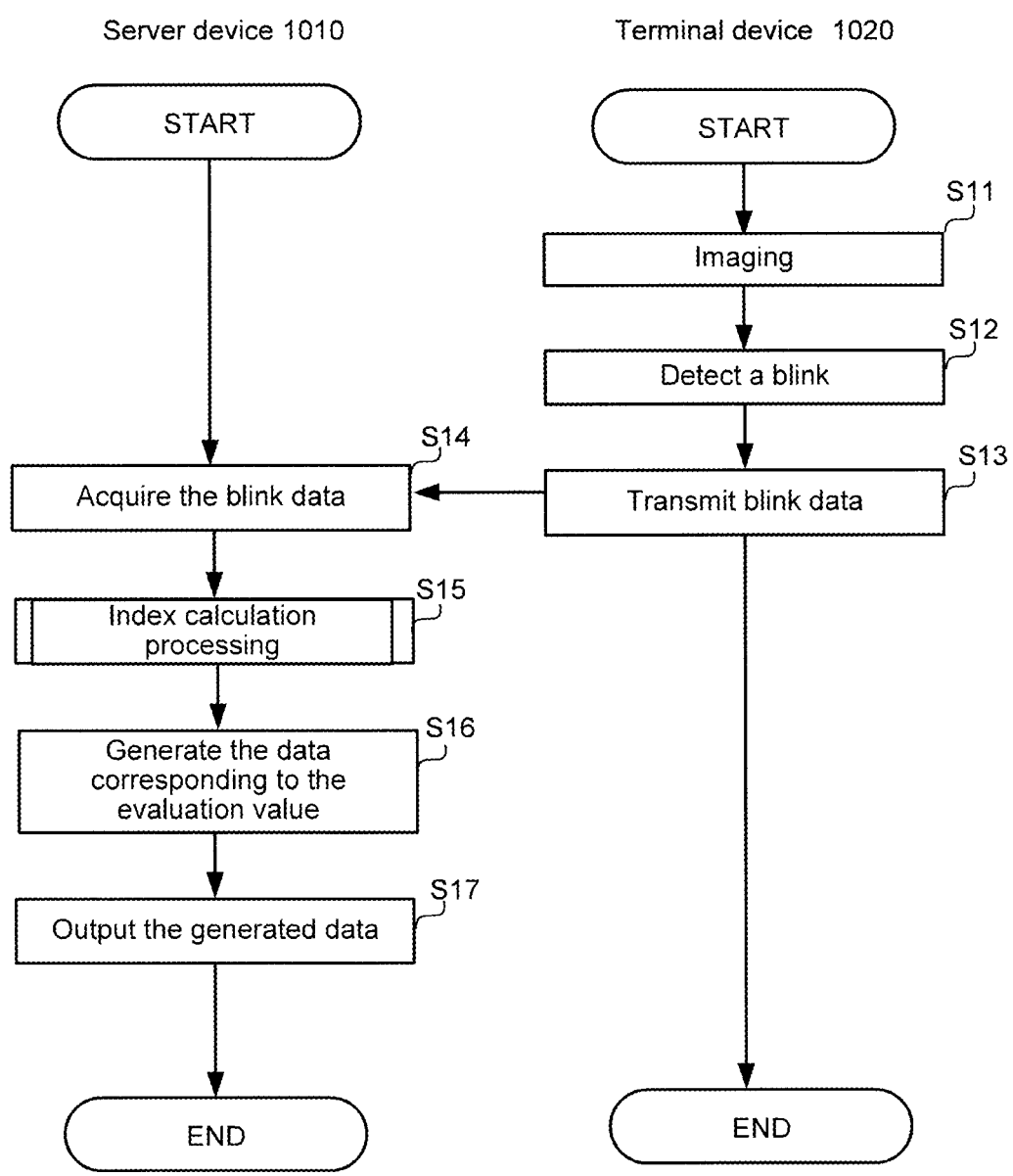
FIG. 26 is a flowchart illustrating a processing executed by a data processing system according to the fourth embodiment of the present disclosure.

Next, the motion of the data processing system 1001 will be described. FIG. 26 is a flowchart illustrating processing executed by the data processing system 1001.

In the terminal device 1020, the blink detection unit 1211 causes the imaging unit 1025 to image the eyes of the user (step S11). The blink detection unit 1211 detects the blink of the user based on the imaging data generated by the imaging unit 1025 (step S12). Various known techniques may be applied to the blink detection algorithm. For example, the blink detection unit 1211 extracts a plurality of characteristic points along the periphery of the user's eye from the image showed by the imaging data. The blink detection unit 1211 extracts the characteristic point based on, for example, Haar-like. The blink detection unit 1211 detects the presence or absence of a blink of a user by specifying the direction of the movement of the extracted feature points and the temporal change of its velocity based on the imaging data of a plurality of frames. For example, due to the blink of a person, a rapid change in the moving velocity of the feature point occurs between approximately 0 and 300 milliseconds. Therefore, when the velocity change within the predetermined period becomes equal to or greater than the threshold, the blink detection unit 1211 detects that the user blinks.

The blink detection unit 1211 detects blink in real time, for example, based on the imaging data supplied from the imaging unit 1025. Alternatively, the blink detection unit 1211 may cause the storage unit 1024 to store the imaging data, and reads the imaging data at a predetermined timing to detect a blink.

The transmission unit 1212 transmits the blink data indicating the blink timing by the user to the server device 1010 using the communication unit 1023 (step S13). Furthermore, the transmission unit 1212 may transmit the video identification information to the server device 1010 in association with the blink data. The video identification information identifies the video viewed by the user. The video identification information includes, for example, identifying information for identifying a video, broadcast date and time information indicating the broadcast date and time of the video, and channel information indicating the broadcast channel of the video. The timing of the transmission of the blink data is not limited. The transmission timing is, for example, a predetermined timing (e.g., a predetermined time once a day) or a timing at which a request is provided from the server device 1010.

The acquisition unit 1111 of the server device 1010 acquires the blink data from each of the plurality of the terminal device 1020 using the communication unit 1012 (Step S14). When the terminal device 1020 transmits a video identification information, the acquisition unit 1111 further acquires the video identification information.

The calculation unit 1112 performs the index calculation processing based on the blink data acquired by the acquisition unit 1111 (step S15).

Figure 27:
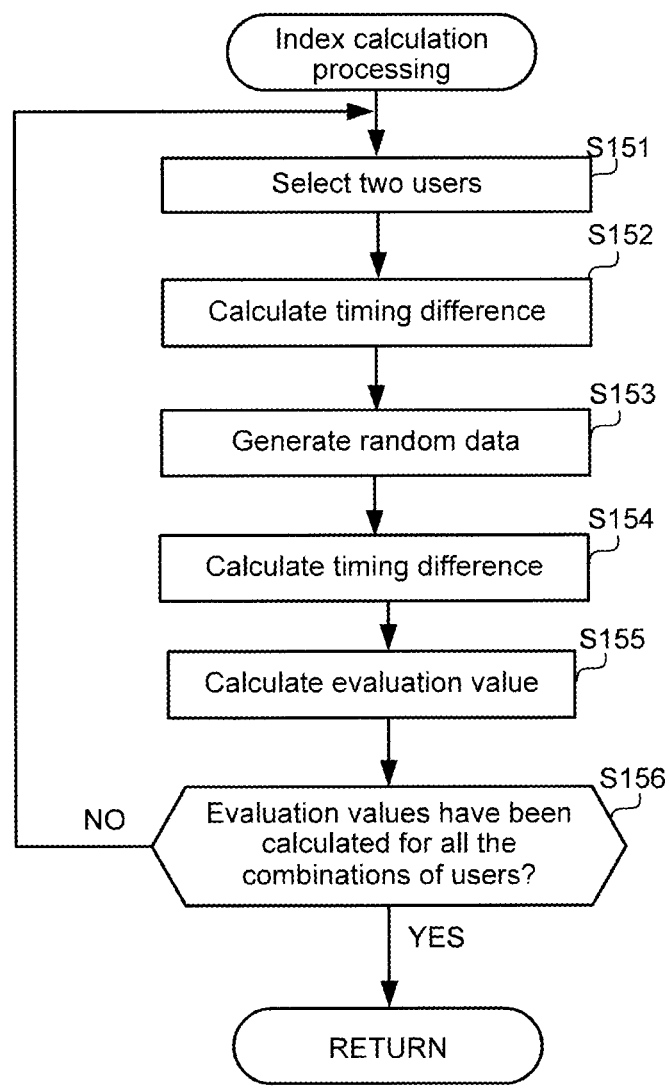
FIG. 27 is a flowchart illustrating an index calculation processing according to the fourth embodiment of the present disclosure.

FIG. 27 is a flowchart illustrating the index calculation processing. Hereinafter, the index calculation processing will be described with reference to specific examples.

The calculation unit 1112 selects two users from among N number of users, U1 to UN (step S151). The two selected users are hereinafter referred to as "first user" and "second user", respectively. Here, it is assumed that the calculation unit 1112 selects the user U1 and the user U2.

Next, the calculation unit 1112 calculates a difference between the blink timing of the first user and the blink timing of the second user. (step S152). The calculation unit 1112 calculates the difference in timing (hereinafter referred to as "timing difference") for all combinations of the blink timing of the first user and the blink timing of the second user.

Figure 28:
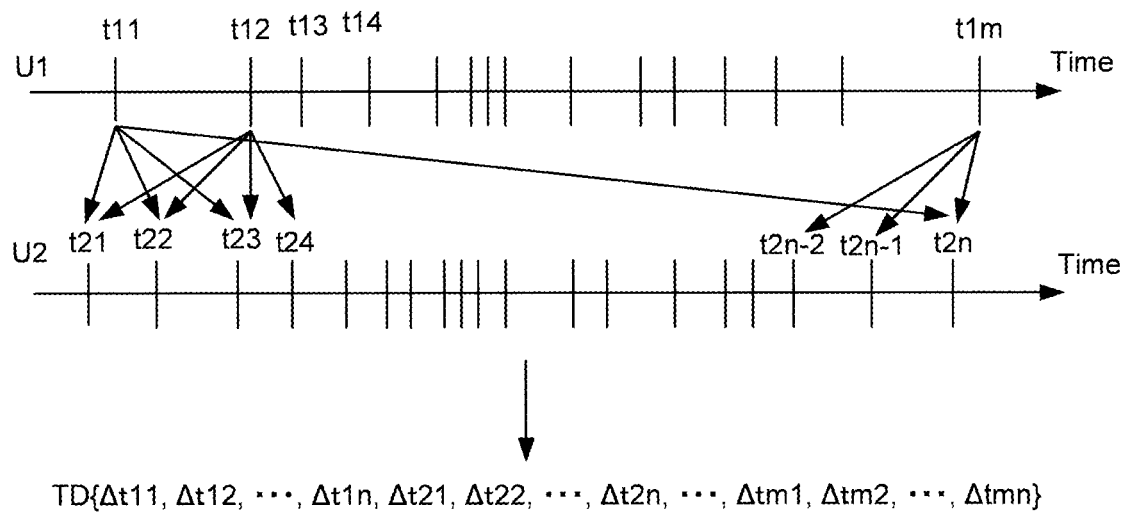
FIG. 28 is a diagram for illustrating a method of calculating a timing difference of the blink motion according to the fourth embodiment of the present disclosure.

FIG. 28 is a diagram illustrating a method of calculating a difference in the blink timing. FIG. 28 is a timing chart showing the timing at which blink is detected. As illustrated in FIG. 28, the blink timing by the user U1 is represented by t11, t12, . . . , t1B in the order of time. The blink timing by the user U2 is represented by t21, t22, . . . , t27 in the order of the time. In this case, the calculation unit 1112 calculates the difference from each of t21, t22, . . . , t27 for each of t11, t12, . . . , t1B. The timing difference between the blink timing t1$i$ (where 1≤i≤m) and the blink timing t2$j$ (where 1≤j≤n) is hereinafter referred to as "Δtij". In this case, the calculation unit 1112 calculates the timing difference TD {Δt11, Δt12, . . . , Δt17, Δt21, Δt22, . . . , Δt27, . . . , ΔtB1, ΔtB2, . . . , ΔtBn}.

Figure 29:
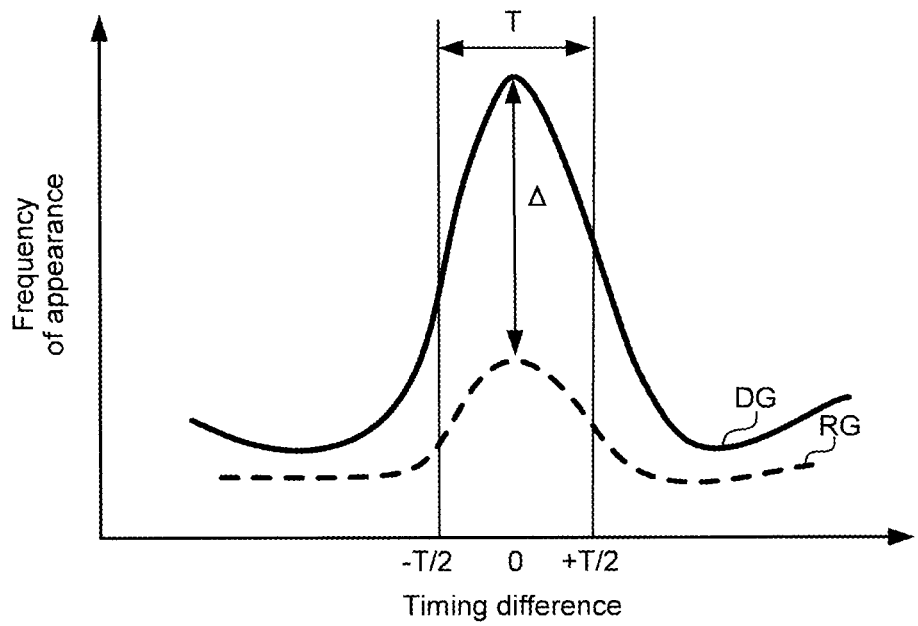
FIG. 29 is a diagram illustrating a frequency distributions of the timing difference according to the fourth embodiment of the present disclosure.

FIG. 29 is a graph illustrating the frequency of the timing difference. In the graph DG of FIG. 29, the horizontal axis corresponds to the timing difference, and the vertical axis corresponds to the degree of appearance (i.e., frequency) of each timing difference. In the case illustrated in FIG. 29, the frequency is high within the time range T in which the timing difference is relatively low.

By the way, it is considered that the distribution of the frequency illustrated by the graph DG is caused by the observation of the video by the first user and the second user, and the blinking characteristics of the first user and the second user, for example, the number of times and the frequency. Therefore, in order to clarify that the blinks of the first user and the second user indicated by the timing difference TDs are caused by observing the video to what extent, the calculation unit 1112 analyzes the frequency distributions using the surrogate data method.

That is, the calculation unit 1112 generates random data based on the blink data acquired in the step S13 (step S153). The random data here includes K random data R1-RK (second data) in which the order of interval of blinks on the time-axis is changed randomly (e.g., 1000 ways) for one or both of the two users selected in the step S151.

Figure 30:
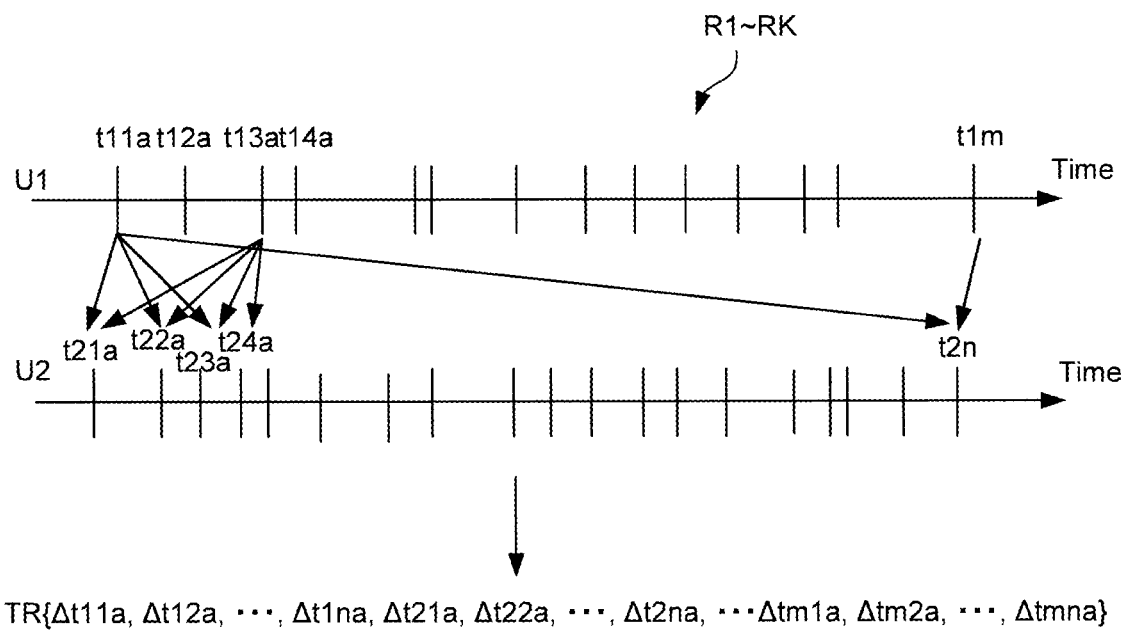
FIG. 30 is a diagram illustrating an example of random data according to the fourth embodiment of the present disclosure.

FIG. 30 is a diagram illustrating an example of the random data R1 to RK. The random data R1 to RK illustrated in FIG. 30 are random data in which the order of interval of blink has not been changed for the user U1 and the order of interval of blinking has been changed for the user U2. In the random data R1 to RK, the blink timing by the user U2 is represented as t21$a$, t25$a$, ••• t23$a$ in the order of the time. The timing "t2$j$" illustrated in FIG. 28 corresponds to the timing "t2$ja$" illustrated in FIG. 30.

Next, the calculation unit 1112 calculates the timing difference, which is the difference between the blink timing of the first user and the blink timing of the second user, for each of the K pieces of random data R1 to RK (step S154). The timing difference calculation method may be the same as the step S152. In other words, the calculation unit 1112 calculates the timing difference for all combinations of the blink timing of the first user and the blink timing of the second user for each of the random data R1 to RK. The timing difference, which is the difference between the blink timing t1$ia$ (where 1≤i≤m) and the blink timing t2$ja$ (where 1≤j≤n), is hereinafter referred to as "Δtija". In this instance, the calculation unit 1112 calculates the timing difference TR {Δt11$a$, Δt15$a$, . . . , Δt13$a$, Δt21$a$, Δt25$a$, . . . , Δt23$a$, . . . , ΔtB1$a$, ΔtB5$a$, . . . , ΔtB3$a$}. The frequency of appearance of the timing difference in the random data R1 to RK is illustrated in, for example, the graph RG of FIG. 29. The graph RG illustrates the mean frequency of appearance of the timing difference of the random data R1-RK.

Next, the calculation unit 1112 calculates the evaluation value based on the timing difference based on the blinking data and the timing difference based on the random data (step S155). The random data is data obtained by randomly changing interval of the blink of the user U2, and can be said to be data in which time series data is collapsed while maintaining the number and interval of the blink of the user U2. Therefore, by comparing the blink data with the random data, it is possible to understand the degree to which the appearance distributions of the timing difference indicated by the blink data appeared due to observing the video.

Specifically, the calculation unit 1112 calculates the evaluation value by the Z score. That is, the calculation unit 1112 subtracts the mean of the timing difference in the random data R1 to RK from each of the timing difference TD {Δt11, Δt12, ..., Δt17, Δt21, Δt22, ..., Δt27, ..., ΔtB1, ΔtB2, ..., ΔtBn} indicated by the blinking data. Further, the calculation unit 1112 calculates the evaluation value Z by dividing the obtained value by the standard deviation of the timing difference in the random data R1 to RK. For example, if the blink data is the same as the random data, the evaluation value Z is 0. In this case, it can be inferred that the blink timings between peoples are not synchronized due to the observation of the video. On the other hand, when the evaluation value Z is large and the difference between the blink data and the random data is large, it can be inferred that the blink timings between peoples are synchronized due to the observation of the video. Referring to FIG. 29, the larger the difference A in the frequency of appearance, the larger the evaluation value Z is.

Figure 31:
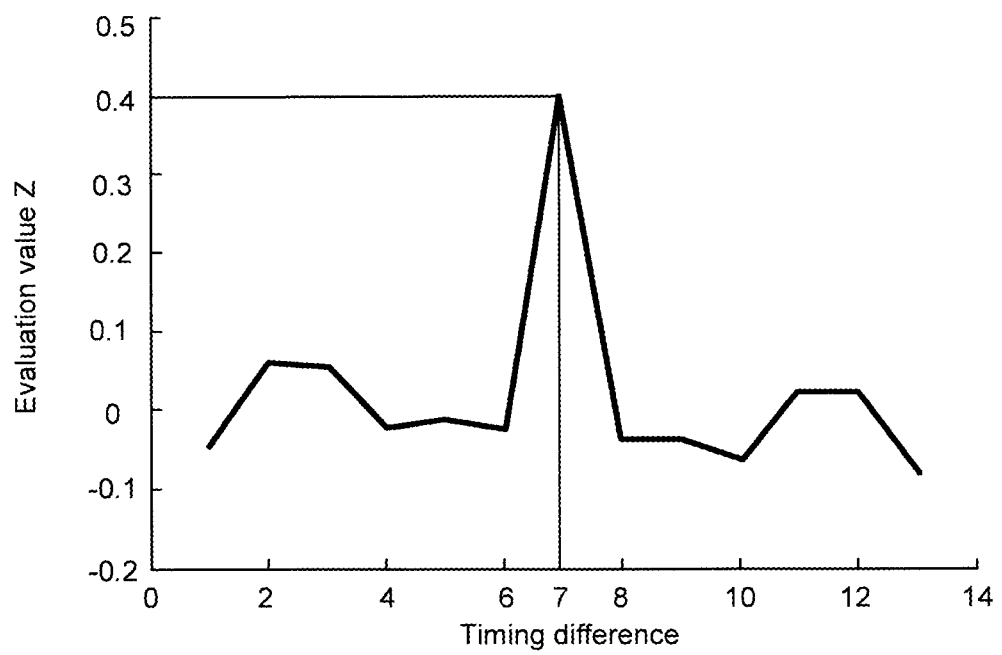
FIG. 31 is a diagram illustrating an example of an evaluation value according to the fourth embodiment of the present disclosure.

FIG. 31 is a graph illustrating an example of the evaluation value Z. In the graph illustrated in FIG. 31, the horizontal axis corresponds to the timing difference, the vertical axis corresponds to the evaluated value. Here, the timing difference is represented by the values of a bin. The bin number "7" indicates that the timing difference is treated as "0". The time range between bins is 300 milliseconds. It means that the timing difference is larger in the positive direction, in the direction in which the value of the bin number increases. For example, the bin number "8" means there is a difference of +300 milliseconds and the bin number "9" means there is a difference of +600 milliseconds. On the contrary, it means that the timing difference is large in the negative direction, in the direction in which the value of the bin number decreases. For example, the bin number "6" means there is a difference of −300 milliseconds. The bin number "5" means there is a difference of −600 milliseconds. If the timing difference is positive, it means that the blink timing of the second user is earlier than the blink timing of the first user. If the timing difference is negative, it means that the blink timing of the first user is earlier than the blink timing of the second user. In the present embodiment, the frequency of appearance of blinks in which the timing difference is 300 milliseconds or less indicates the evaluation value Z of the bin number "7". In other words, the frequency of appearance corresponding to a number other than the bin number "7" is not used for calculating the evaluation value Z. In the example illustrated in FIG. 31, the evaluation value Z is "0.4". The calculation unit 1112 may calculate one evaluation value for the entire playback period of the video, or may divide the playback period into a plurality of unit periods, for example, a period of 30 seconds, and calculate the evaluation value for each unit period.

The calculation unit 1112 may perform the index calculation processing based on the video identification information in addition to the blink data. In this instance, the calculation unit 1112 specifies the videos viewed by each of the N users based on the video identification information, and calculates the index based on the blink timings of the N users on the common time axis.

Next, the calculation unit 1112 determines whether or not evaluation values have been calculated for all the combinations of users (step S156). When the calculation unit 1112 determines "NO" in step S156, the calculation unit 1112 returns to the processing of the step S151. Then, the calculation unit 1112 changes the combinations of the two users to be selected, and calculates the evaluation values (steps S151~S154). If the calculation unit 1112 determines "YES" in step S156, the calculation unit 1112 ends the index calculation processing.

The random data may be data in which interval order of the blink has not been changed for the user U2 and interval order of the blink has been changed for the user U1. The random data may be data in which interval order of the blink of two users (e.g., the user U1 and the user U2) selected in the step S151 has been changed.

When the index calculation processing is completed, the output unit 1113 generates and outputs data corresponding to the calculated evaluation values (steps S16 and S17 in FIG. 26).

Figure 32:
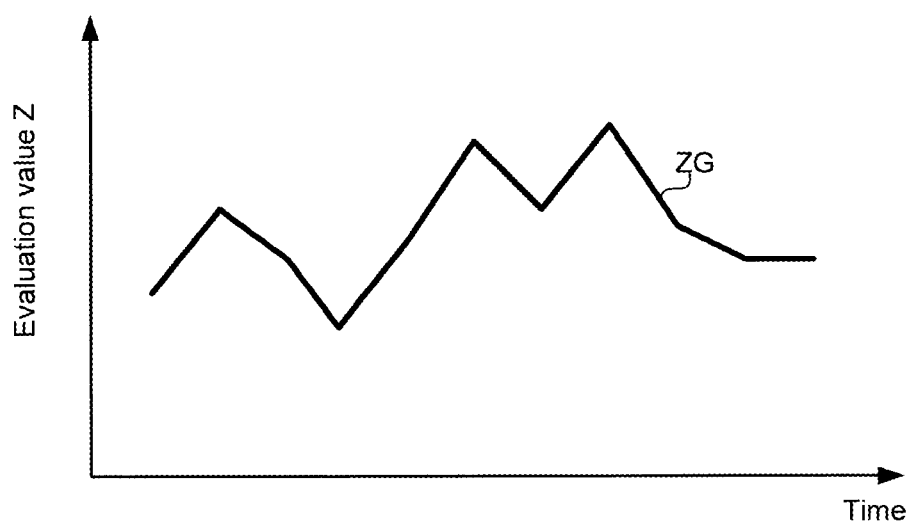
FIG. 32 is a diagram illustrating an example of a data output in step S17 according to the fourth embodiment of the present disclosure

FIG. 32 is a diagram illustrating an example of data output in step S17. In this case, the output unit 1113 outputs an evaluation value associated with the time. Specifically, the output unit 1113 makes the horizontal axis correspond to the time, and the vertical axis correspond to the evaluation value. Therefore, the output unit 1113 generates a graph ZG indicating temporal changes in the evaluation values. The evaluation value on the vertical axis indicates, for example, the mean value of the evaluation values calculated according to $_NC_2$ ways for each unit period. The graph ZG is a graph that quantitatively represents the temporal change of the evaluation value for the video of N users. For example, the output unit 1113 calculates the evaluation value for the entire playing period of the video, for example, the broadcasting period of the program, but may calculate the evaluation value for a part of the playing period.

The output unit 1113 may provide moving average of the evaluation values of the N users. The method of outputting the data in the step S17 is not limited. For example, the method of outputting data may be performed by communication, printing, or displaying.

Usually, the audience rating of television broadcasting is measured based on the channel selected at each time. Therefore, it is impossible to quantitatively understand whether or not the viewer is interested in the program being tuned, and the degree of the interest. On the other hand, according to the data processing system 1001, the degree of interest in a video can be quantitatively evaluated according to the timing difference of blinks of a plurality of users. This evaluation result can be used for analysis of viewing trends, marketing, etc.

Here, the basis for using the difference in the blink timing of a plurality of users for objective evaluation of visual information will be described. The inventors of the present disclosure performed the verification described below.

The inventors created the following three types of videos (video 1), (video 2), and (video 3) with 59 university students as test subjects. Then, the inventors reproduced the video for test subjects in the order of (video 1):→(video 2):→(video 3):→(video 1):→(video 2):→(video 3):→ (video 1):→(video 2):→(video 3). The play time of each video is 3 minutes and the total play time of the videos is 27 minutes. The inventors of the present disclosure detected the blink of test subjects for observing these videos.

Figure 33:
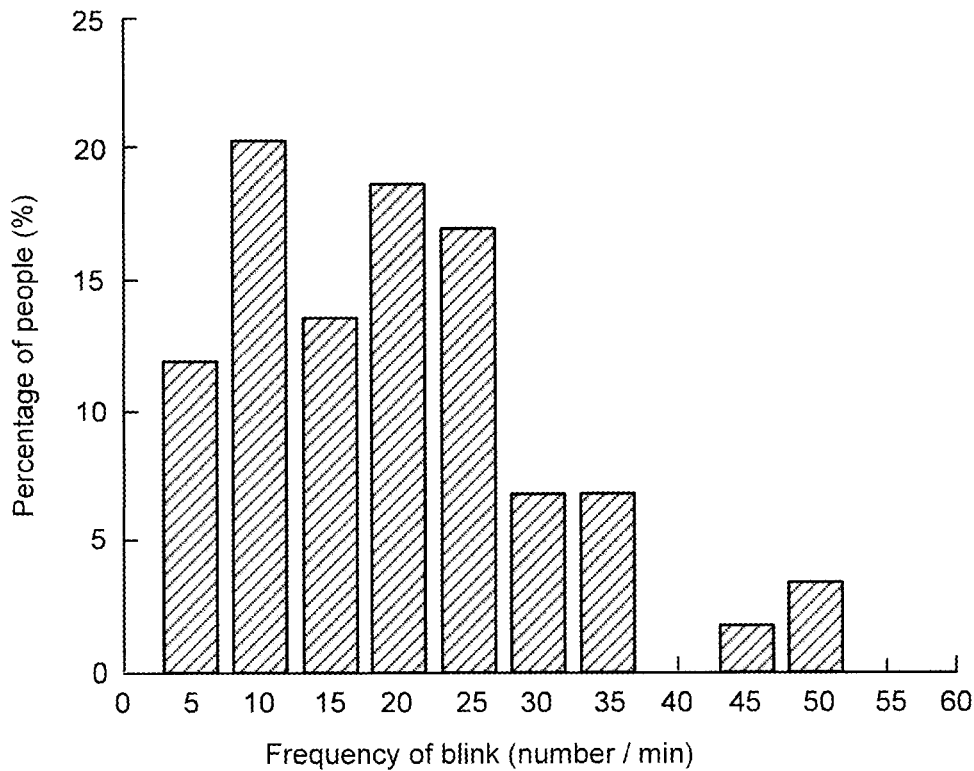
FIG. 33 is a graph illustrating frequency distribution of the blink motion performed by test subjects according to the verification of the fourth embodiment of the present disclosure.

(Video 1) Shogi game explanation
(Video 2) Soccer game
(Video 3) Television Interview with Idol Singer A FIG. 33 is a graph illustrating the frequency distributions of blinks of 59 test watching a video. As illustrated in FIG. 33, the frequency of test subjects blinks ranged from 5 to 50 blinks/min, indicating that there were large differences among individuals. That is, it is difficult to infer whether the blink of a certain number of blinks or frequency is caused by observing a video or is caused by a characteristic of the blink of the person.

Figure 34:
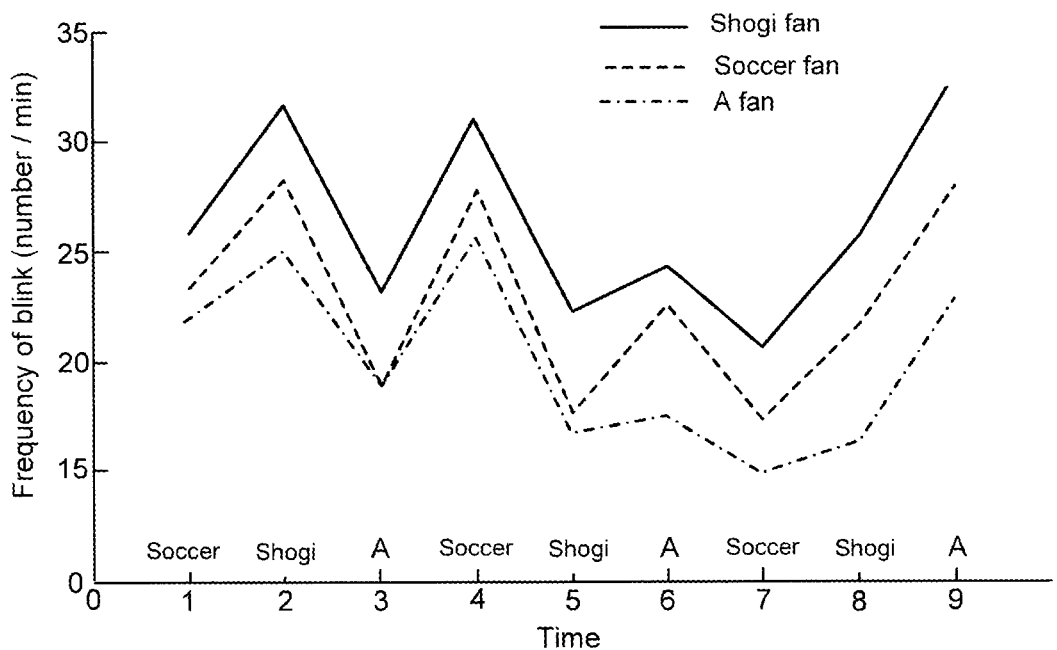
FIG. 34 is a graph illustrating a temporal variation of the number of blinks per minute of test subjects according to the verification of the fourth embodiment of the present disclosure.
Figure 35:
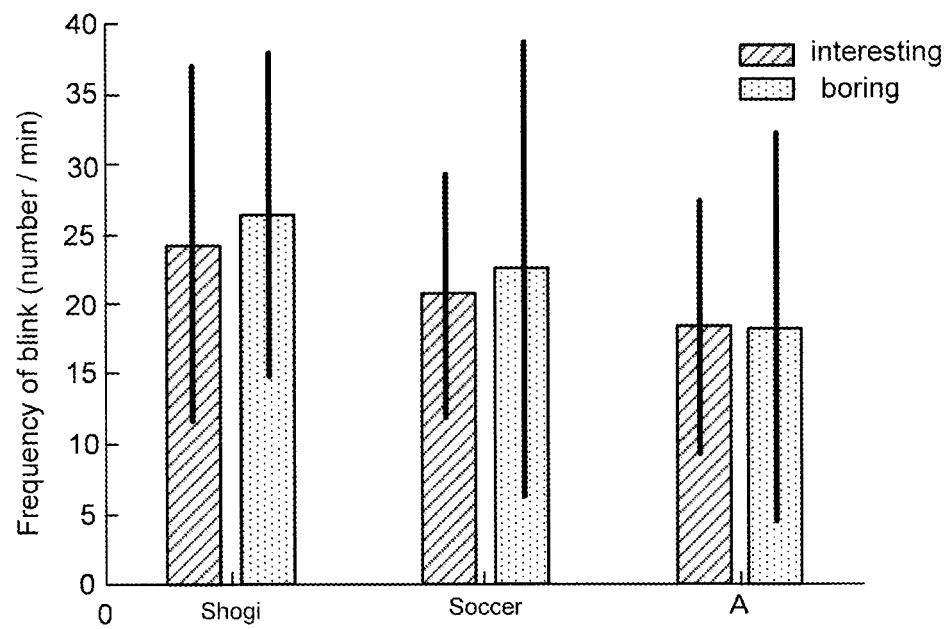
FIG. 35 is a graph illustrating relationship between questionnaire results and the number of blinks after viewing videos according to the verification of the fourth embodiment of the present disclosure.

FIG. 34 is a graph illustrating the temporal variation of the number of blinks per minute of test subjects. FIG. 34 illustrates the average number of test subjects blinks of eight shogi fans, the average number of test subjects blinks of nineteen soccer fans, and the average number of test subjects blinks of eighteen idol singers A fans (denoted as "A fans" in FIGS. 34, 37 and 38), respectively. Among the 59 test subject, there were 12 test subjects responded that they were fans of two or more subjects, shogi and soccer, or soccer and idol singer A (denoted as "A" in FIGS. 34, 37 and 39) in a preliminary questionnaire. For this reason, the 12 test subjects were excluded from test subjects, which are the fans of multiple subjects. As illustrated in FIG. 34, the number of blinks tends to change according to the video. However, no correlations could be identified between the subject of interest and the number of blinks for each subject. FIG. 35 is a graph illustrating the relationship between the result of the poll after watching the video and the number of blinks. As illustrated in FIG. 35, the correlation between the degree of interest in the video and the number of blinks could not be confirmed.

Next, the index calculation processing described above was used to calculate an evaluation value based on the timing difference of test subjects blinks. That is, two users selected from 59 test subjects. The processing of calculating the evaluation value by calculating the timing difference between the blinks of the two selected users was performed for all combinations of users (i.e., as 5902 ways) and the average was calculated. The random data was 1000 ways.

Figure 36:
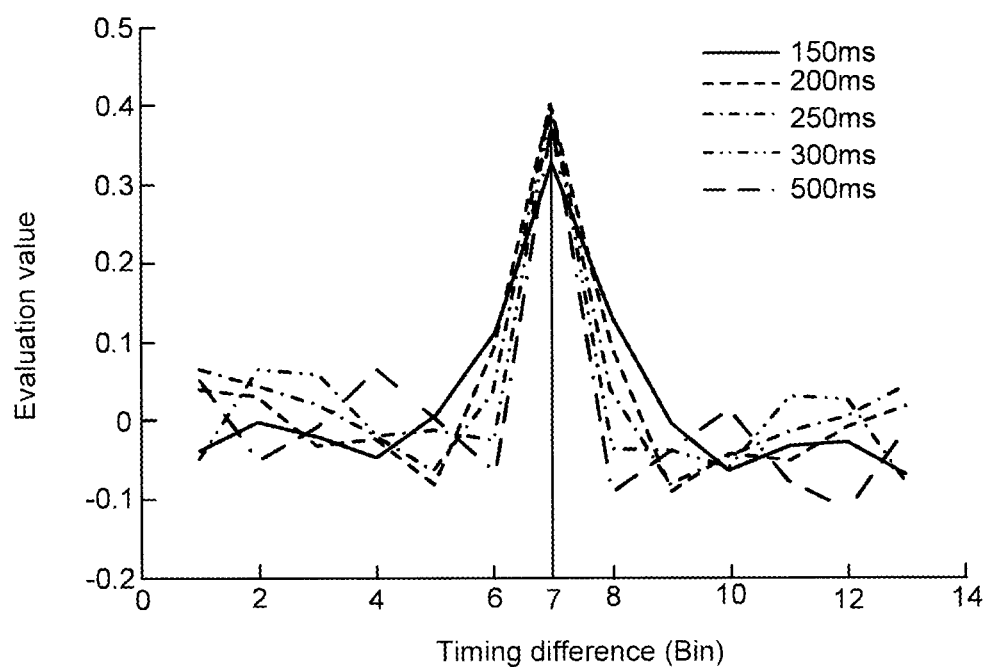
FIG. 36 is a graph illustrating a calculation result of the evaluation values according to the verification of the fourth embodiment of the present disclosure.

FIG. 36 is a graph illustrating the calculation result of the evaluation value according to the present verification. In the graph illustrated in FIG. 36, the horizontal axis corresponds to the timing difference, the vertical axis corresponds to the evaluated value. The timing difference is represented here by the values of the bin. FIG. 36 illustrates graphs in which the time range of the bin number is 150 ms, 200 ms, 250 ms, 300 ms, and 500 ms, respectively. As illustrated in FIG. 36, when the time range of the bin number was any of 150 ms, 200 ms, 250 ms, 300 ms, and 500 ms, it was confirmed that the appearance frequency was locally increased at the bin number "7" where the timing difference of blinks was treated as 0.

Figure 37:
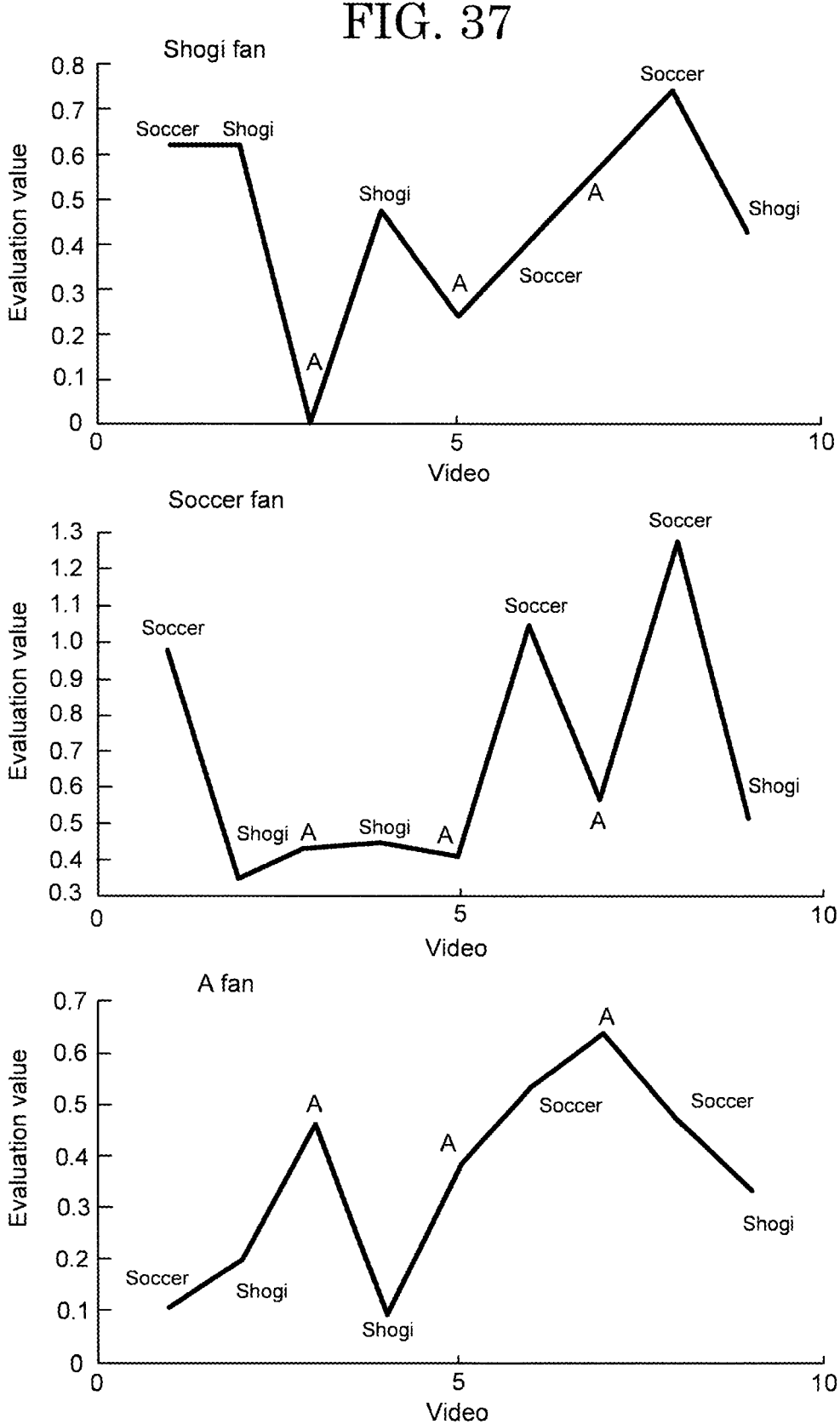
FIG. 37 is graphs illustrating results of calculating evaluation values when viewing each video for each test subject with different interest according to the verification of the fourth embodiment of the present disclosure.

FIG. 37 is a graph illustrating the results of calculation of the evaluation values when each video is viewed for each test subject whose object of interest differs. In the graph illustrated in FIG. 37, the horizontal axis corresponds to the video, the vertical axis corresponds to the evaluation value. As illustrated in FIG. 37, it can be seen that the evaluation value of each of shogi, soccer, and idol singer A is high when the video of the target of interest is observed.

Figure 38:
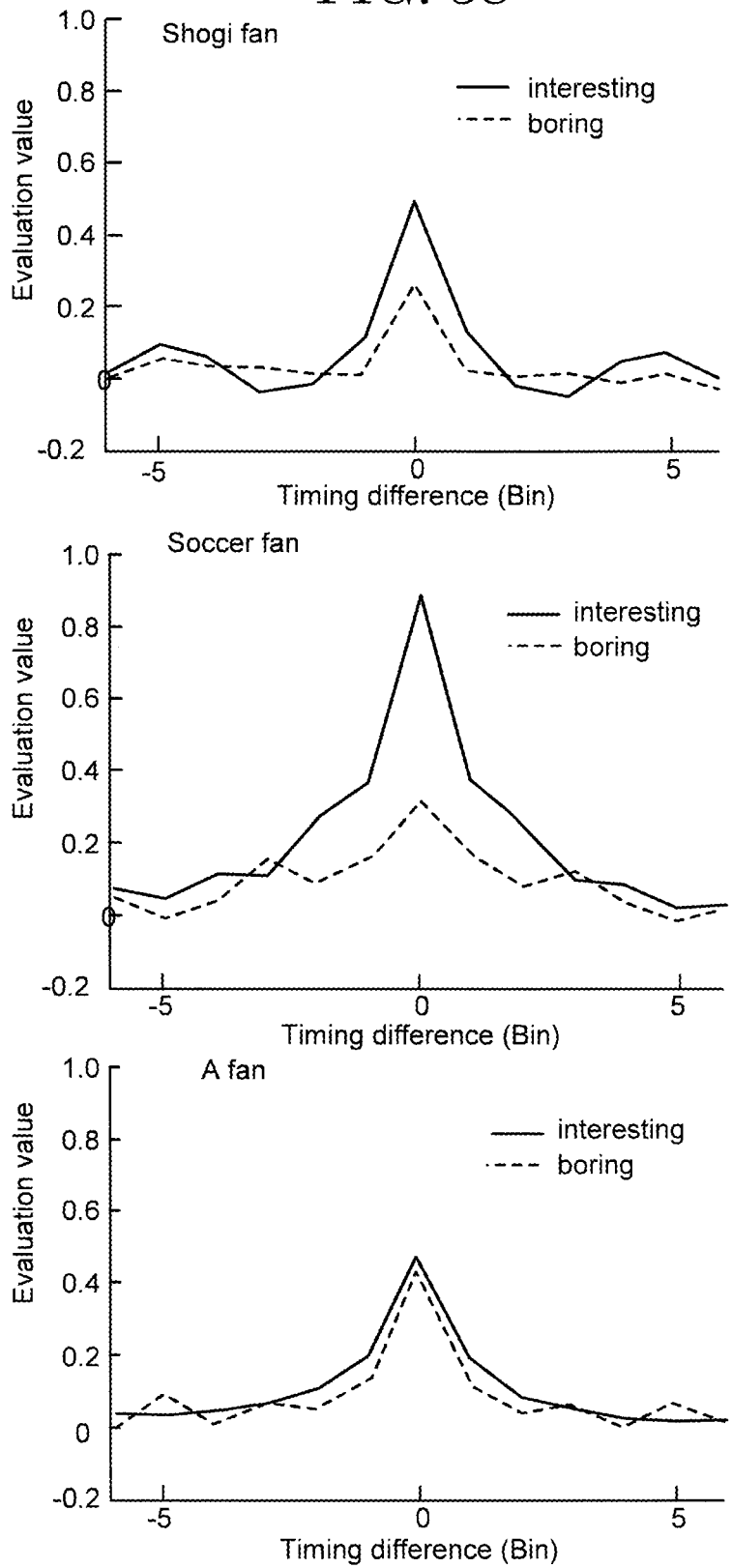
FIG. 38 is graphs illustrating relationships between questionnaire results and evaluation values after watching the videos for all test subjects according to the verification of the fourth embodiment of the present disclosure.

FIG. 38 is a graph illustrating the relation between the questionnaire results and the evaluated values after viewing the respective videos for all test subject. In the graph illustrated in FIG. 38, the horizontal axis corresponds to the timing difference (the value of the bin), the vertical axis corresponds to the evaluation value. As illustrated in FIG. 38, it was found that the degree of increase in the evaluation value was larger in the case of test subject, which felt that the video was interesting, than in the case of test subject, which felt that the evaluation value was boring.

Figure 39:
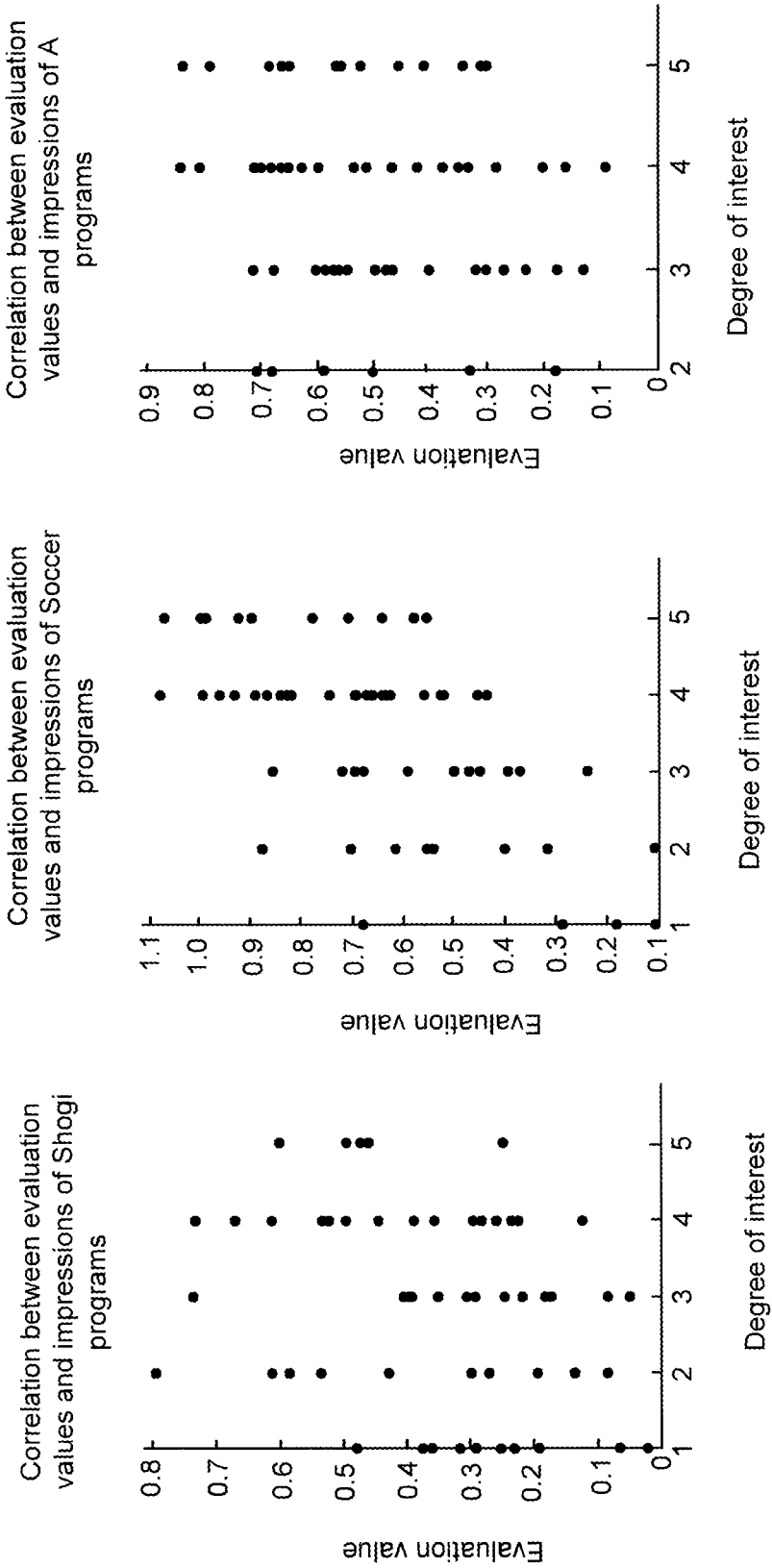
FIG. 39 is graphs illustrating relationships between the impression and the evaluation value after viewing the videos according to the verification of the fourth embodiment of the present disclosure.

FIG. 39 is a graph illustrating a relationship between the impression and the evaluation value after watching a video. In the graph illustrated in FIG. 39, the horizontal axis corresponds to the degree of interest, the vertical axis corresponds to the evaluation value. The degree of interest means that the larger the numerical value is, the more interesting the video is. "r" illustrated in FIG. 39 is the correlation coefficient, and "p" is the probability. Here, for each test subject, the evaluation value is respectively calculated by selecting two persons of test subjects and all other test subjects, the average value of the calculated evaluation value is the evaluation value of test subjects. Also, in this evaluation value, the higher the number of subjects who are interested in the video, the higher the value. From the graphs illustrated in FIG. 39, it was also found that test subjects with the impression that the video is interesting tend to have a higher evaluation value.

As a result of the above verifications, the inventors of the present disclosure were able to obtain the knowledge that the evaluation value corresponding to the timing difference of the blinks of a plurality of users becomes the index of the degree of interest in the video.

<Modifications of the Fourth Embodiment>

(1) The calculation unit 1112 may calculate an evaluation value for each group in which a plurality of users are classified according to a predetermined rule. The rule is a rule that defines a combination of users to calculate an evaluation value. For example, the rule is a user attribute. The user attribute is, for example, a gender, an age, a hobby, a genre of a favorite video of the user, or a combination thereof. The user attributes may be attributes of users other than these attributes. The user attribute may be registered in advance in the server device 1010 and stored in the storage unit 1013. A user of the terminal device 1020 operates the user interface 1022 to enter the user attributes and store them in the storage unit 1024. The transmission unit 1212 may transmit the user attributes to the server device 1010 in association with the blinking data.

Figure 40:
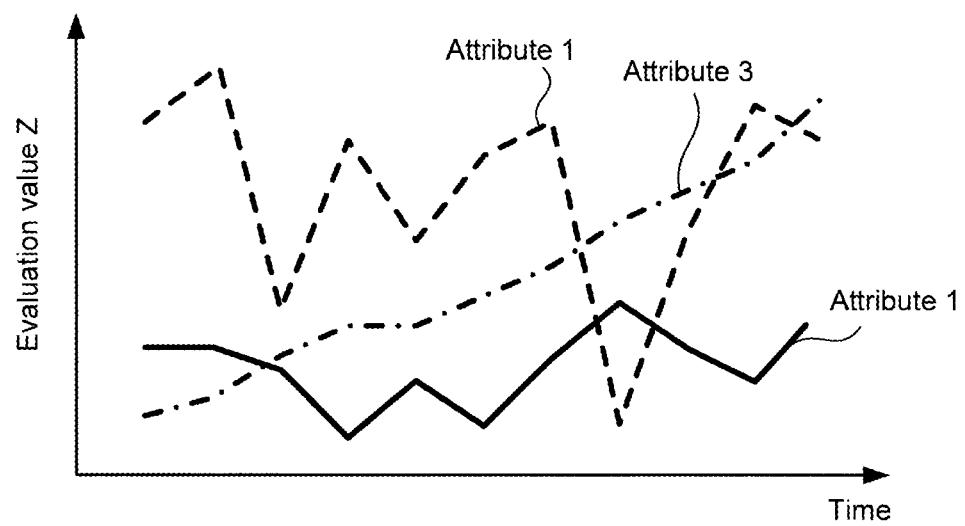
FIG. 40 is a diagram illustrating an example of a data output in step S17 according to a modification of the fourth embodiment of the present disclosure.

The output unit 1113 may further output the data corresponding to the evaluation values for each of the groups. For example, the output unit 1113 may output the data corresponding to the evaluation values for each of the user attributes. FIG. 40 is a diagram illustrating an example of the data output in step S17 of this modification. Here, the output unit 1113 outputs the evaluation values associated with the time for each of the user attributes. In this case, the output unit 1113 generates graphs G1 to G3 in which the horizontal axis corresponds to the time and the vertical axis corresponds to the evaluation value, and the evaluation value changes with time. For example, the graph G1 indicates an evaluation value of a user belonging to "Attribute 1". For example, the graph G2 indicates an evaluation value of a user belonging to "Attribute 2". For example, the graph G3 indicates an evaluation value of a user belonging to "Attribute 3". Therefore, it is possible to understand the temporal change of the evaluation value during watching the video for each user attribute.

(2) The output unit 1113 may output the data for specifying a video whose evaluation value satisfies a predetermined condition. For example, the output unit 1113 may output the data for specifying a video in which many users are interested. The predetermined condition in this case is, for example, that the evaluation value exceeds the threshold or that the evaluation value is the maximum among a plurality of videos. The output unit 1113 may output the data for specifying a period in which the evaluation value satisfies a predetermined condition, among the videos. The predetermined condition in this case is, for example, that the evaluation value exceeds the threshold or that the evaluation value is the maximum among a plurality of videos.

Fifth Embodiment

In the fifth embodiment, a case in which the data processing system according to the present disclosure is applied to a data processing system that performs video lectures is described.

Figure 41:
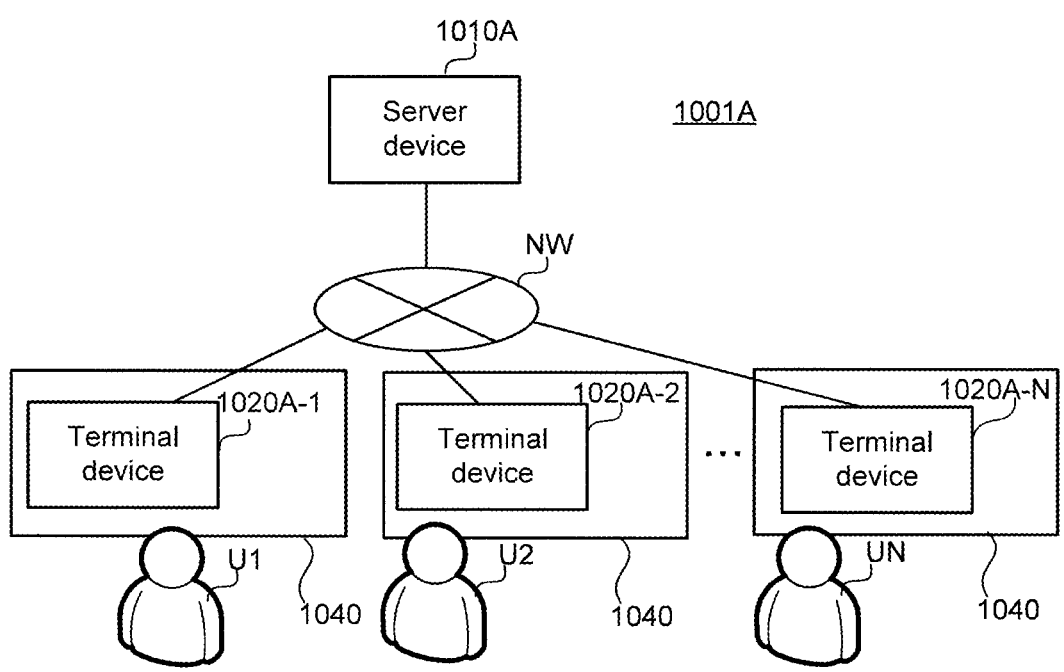
FIG. 41 is a block diagram illustrating an overall configuration of a data processing system according to fifth embodiment of the present disclosure.

FIG. 41 is a diagram illustrating the overall configuration of the data processing system 1001A. The data processing system 1001A includes a server device 1010A and a plurality of the terminal device 1020A. The server device 1010A distributes videos related to lectures such as school lessons, acquires data indicating the blink timing of a user (i.e., a student) from each of the plurality of the terminal device 1020A, and evaluates the videos based on the acquired data. The server device 1010A is managed and operated by, for example, a business person who conducts lectures. The server device 1010A communicates with each of the plurality of the terminal device 1020A via a communication line NW.

The plurality of the terminal device 1020A is used by a user who views videos related to video lectures. Each of the plurality of the terminal device 1020A is pre-installed in a user's seat 1040. The terminal device 1020A is provided at a position where a blink of a user who is watching a video can be detected. In FIG. 41, a plurality of terminal devices 1020A are illustrated as the terminal device 1020A-1, 20 A-2, . . . , 20 A-N, (N is a natural number greater than or equal to 2). For convenience of explanation, the user of the terminal device 1020 A-i (where 1≤i≤N) will be referred to below as "user Ui".

The hardware configuration of the server device 1010A and the hardware configuration of the terminal device 1020A may be the same as the hardware configuration of the server device 1010 and the hardware configuration of terminal device 1020 of the fourth embodiment described above, respectively. However, the storage unit 1013 of the server device 1010A may store the video data indicating the video data when the lecture is performed by playing the video data recorded in advance.

Figure 42:
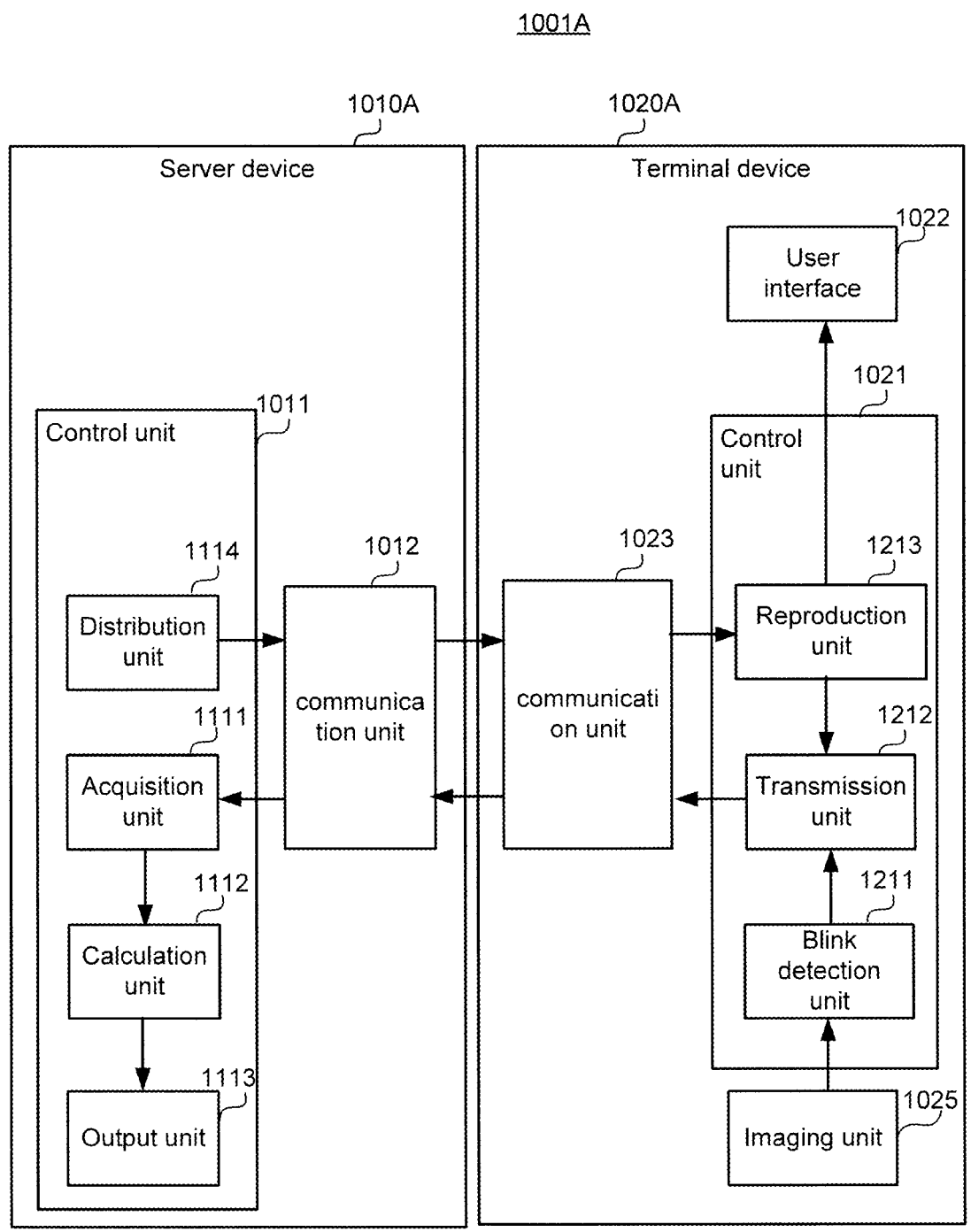
FIG. 42 is a block diagram illustrating a functional configuration of a data processing system according to the fifth embodiment of the present disclosure.

FIG. 42 is a block diagram illustrating a functional configuration of the data processing system 1001A. The control unit 1011 of the server device 1010A executes the programs 1131 to realize functions corresponding to the acquisition unit 1111, the calculation unit 1112, the output unit 1113, and the distribution unit 1114. The distribution unit 1114 distributes a video to each of the plurality of the terminal device 1020A via the communication unit 1012.

The control unit 1021 of each of the plurality of the terminal device 1020A implements functions corresponding to the blink detection unit 1211, the transmission unit 1212, and the reproduction unit 1213 by executing the programs 1241. The reproduction unit 1213 receives a video from the server device 1010A using the communication unit 1023, and reproduces the received video. The reproduced video is displayed to the user via the user interface 1022.

Figure 43:
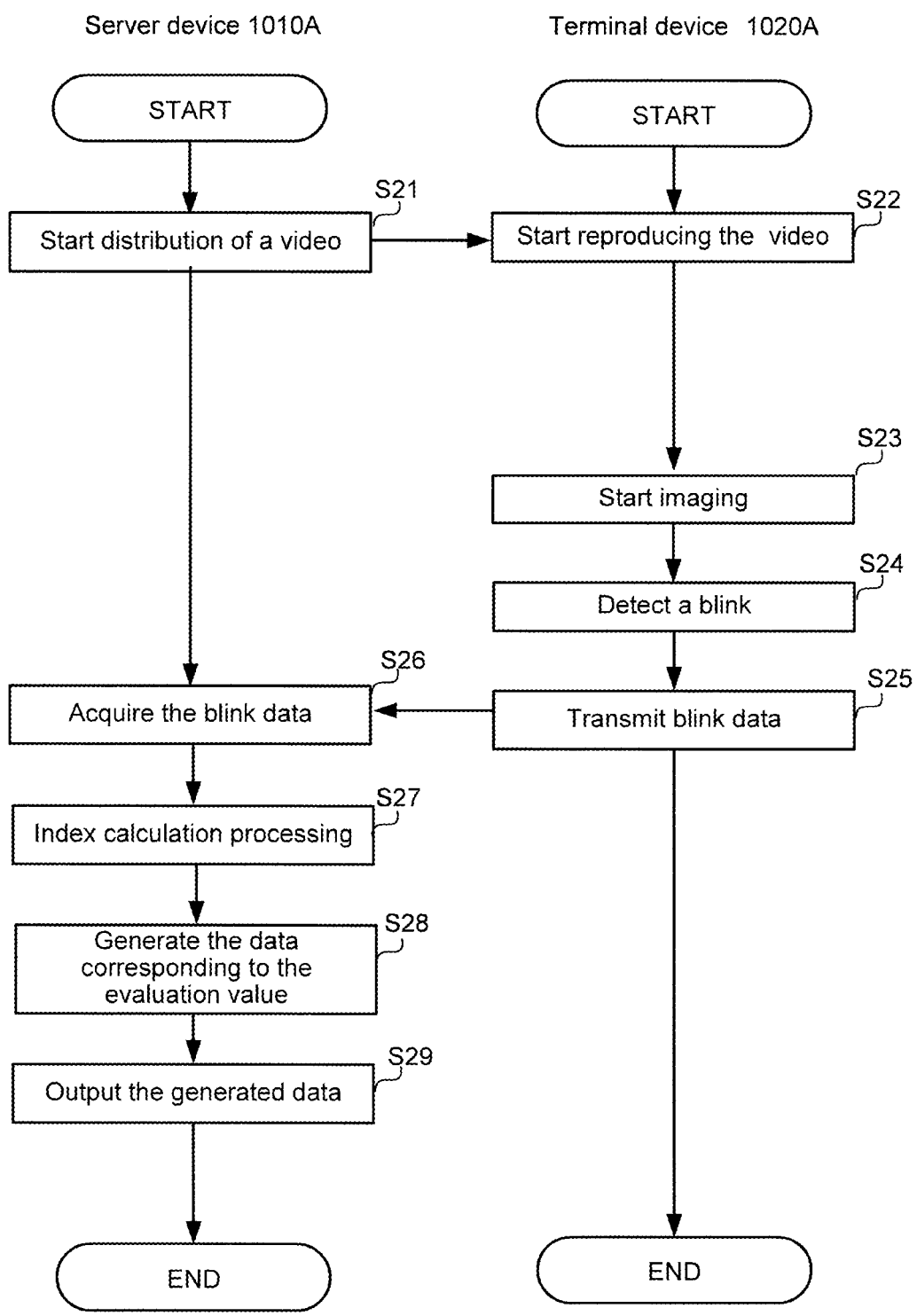
FIG. 43 is a flowchart illustrating a processing executed in the data processing system according to the fifth embodiment of the present disclosure.

Next, the motion of the data processing system 1001A will be described. FIG. 43 is a flowchart illustrating processing executed by the data processing system 1001A.

The distribution unit 1114 of the server device 1010A starts distribution of a video relating to the video lecture (step S21). In the terminal device 1020A, the reproduction unit 1213 receives the video using the communication unit 1023, and starts reproducing the received video (step S22). The blink detection unit 1211 causes the imaging unit 1025 to start imaging (step S23). The blink detection unit 1211 starts detecting a blink of the user based on the image data (step S24). Here, the detection of the blink is started simultaneously with the start of the reproduction of the video, but may be started before the reproduction of the video. The algorithm of the blink detection may be the same as that of the fourth embodiment described above.

The transmission unit 1212 transmits the blink data to the server device 1010A using the communication unit 1023 based on the detection result of the blink (step S25). The timing of the transmission of the blinking data is not limited. The transmission timing may be, for example, a predetermined timing (e.g., after the end of the video lecture) or a timing requested by the server device 1010A.

The acquisition unit 1111 of the server device 1010 acquires the blink data from each of the plurality of the terminal device 1020A (step S26). The calculation unit 1112 performs the index calculation processing based on the blink data acquired by the acquisition unit 1111 (step S27). The index calculation processing may be the same as in the fourth embodiment described above.

The output unit 1113 generates the data corresponding to the evaluation value and outputs the generated data (steps S28 and S29). The output unit 1113 outputs the evaluation value associated with the time. In this case, it is possible to specify a scene that attracts particular interest in the video lecture. The output unit 1113 may output a mean of the evaluation value for the entire duration of the video lecture. The output unit 1113 may generate and output the video data obtained by extracting a scene whose evaluation value satisfies a predetermined condition (e.g., a scene whose evaluation value is equal to or greater than a threshold). This makes it possible to perform school management such as analyzing the content of lectures, and preparing and selecting educational materials. The output unit 1113 may output the evaluation value of the instructor in charge of the video lecture based on the evaluation value. In this case, the output unit 1113 may output the instructor and the evaluation value in association with each other, or may output the instructor by ranking according to the evaluation value.

In the present embodiment, when the instructor and the users U1 to UN are in the same space and the lecture is performed, the control unit 1011 may not have a function corresponding to the distribution unit 1114. The control unit 1021 may not have a function corresponding to the reproduction unit 1213.

The reason why the evaluation value is the index of the degree of interest has been described in the fourth embodiment described above. Furthermore, the inventors verified the visual information as a video relating to the video lecture of the preliminary school. In this verification, 86 high school students were regarded as test subjects, and preliminary tests for solving eight problems handled in video lectures, viewing of videos related to video lectures, and post-test were successively carried out. The post-test is a test for solving eight problems having different conditions such as numbers from the pre-test.

Figure 44:
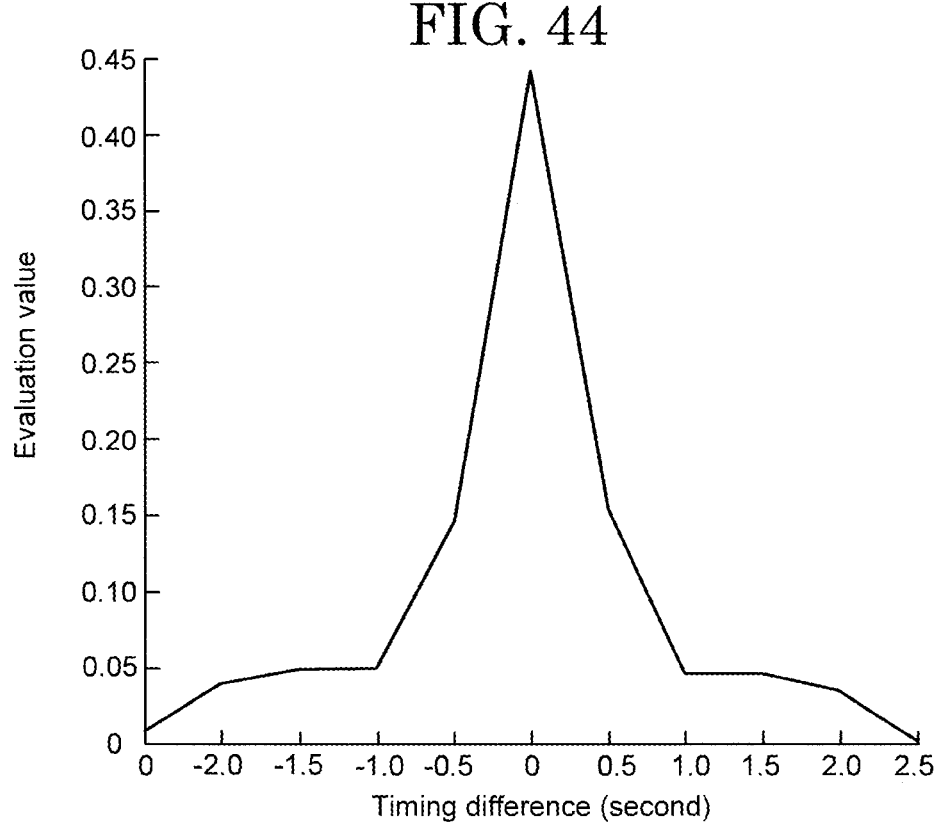
FIG. 44 is a graph illustrating a calculated evaluation value for a video lecture according to the verification of the fifth embodiment of the present disclosure.

FIG. 44 is a graph illustrating the evaluation value in video lectures. In the graph illustrated in FIG. 44, the horizontal axis corresponds to the timing difference, the vertical axis corresponds to the evaluated value. As illustrated in FIG. 44, it was confirmed that the frequency of appearance of the timing difference within a period of approximately 0.25 seconds was locally increased.

Figure 45:
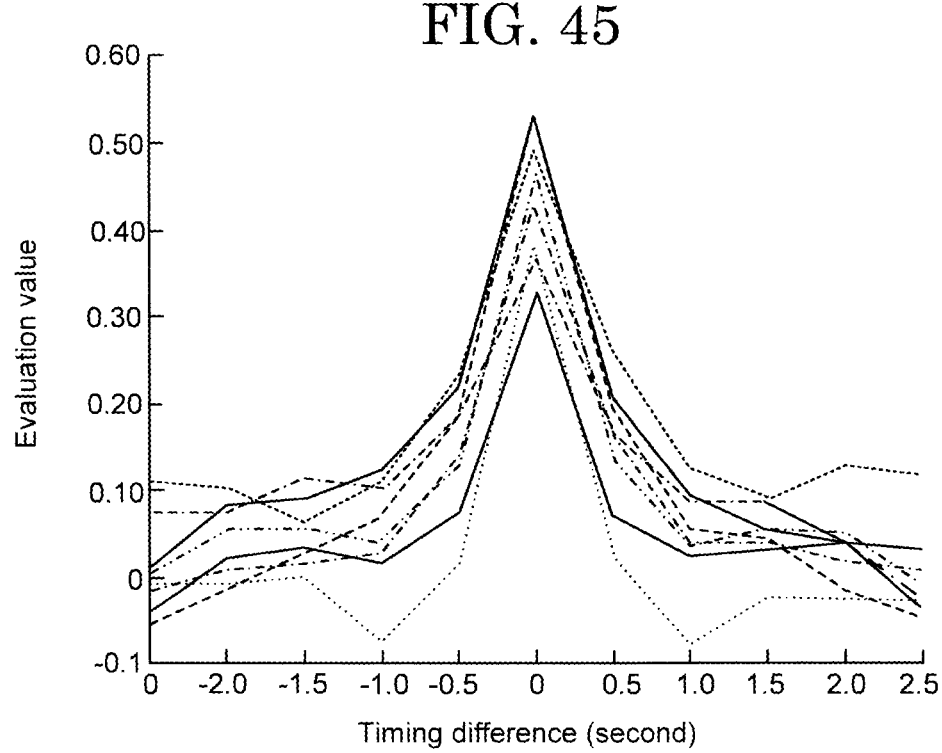
FIG. 45 is a graph illustrating the relationship between questions and the timings of blinking according to the verification of the fifth embodiment of the present disclosure.

FIG. 45 is a graph illustrating evaluation values for each problem. The inventors were able to confirm that the synchronization of the blink timing is slightly different between the problems.

FIG. 46 is a graph showing the relationship between the change of the correct and incorrect answers of the problem and the evaluation value. As illustrated in FIG. 46, the present inventors were unable to confirm the correlation between the correct answer rate and the evaluation value.

Figure 47:
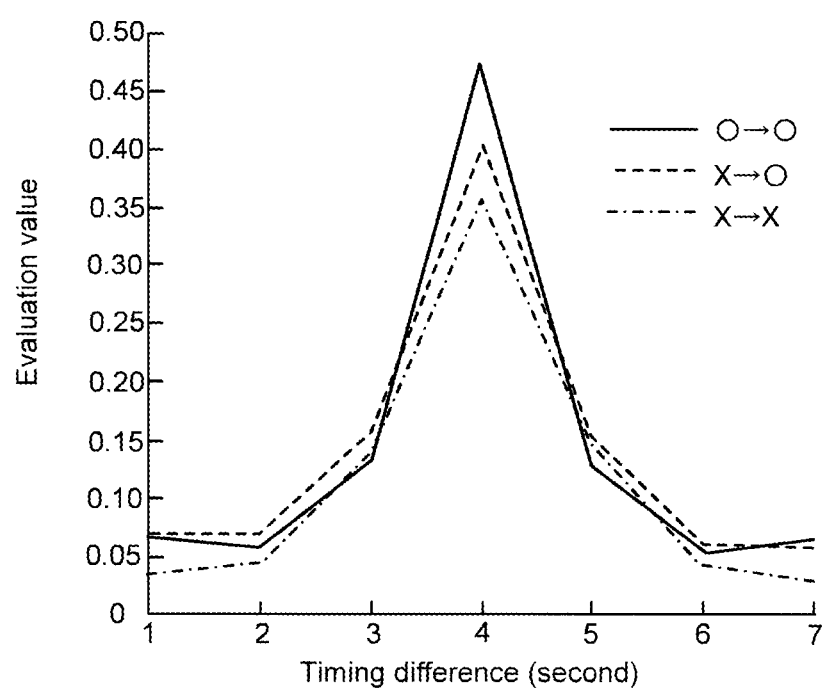
FIG. 47 is a graph illustrating a relationship between the correct answer rate of questions and evaluation values according to the fifth embodiment of the present disclosure.

FIG. 47 is a graph illustrating the relationship between the correct and incorrect answer of the problem and the evaluation value. As illustrated in FIG. 47, The evaluation value is higher in the order of the test subject of correct answers in the preliminary test and the post-test (O→O), the test subject of correct answers in only the post-test (X→O), and the test subject of incorrect answers in the preliminary test and the post-test (X→X). It is considered that the test subject who correctly answered in the post-test was have received video lectures with more interest than the test subject who gave the wrong answer. Therefore, it can be inferred that the higher the degree of interest in the video, the higher the evaluation value tends to be.

Sixth Embodiment

In the sixth embodiment, the case in which the terminal device of the data processing system according to the present disclosure reproduces a video related to television broadcasting will be described.

The overall configuration of the data processing system 1001B is the same as that of the data processing system 1001 of the fourth embodiment described above. However, the data processing system 1001B includes a server device 1010B and a plurality of terminal devices 1020B. The hardware configuration of the server device 1010B and the hardware configuration of terminal device 1020B may be the same as the hardware configuration of the server device 1010 and the hardware configuration of the terminal device 1020 of the fourth embodiment described above, respectively.

Figure 48:
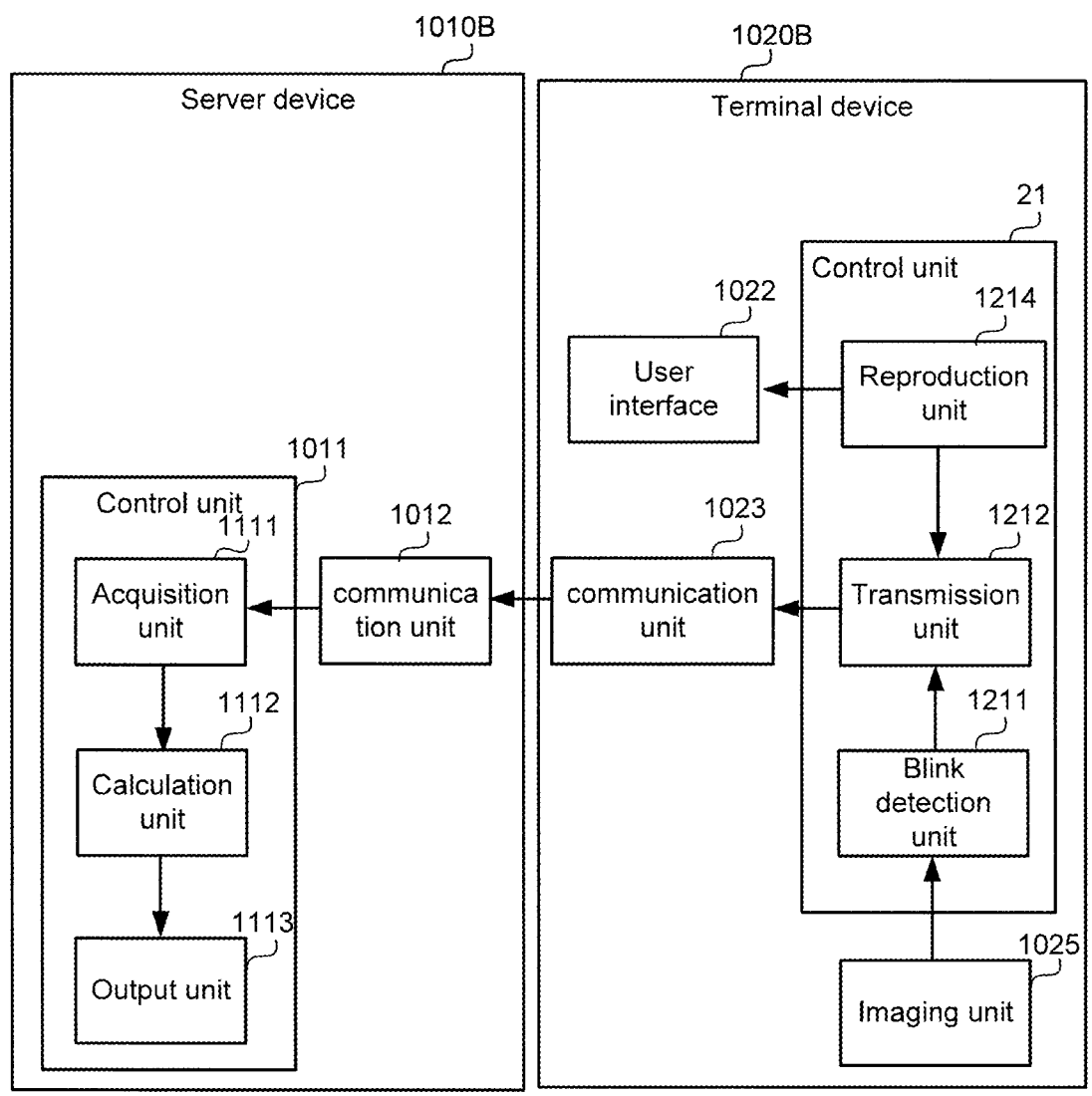
FIG. 48 is a block diagram illustrating a functional configuration of a data processing system according to sixth embodiment of the present disclosure.

FIG. 48 is a block diagram illustrating a functional configuration of the data processing system 1001B. The control unit 1011 of the server device 1010B executes the programs 1131 to realize functions corresponding to the acquisition unit 1111, the calculation unit 1112, and the output unit 1113.

The control unit 1021 of each of the plurality of the terminal devices 1020B implements functions corresponding to the blink detection unit 1211, the transmission unit 1212, and the reproduction unit 1214 by executing the program 1241. The reproducing unit 1214 reproduces a video related to television broadcasting based on the broadcast signal received via the communication unit 1023. The reproduced video is displayed to the user via the user interface 1022.

Figure 49:
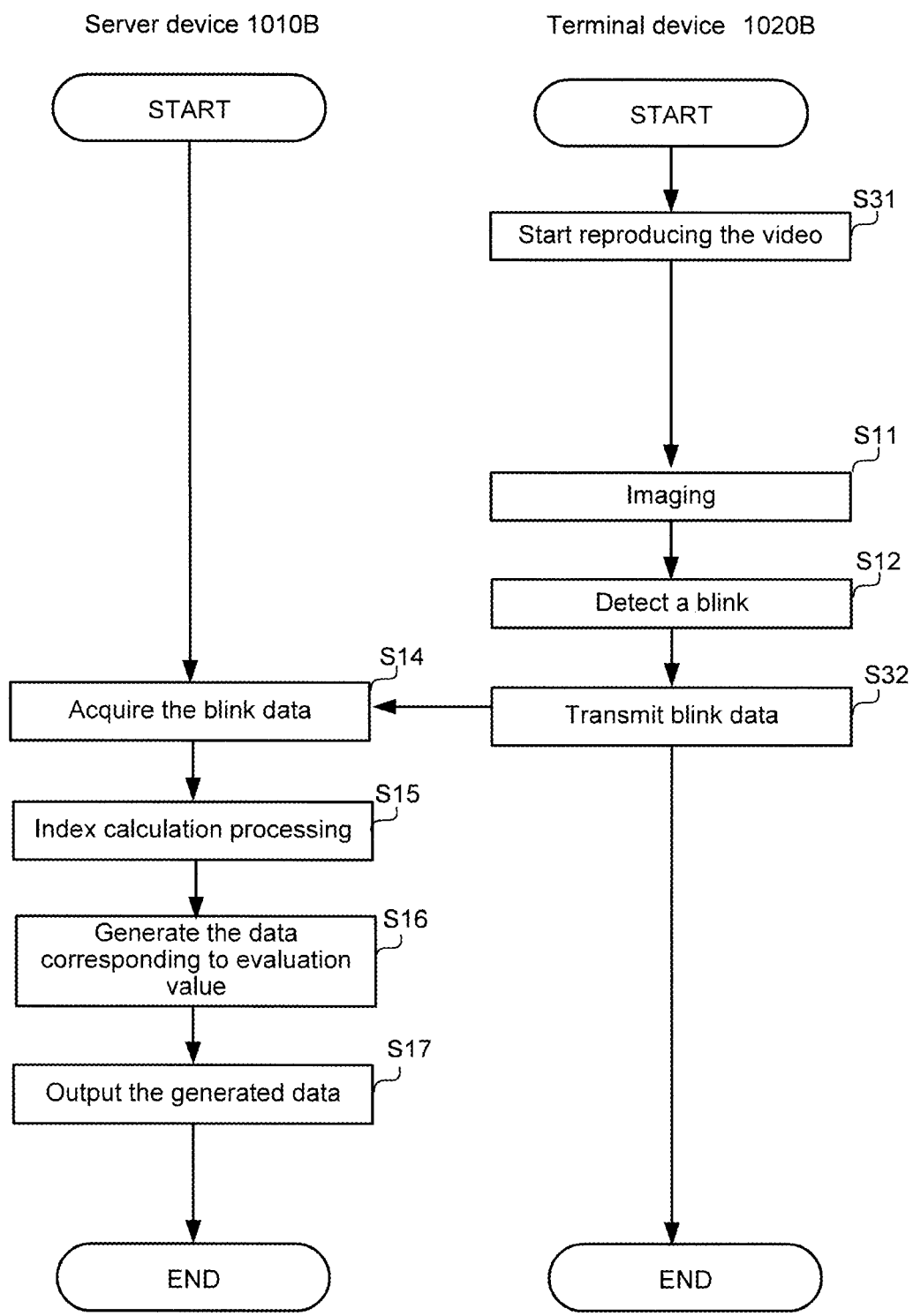
FIG. 49 is a flowchart illustrating a processing executed by a data processing system according to the sixth embodiment of the present disclosure.

Next, the motion of the data processing system 1001 will be described. FIG. 49 is a flowchart illustrating processing executed by the data processing system 1001B.

In the terminal device 1020B, the reproduction unit 1214 receives the broadcast signal using the communication unit 1023, and starts reproduction of a video based on the received broadcast signal (step S31). The blink detection unit 1211 causes the imaging unit 1025 to image the user's eyes and detects the user's blinks based on the imaging data (steps S11 and S12). Here, the detection of the blink is started simultaneously with the start of the reproduction of the video, but may be started before the reproduction of the video. The algorithm of the blink detection may be the same as that of the fourth embodiment described above.

The transmission unit 1212 transmits the blink data indicating the timing of the user's blink to the server device 10108 using the communication unit 1023 (step S32). The transmission unit 1212 may further transmit the video identification information to the server device 10108 in association with the blinking data. The timing of the transmission of the blinking data is not limited. The transmission timing may be, for example, a predetermined timing (e.g., after the end of the television program) or a timing at which a request is received from the server device 10108.

The acquisition unit 1111 of the server device 10108 acquires the blink data from each of the plurality of the terminal device devices 1020B. The calculation unit 1112 performs the index calculation processing based on the blink data acquired by the acquisition unit 1111 (step S15). The index calculation processing in the present embodiment may be the same as the index calculation processing in the fourth embodiment described above. When the terminal device 1020 transmits the video identification information, the acquisition unit 1111 further acquires the video identification information. In addition, the calculation unit 1112 may perform the index calculation processing based on the video identification information in addition to the blink data. The output unit 1113 generates the data corresponding to the evaluation value and outputs the generated data (steps S16 and S17).

Seventh Embodiment

In the fourth to sixth embodiments described above, the visual information is a video. On the other hand, the visual information of the present embodiment is visual information of the outside world. The visual information is, for example, an installation such as an advertisement or a traffic sign. The data processing system of the present disclosure can also be applied to estimate the degree of interest in the visual information of the outside world.

Figure 50:
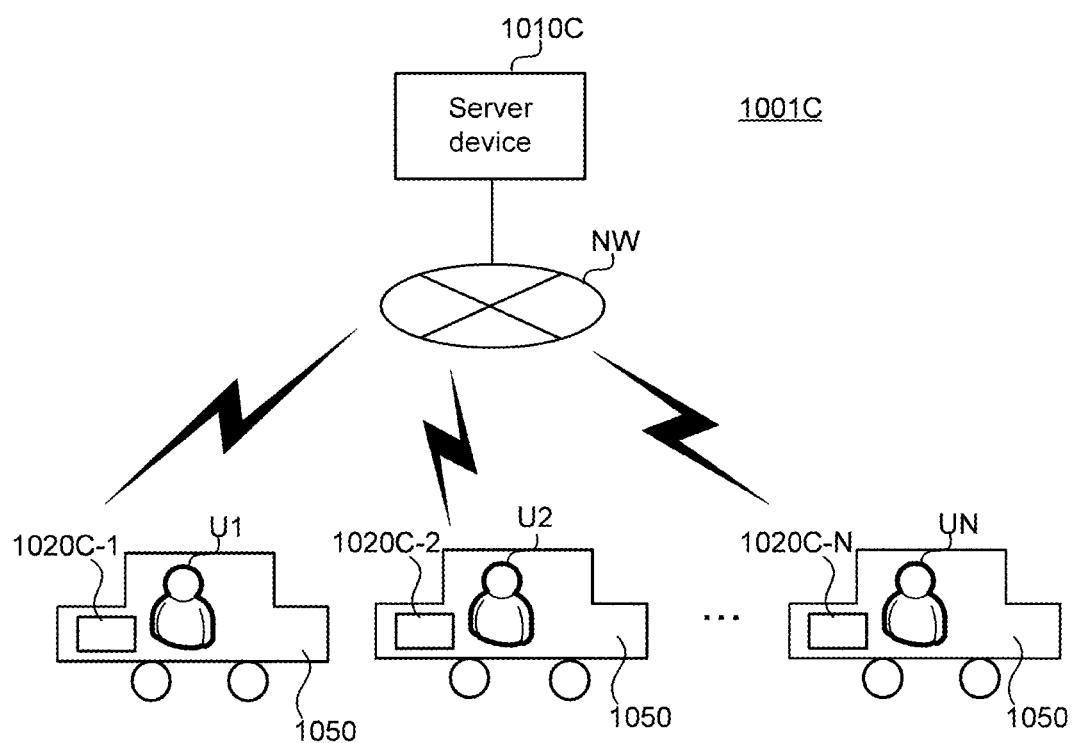
FIG. 50 is a block diagram illustrating an overall configuration of a data processing system according to seventh embodiment of the present disclosure.

FIG. 50 is a diagram illustrating the overall configuration of the data processing system 1001C. The data processing system 1001C includes a server device 1010C and a plurality of the terminal devices 1020C. The terminal device 1020C is, for example, an in-vehicle device, and is installed in the vehicle 1050 in the present embodiment. The terminal device 1020C may be integrated with in-vehicle equipment such as a car navigation system. The vehicle 1050 is here a four-wheeled vehicle (e.g., an automobile), but may also be a two-wheeled vehicle (e.g., a motorcycle) or another vehicle. The terminal device 1020C is provided at a position where the blink of a user, for example, a driver, can be detected. In FIG. 50, the terminal device 1020C-1, 1020 C-2, . . . , 1020C-N (where N is a natural number of 2 or more) is illustrated as a plurality of the terminal device 1020C. For convenience of explanation, a user of the terminal device 1020C-i (where 1≤i≤N) will be referred to below as "user Ui".

The hardware configuration of the server device 1010C may be the same as that of the server device 1010 of the fourth embodiment described above.

Figure 51:
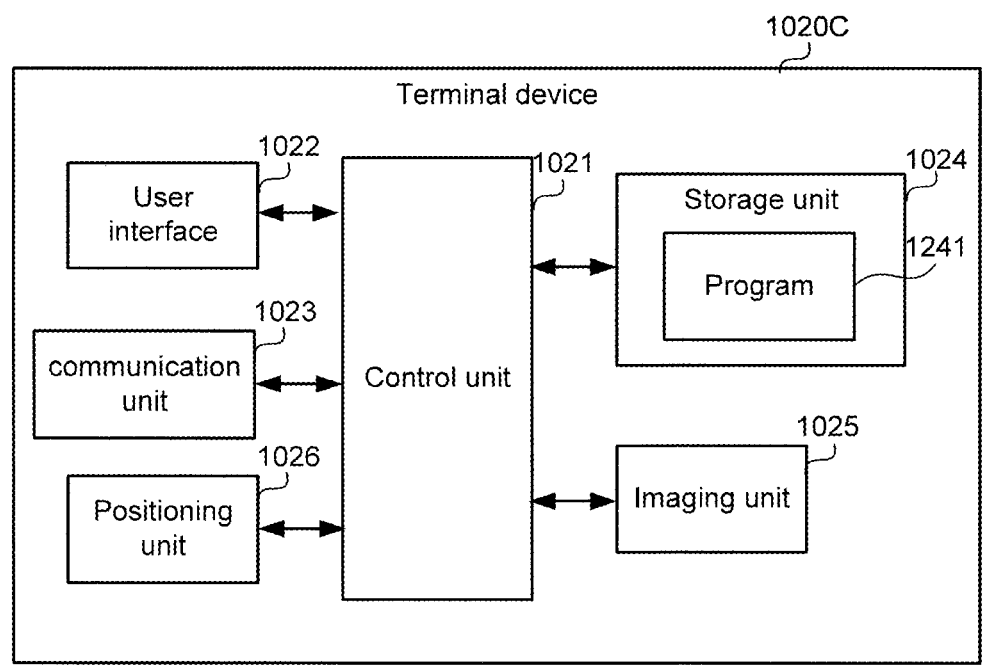
FIG. 51 is a block diagram illustrating a hardware configuration of a terminal device according to the seventh embodiment of the present disclosure.

FIG. 51 is a block diagram illustrating the hardware configuration of the terminal device 1020C. The terminal device 1020 C differs from the terminal device 1020 of the fourth embodiment described above in that it has a positioning unit 1026. The positioning unit 1026 measures the position of the terminal device 1020C and generates location information. For example, the positioning unit 1026 includes a reception circuit and antennas for positioning in a GPS (Global Positioning System) manner. In this case, the positioning unit 1026 generates a location information including latitude information and longitude information. However, the positioning unit 1026 may perform positioning using methods other than GPS, such as base station positioning.

Figure 52:
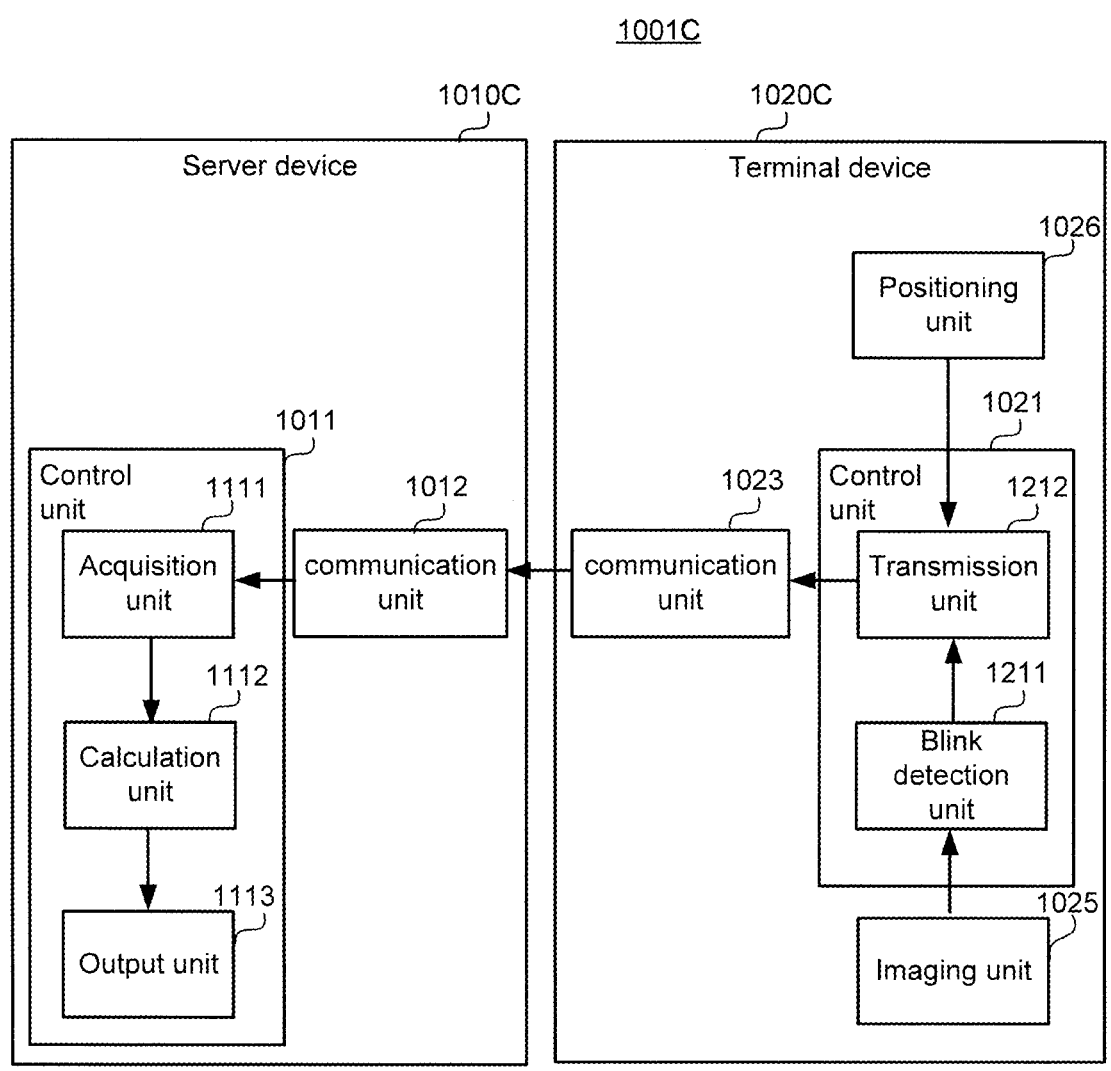
FIG. 52 is a block diagram illustrating a functional configuration of a data processing system according to the seventh embodiment of the present disclosure.

FIG. 52 is a block diagram illustrating a functional configuration of the data processing system 1001C. The control unit 1011 of the server device 1010C executes the programs 1131 to realize functions corresponding to the acquisition unit 1111, the calculation unit 1112, and the output unit 1113. The control unit 1021 of each of the plurality of the terminal device 1020C implements functions corresponding to the blink detection unit 1211 and the transmission unit 1212 by executing the programs 1241. The transmission unit 1212 transmits the blink data indicating the blink timing and the location information indicating the position of the terminal device 1020C when the blink is detected to the server device 1010C. The calculation unit 1112 calculates an evaluation value for each position at which a plurality of users blink. The output unit 1113 outputs the data corresponding to the evaluated data in association with the position.

Figure 53:
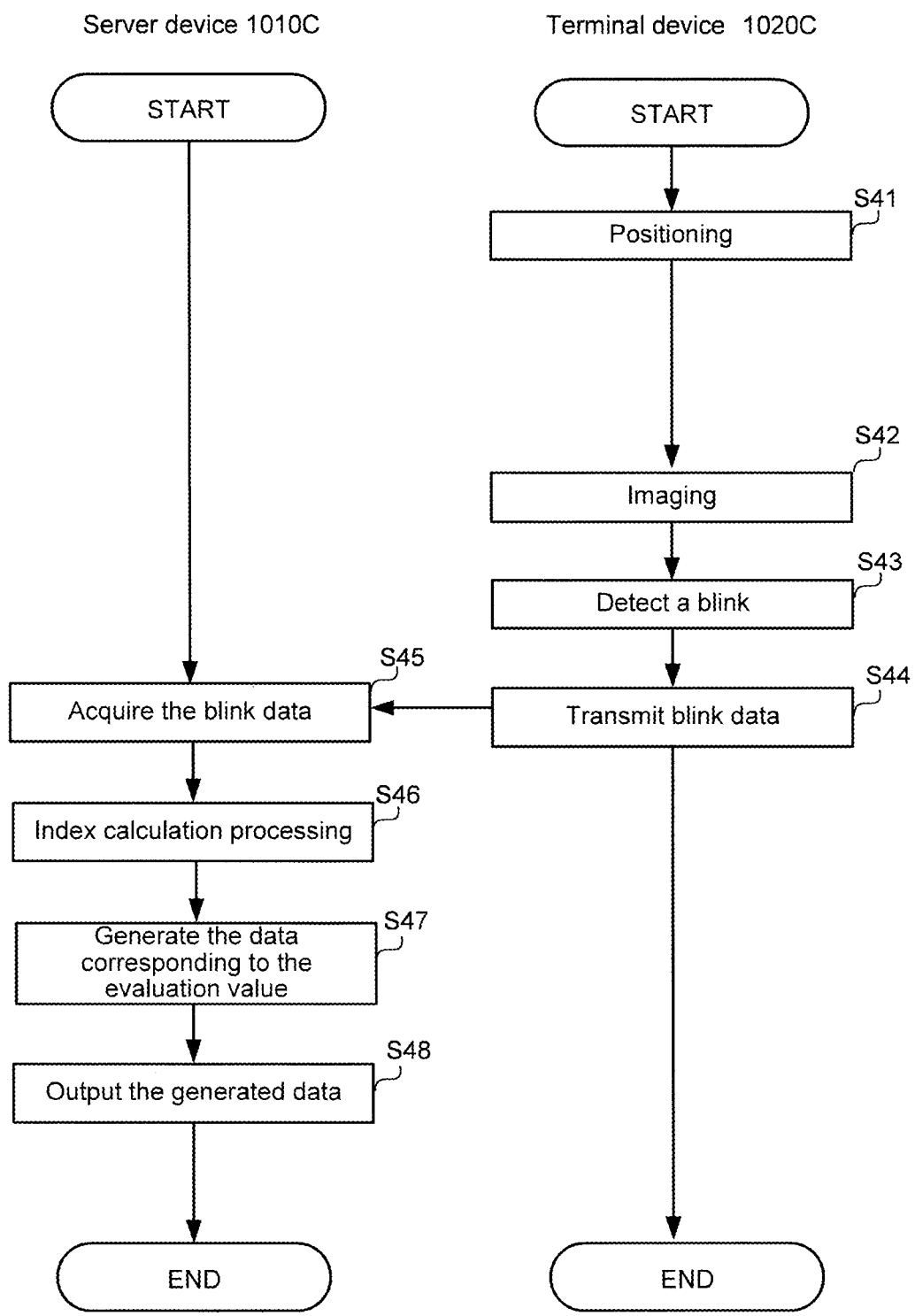
FIG. 53 is a flowchart illustrating a processing executed by a data processing system according to the seventh embodiment of the present disclosure.

Next, the processing of the data processing system 1001C will be described. FIG. 53 is a flowchart illustrating processing executed by the data processing system 1001C.

The positioning unit 1026 starts positioning (step S41). The blink detection unit 1211 causes the imaging unit 1025 to image, and detects the blink of the user (steps S42 and S43). For example, the blink detection unit 1211 detects the blink of the user while the vehicle 1050 running or while the vehicle navigation device is being used.

The transmission unit 1212 associates the location information generated by the positioning unit 1026 with the blink data indicating the timing of the user's blink, and transmits them to the server device 1010C using the communication unit 1023 (step S44). For example, the blink data indicates the timing of the blink on the time axis at which the time when the terminal device 1020C (i.e., the vehicle 1050) enters a certain region is set as the starting point of the blink data. The location information and the blink data may be transmitted at any timings. For example, the transmission timing may be a predetermined timing (e.g., every predetermined period) or a timing at which a request is received from the server device 1010C.

The acquisition unit 1111 of the server device 1010C acquires the location information and the blink data from each of the plurality of terminal devices 1020C (step S45). The calculation unit 1112 performs the index calculation processing based on the blink data acquired by the acquisition unit 1111 (step S46). In the present embodiment, the calculation unit 1112 calculates an evaluation value based on a timing difference of blink of a plurality of users according to positions.

Figure 54:
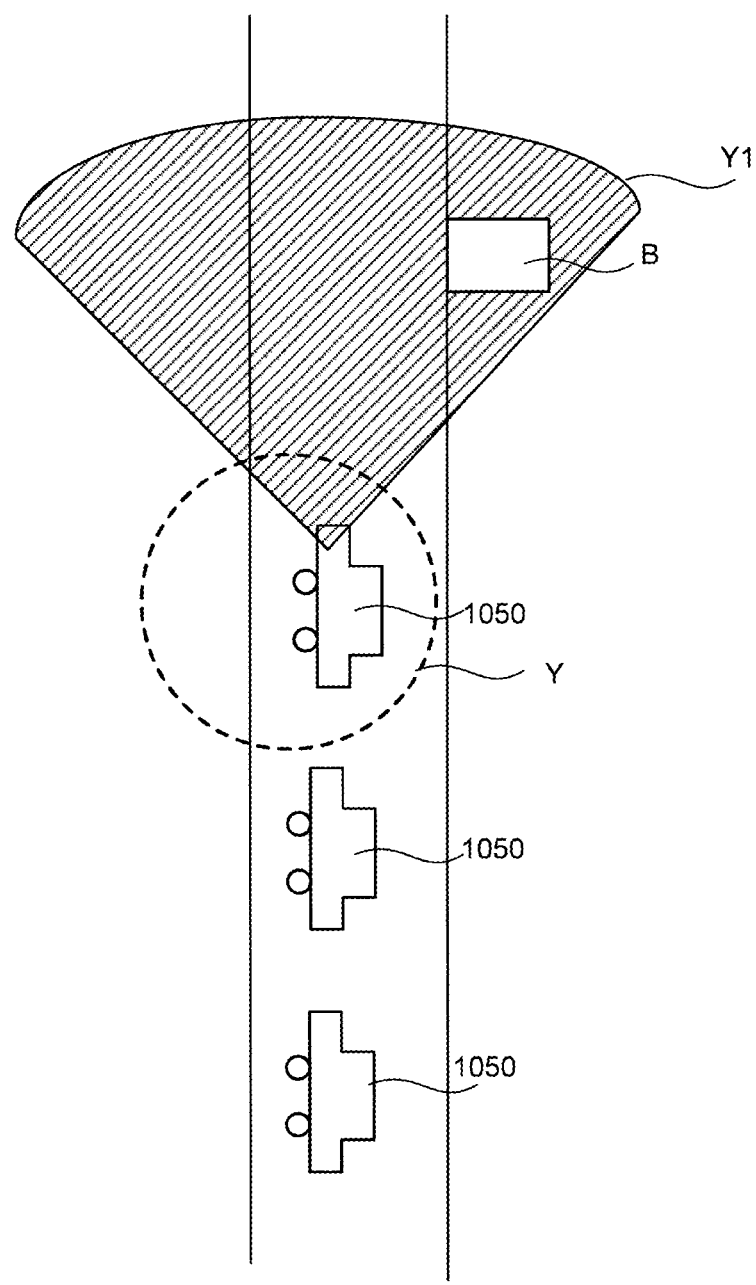
FIG. 54 is a diagram illustrating a processing executed by a data processing system according to the seventh embodiment of the present disclosure.

FIG. 54 is a diagram illustrating processing executed by the data processing system 1001C. As illustrated in FIG. 54, the calculation unit 1112 calculates an evaluation value based on, for example, a detection result of blinks of a plurality of users within a predetermined region Y. This makes it possible to evaluate the degree of the interest about whether the visual information which the user interest is high exists within the region Y1, which can be observed from the region Y. The positions and ranges of the region Y and Y1 may be predetermined. The region Y may be determined with reference to the position of a user.

Figure 55:
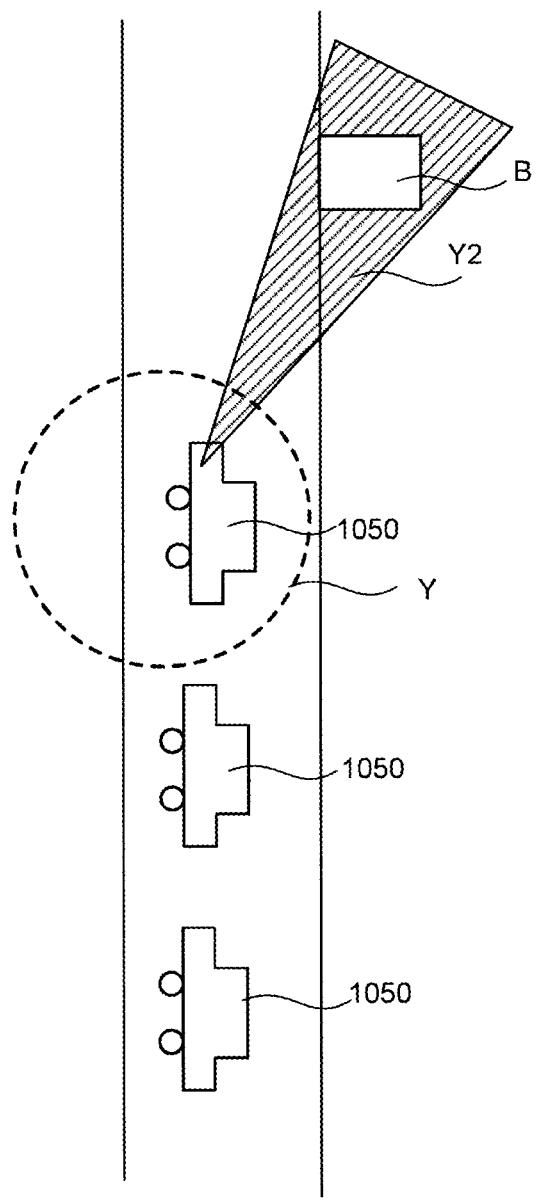
FIG. 55 is a diagram illustrating a processing executed by a data processing system according to the seventh embodiment of the present disclosure.

The output unit 1113 generates the data corresponding to the evaluation value and outputs the generated data (steps S47 and S48). As illustrated in FIG. 55, for example, the output unit 1113 outputs the data DO which associates location information with an evaluation value. As a result, it is possible to understand that the location of the visual information that the user is interested in during riding the vehicle 1050. For example, if the degree of the interest level to the signboard B is high, the evaluation value associated with location information indicating the position in the region Y will be high. Therefore, the advertising effect of the signboard B can be quantitatively grasped. The positions with high evaluation values may have causes of obstruction of traffic. Therefore, the evaluation value can also be used for grasping the cause. If the evaluation value is low in a region where advertisements or traffic signs can be observed, it can also be used to review the installation location. The output unit 1113 may provide information according to the location information and the evaluation value to a user who is an occupant (here, a driver) of the vehicle 1050. For example, the output unit 1113 associates the position information indicating the position of the vehicle 1050 with the evaluation value, and stores the evaluation value in the storage unit 1013. Then, the output unit 1113 identifies a target in which a plurality of users are interested based on the correlation between the evaluation value stored in the storage unit 1013 and the location information, and transmits the information corresponding to the target to the terminal device 1020C. In this case, the output unit 1113 may specify the terminal device 1020C of the vehicle 1050 existing at the position corresponding to the target vehicle as the destination. For example, if it is found that a plurality of users are focusing on the same store (e.g., a convenience store), the output unit 1113 transmits the information about the store (e.g., store information and contents exemplified by coupons) to the terminal device 1020C of the vehicles 1050 present in the vicinity of the store. This allows other users to share information about the target of the interest from a plurality of users.

Figure 56:
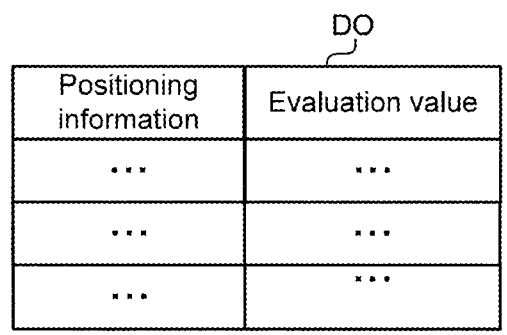
FIG. 56 is a diagram illustrating an example of a data output in step S48 according to a modification of the seventh embodiment of the present disclosure.

The calculation unit 1112 may generate a group of users to be used for the calculation of the evaluation value based on the blink data of the plurality of users and the visual line direction of the plurality of users. The control unit 1011, for example, based on the imaging data of the imaging unit 1025, detects the visual line direction of the user. The plurality of users whose positions and visual line directions are coincident or similar may be observing the same visual information. Therefore, by using the blink data and the visual line direction in combination, a plurality of users who observe the same visual information can be easily classified into the same group. As a result, as illustrated in FIG. 56, it can also be inferred that the visual data that attracts the user's interest exists in region Y2 that is narrower than region Y1.

[Modification]

The present disclosure is not limited to the above-described embodiments, and can be appropriately modified within a range not departing from the spirit thereof. The following modifications can be applied to the configurations of the fifth to seventh embodiments unless otherwise specified.

(1) The visual information may not be a video. For example, the visual information may be contents including visually recognizable information, such as letters, graphics, photographs, etc. such as news articles. The visual information in this case, for example, the information that can be recognized through the vision changes according to the operation of the user. In this variant, the calculation unit 1112, based on the visual information displayed on the terminal device 1020 and the blink detected during displaying the visual information, the calculation unit 1112 calculates the evaluation value for the visual information. This allows content providers to understand the degree of interest in content based on their evaluation values.

Figure 57:
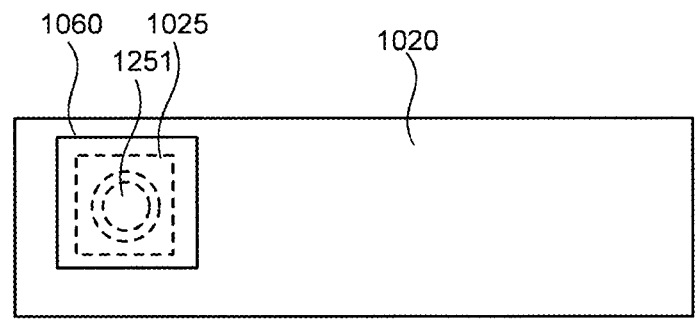
FIG. 57 is a schematic front view of an imaging unit according to a modification of the present disclosure.

(2) When the user is imaged by the imaging unit 1025, the user may feel resistance to it. Therefore, a member that prevents the imaging unit 1025 from being visually recognized by the user may be provided. FIG. 57 is a schematic front view of the imaging unit 1025 according to this modification. In this embodiment, the one-way mirror 1060 is provided so as to cover the imaging lens 1251 provided on the imaging unit 1025. The one-way mirror 1060 is a member that transmits light from the user side to the imaging lens 1251, but does not transmit light from the imaging lens 1251 side to the user side. This reduces the resistance feeling of the user.

Figure 58:
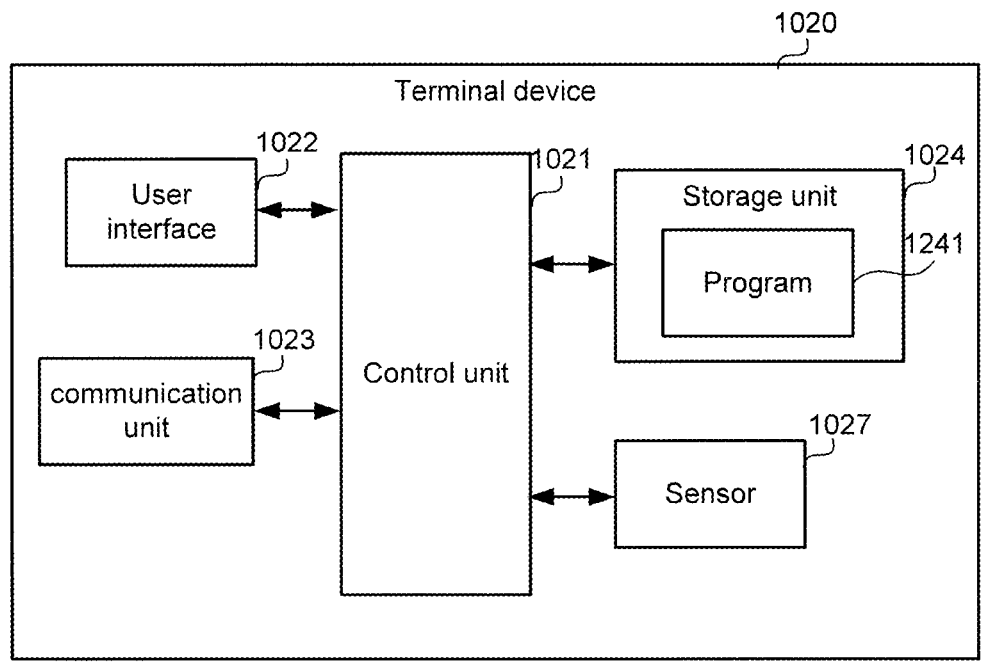
FIG. 58 is a block diagram illustrating a hardware configuration of a terminal device according to a modification of the present disclosure.

(3) In the embodiment described above, the blink is detected based on the imaging data of the imaging unit 1025, but other methods may be used. As illustrated in FIG. 58, for example, the terminal device 1020 may detect blinks using a non-contact sensor 1027, such as a radio sensor (e.g., a 4 GHz radio sensor module), an infrared sensor, a Doppler sensor, in place of the imaging unit 1025. If the terminal device 1020 is a terminal device installed on the face or the head of a user, such as a spectacle-type wearable computer, the sensor 1027 may be a sensor that detects blink based on the motion of muscle strength, etc.

Figure 59:
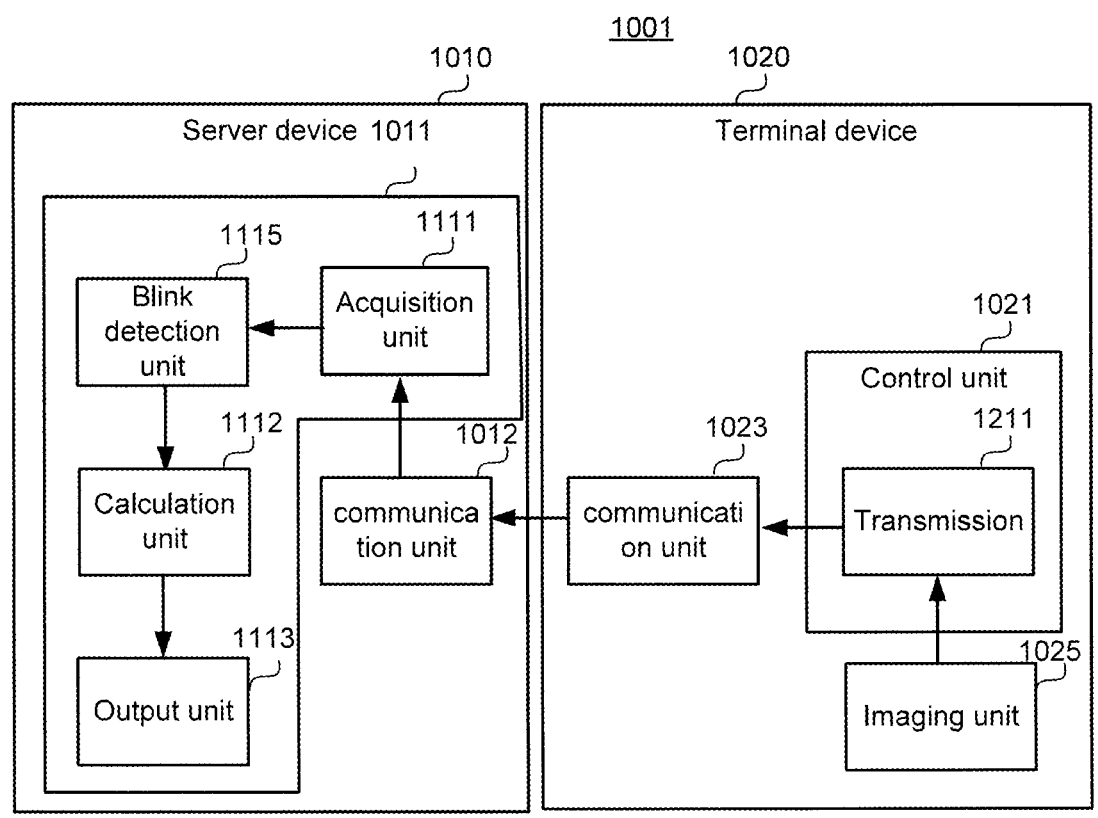
FIG. 59 is a block diagram illustrating a functional configuration of a data processing system according to a modification of the present disclosure.

(4) In the embodiment described above, the terminal device 1020 detects a blink, but it may be executed by the server device 1010. FIG. 59 is a block diagram illustrating a functional configuration of a data processing system according to this modification. In the terminal device 1020, the transmission unit 1212 transmits the imaging data of the imaging unit 1025 to the server device 1010 using the communication unit 1023. In the server device 1010, the control unit 1011 realizes functions corresponding to the acquisition unit 1111, the blink detection unit 1115, the calculation unit 1112, and the output unit 1113. The acquiring unit 1111 acquires the imaging data from the terminal device 1020. The imaging data is a data indicating the blink timing by the user. The blink detection unit 1115 detects the blink of the user based on the imaging data acquired by the acquisition unit 1111.

Figure 60:
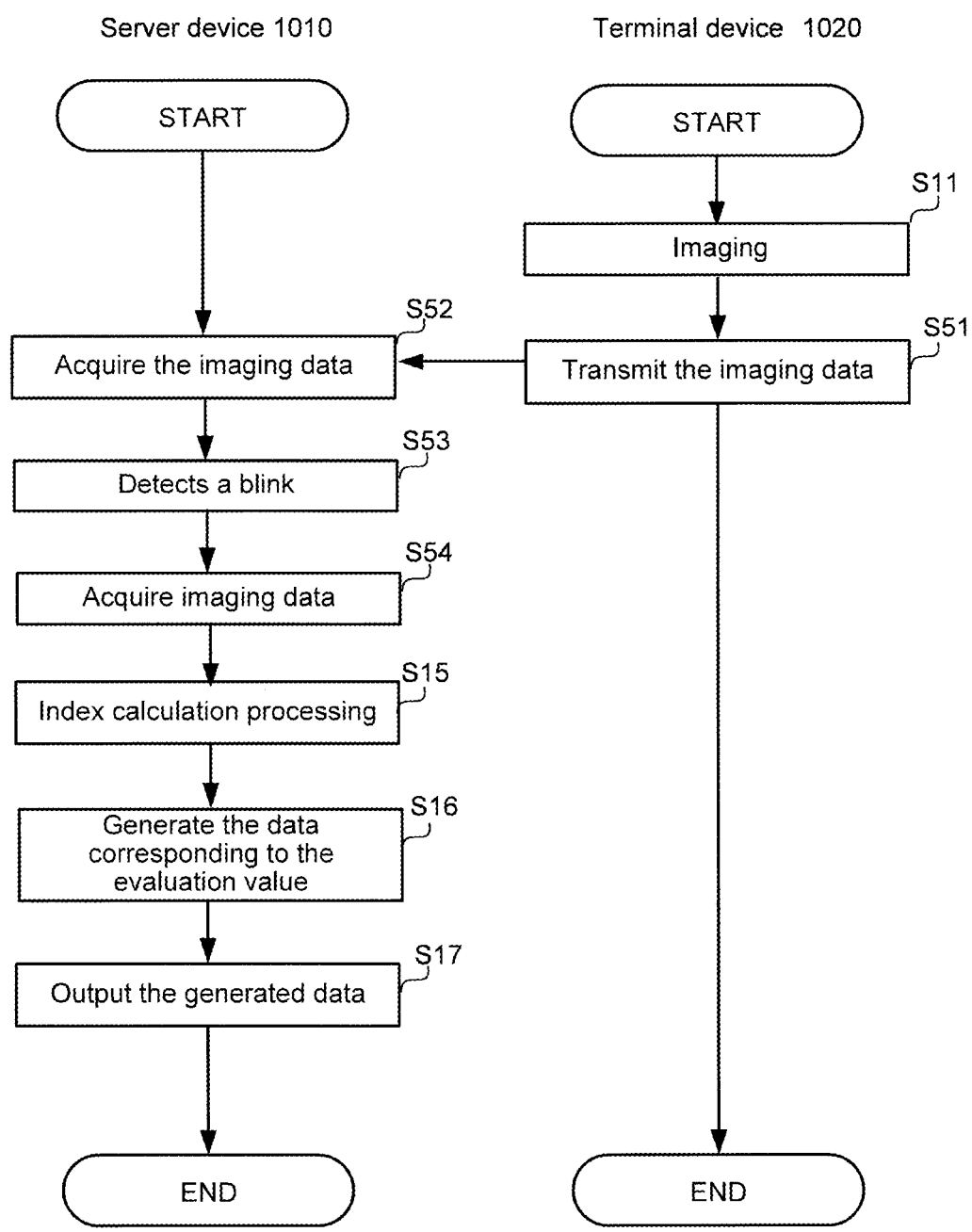
FIG. 60 is a flowchart illustrating a processing executed by a data processing system according to a modification of the present disclosure.

FIG. 60 is a flowchart illustrating a processing performed by the data processing system 1001. In the terminal device 1020, the transmission unit 1212 transmits the imaging data obtained by the image capturing to the server device 1010 using the communication unit 1023 (steps S11 and S51). The acquisition unit 1111 of the server device 1010 acquires the imaging data as the data indicating blink timing by the user (step S52). The blink detection unit 1115 detects a blink of the user based on the acquired imaging data (step S53). The calculation unit 1112 performs the index calculation processing based on the blink data corresponding to the detection result of the blink detection unit 1115 (step S15). The output unit 1113 generates and outputs the data corresponding to the calculated evaluation values (steps S16 and S17).

A the s described above, the data indicating the timing of the blink of the user acquired by acquisition unit 1111 may be the blink data described above, or may be the data for specifying the blink data exemplified by the imaging data.

(5) The calculation method of the evaluation value of the calculation unit 1112 of the embodiment described above is merely an example. For example, the calculation unit 1112 may count the number of blinks in time series and calculate the evaluation value based on the number of blinks in a specific period (scene). In this case, the calculation unit 1112 calculates an evaluation value indicating that the degree of interest in the visual information is higher in the period in which the number of blinks of the plurality of users is larger. This is because it is considered that the timing difference of blink is smaller in the period in which the number of blinks of the plurality of users is larger than in other periods.

Figure 61:
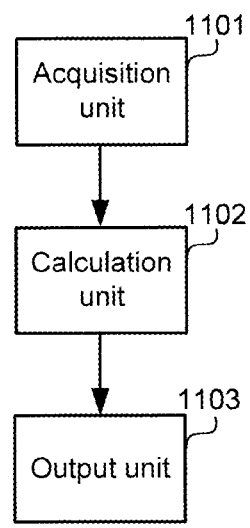
FIG. 61 is a block diagram illustrating a functional configuration of a data processing device according to the present disclosure.

In short, as illustrated in FIG. 61, the data processing device according to the present disclosure may include an acquisition unit 1101 configured to acquire data indicating blink timing of a user, a calculation unit 1102 configured to calculate index according to the synchronization degree of the blink timing of a plurality of users based on the difference in the blink timing of the plurality of users, and an output unit 1103 configured to output data according to the index.

(6) The functions realized by the control unit 1011 of the servers 1010, 1010A, 10108, and 1010C and the terminal device 1020, 1020A, 1020B, and 1020C may be realized by combinations of a plurality of programs or by coordination of a plurality of hardware resources. When the functions of the control unit 1011 or the control unit 1021 are realized using a program, a program 1131 or a program 1241 for executing this function may be provided in a state stored in a computer-readable recording medium such as various magnetic recording media, optical recording media, optical magnetic recording media, semiconductor memory, etc. The program may be distributed over a network. The present disclosure can also be understood as a data processing method.

What is claimed is:

1. A processing device comprising:
   a memory configured to store executable instructions; and
   processing circuitry configured to execute the executable instructions stored in the memory to thereby realize:
   a first acquisition unit configured to acquire a timing of a blink motion performed by a dialogue device, the timing of the blink motion being data, that controls the timing of the blink motion performed by the dialogue device, stored in the memory;
   a second acquisition unit configured to acquire a blink timing by a user performing a dialogue with the dialogue device, the blink timing by the user being data related to times when the user blinks, detected using image data generated by an imaging unit, arranged in time order; and
   a processing unit configured to perform data processing according to a difference between the timing of the blink motion performed by the dialogue device and the blink timing by the user,
   wherein the processing unit causes the dialogue device to perform dialogue data processing to change dialogue content according to the difference between the timing of the blink motion performed by the dialogue device and the blink timing by the user.

2. The processing device according to claim 1, wherein the processing unit performs the dialogue processing according to index based on the difference.

3. The processing device according to claim 1, wherein the processing unit performs the dialogue processing according to a degree, and
   the degree indicates how much the blink timing by the user is included in a predetermined period based on the timing of the blink motion.

4. The processing device according to claim 3, wherein the predetermined period includes a time range of ±500 milliseconds or less based on the timing of the blink motion performed by the dialogue device.

5. The processing device according to claim 3, wherein the processing unit performs the dialogue processing according to a first difference between the blink timing by the user and the timing of the blink motion performed by the dialogue device, the first difference being arranged in time order on a predetermined time axis, and a second difference between the blink timing by the user and the timing of the blink motion performed by the dialogue device when the order of at least one of the blink of the user and the blink motion is changed on the predetermined time axis.

6. The processing device according to claim 1, wherein the processing unit outputs evaluation data according to the difference in association with an identifier of the dialogue device.

7. The processing device according to claim 1, wherein the processing circuitry is configured to execute the executable instructions stored in the memory to further realize an environment information acquisition unit configured to acquire environment information including information indicating a peripheral environment of the dialog device, and a blink motion control unit configured to cause the dialogue device to perform the blink motion at a first timing according to the environment information.

8. The processing device according to claim 7, wherein the processing circuitry is configured to execute the executable instructions stored in the memory to further realize a storage control unit configured to store data associating the blink timing by the user with the peripheral environment in a storage device, and the blink motion control unit sets the first timing to timing according to data accumulated in the storage device and the environment information.

9. The processing device according to claim 8, wherein the blink motion control unit further causes the dialogue device to perform the blink motion at a second timing different from the first timing.

10. The processing device according to claim 1, further comprising:

an eyelid unit corresponding to an eyelid that performs the blink motion; wherein the processing circuitry is configured to execute the executable instructions stored in the memory to further realize a blink motion control unit configured to control the blink motion performed by the eyelid unit by opening and closing the eyelid unit, and the first acquisition unit acquires the timing of the blink motion performed by the eyelid unit.

11. The processing device according to claim 1, further comprising:

a display unit configured to display an object that performs the blink motion; wherein the processing circuitry is configured to execute the executable instructions stored in the memory to further realize a blink motion control unit configured to control the blink motion performed by the object displayed on the display unit, and the first acquisition unit acquires the timing of the blink motion performed by the object.

12. A processing method comprising:

acquiring a timing of a blink motion performed by a dialogue device, the timing of the blink motion being data, that controls the timing of the blink motion performed by the dialogue device, stored in a memory;

acquiring a blink timing by a user performing a dialogue with the dialogue device, the blink timing by the user being data related to times when the user blinks, detected using image data generated by an imaging unit, arranged in time order; and performing data processing according to a difference between the timing of the blink motion performed by the dialogue device and the blink timing by the user, wherein performing the data processing includes performing dialogue data processing to change dialogue content according to the difference between the timing of the blink motion performed by the dialogue device and the blink timing by the user.

13. A non-transitory computer readable storage medium storing program for causing a computer to execute:

acquiring a timing of a blink motion performed by a dialogue device, the timing of the blink motion being data, that controls the timing of the blink motion performed by the dialogue device, stored in a memory;

acquiring a blink timing by a user performing a dialogue with the dialogue device, the blink timing by the user being data related to times when the user blinks, detected using image data generated by an imaging unit, arranged in time order; and performing data processing according to a difference between the timing of the blink motion performed by the dialogue device and the blink timing by the user, wherein performing the data processing includes performing dialogue data processing to change dialogue content according to the difference between the timing of the blink motion performed by the dialogue device and the blink timing by the user.

\* \* \* \* \*